United States Patent
Nassef et al.

(10) Patent No.: US 8,440,093 B1
(45) Date of Patent: May 14, 2013

(54) METHODS AND DEVICES FOR ELECTRONIC AND MAGNETIC SENSING OF THE CONTENTS OF MICROFLUIDIC FLOW CHANNELS

(75) Inventors: Hany Nassef, San Mateo, CA (US); Geoff Facer, San Francisco, CA (US); Marc Unger, San Mateo, CA (US)

(73) Assignee: Fuidigm Corporation, South San Francisco, CA (US)

( * ) Notice: Subject to any disclaimer, the term of this patent is extended or adjusted under 35 U.S.C. 154(b) by 1629 days.

(21) Appl. No.: 11/546,939

(22) Filed: Oct. 11, 2006

Related U.S. Application Data

(63) Continuation of application No. 10/273,406, filed on Oct. 16, 2002, now abandoned.

(60) Provisional application No. 60/348,448, filed on Oct. 26, 2001.

(51) Int. Cl.
*C03C 25/68* (2006.01)
*G01N 1/10* (2006.01)

(52) U.S. Cl.
USPC .............. 216/84; 216/86; 436/180; 324/71.1

(58) Field of Classification Search ............ 216/84, 216/86; 436/180; 324/71.1
See application file for complete search history.

(56) References Cited

U.S. PATENT DOCUMENTS

| | | | |
|---|---|---|---|
| 2,656,508 A | 10/1953 | Coulter | |
| 3,570,515 A | 3/1971 | Kinner | |
| 3,747,628 A | 7/1973 | Holster et al. | |
| 3,839,176 A | 10/1974 | McCoy et al. | |
| 3,915,652 A | 10/1975 | Natelson | |
| 3,984,307 A | 10/1976 | Kamentsky et al. | |
| 4,046,159 A | 9/1977 | Pegourie | |
| 4,119,368 A | 10/1978 | Yamakazi | |
| 4,153,855 A | 5/1979 | Feingold | |
| 4,245,673 A | 1/1981 | Bouteille et al. | |

(Continued)

FOREIGN PATENT DOCUMENTS

| | | |
|---|---|---|
| EP | 0 592 094 A2 | 4/1994 |
| EP | 0 703 364 A1 | 3/1996 |

(Continued)

OTHER PUBLICATIONS

Wikipedia, The Free Encyclopedia, "Electrical Impedance", http://en.wikipedia.org/wiki/Electrical_impedance ; pp. 1-12, 2012.*

(Continued)

*Primary Examiner* — Binh X Tran
(74) *Attorney, Agent, or Firm* — Kilpatrick Townsend & Stockton LLP

(57) ABSTRACT

The presence of a detectable entity within a detection volume of a microfabricated elastomeric structure is sensed through a change in the electrical or magnetic environment of the detection volume. In embodiments utilizing electronic detection, an electric field is applied to the detection volume and a change in impedance, current, or combined impedance and current due to the presence of the detectable entity is measured. In embodiments utilizing magnetic detection, the magnetic properties of a magnetized detected entity alter the magnetic field of the detection volume. This changed magnetic field induces a current which can reveal the detectable entity. The change in resistance of a magnetoresistive element may also reveal the passage of a magnetized detectable entity.

40 Claims, 39 Drawing Sheets

U.S. PATENT DOCUMENTS

| | | | |
|---|---|---|---|
| 4,373,527 A | 2/1983 | Fischell | |
| 4,399,219 A | 8/1983 | Weaver | |
| 4,434,704 A | 3/1984 | Surjaatmadja | |
| 4,575,681 A | 3/1986 | Grosso et al. | |
| 4,581,624 A | 4/1986 | O'Connor | |
| 4,585,209 A | 4/1986 | Aine et al. | |
| 4,662,710 A | 5/1987 | ten Berge | |
| 4,675,300 A | 6/1987 | Zare et al. | |
| 4,786,165 A | 11/1988 | Yamamoto et al. | |
| 4,797,842 A | 1/1989 | Nackman et al. | |
| 4,876,504 A * | 10/1989 | Blake et al. | 324/204 |
| 4,898,582 A | 2/1990 | Faste | |
| 4,908,112 A | 3/1990 | Pace | |
| 4,936,465 A | 6/1990 | Zold | |
| 4,963,498 A | 10/1990 | Hillman et al. | |
| 4,965,743 A | 10/1990 | Malin et al. | |
| 4,992,312 A | 2/1991 | Frisch | |
| 5,032,381 A | 7/1991 | Bronstein et al. | |
| 5,085,562 A | 2/1992 | Van Lintel | |
| 5,088,515 A | 2/1992 | Kamen | |
| 5,096,388 A | 3/1992 | Weinberg | |
| 5,100,627 A | 3/1992 | Buican et al. | |
| 5,126,022 A | 6/1992 | Soane et al. | |
| 5,126,115 A | 6/1992 | Fujita et al. | |
| 5,164,558 A | 11/1992 | Huff et al. | |
| 5,171,132 A | 12/1992 | Miyazaki et al. | |
| 5,171,764 A | 12/1992 | Katayama et al. | |
| 5,224,843 A | 7/1993 | Van Lintel | |
| 5,259,737 A | 11/1993 | Kamisuki et al. | |
| 5,265,327 A | 11/1993 | Faris et al. | |
| 5,290,240 A | 3/1994 | Horres, Jr. | |
| 5,307,186 A | 4/1994 | Izumi et al. | |
| 5,336,062 A | 8/1994 | Richter | |
| 5,346,372 A | 9/1994 | Naruse et al. | |
| 5,375,979 A | 12/1994 | Trah | |
| 5,376,252 A | 12/1994 | Ekstrom | |
| 5,400,741 A | 3/1995 | DeTitta et al. | |
| 5,423,287 A | 6/1995 | Usami et al. | |
| 5,434,047 A | 7/1995 | Arnold et al. | |
| 5,452,878 A | 9/1995 | Gravesen et al. | |
| 5,454,472 A | 10/1995 | Benecke et al. | |
| 5,487,003 A | 1/1996 | Iwasawa et al. | |
| 5,496,009 A | 3/1996 | Farrell et al. | |
| 5,498,392 A | 3/1996 | Wilding et al. | |
| 5,500,071 A | 3/1996 | Kaltenbach et al. | |
| 5,512,131 A | 4/1996 | Kumar et al. | |
| 5,525,464 A | 6/1996 | Drmanac et al. | |
| 5,529,465 A | 6/1996 | Zengerle et al. | |
| 5,558,998 A | 9/1996 | Hammond et al. | |
| 5,571,410 A | 11/1996 | Swedberg et al. | |
| 5,574,893 A | 11/1996 | Southgate et al. | |
| 5,580,523 A | 12/1996 | Bard | |
| 5,587,128 A | 12/1996 | Wilding et al. | |
| 5,589,136 A | 12/1996 | Northrup et al. | |
| 5,593,130 A | 1/1997 | Hansson et al. | |
| 5,595,650 A | 1/1997 | Manz | |
| 5,608,519 A | 3/1997 | Gourley | |
| 5,632,876 A | 5/1997 | Zanzucchi et al. | |
| 5,641,400 A | 6/1997 | Kaltenbach et al. | |
| 5,642,015 A | 6/1997 | Whitehead et al. | |
| 5,656,155 A | 8/1997 | Norcross et al. | |
| 5,659,171 A | 8/1997 | Young et al. | |
| 5,660,370 A | 8/1997 | Webster | |
| 5,661,222 A | 8/1997 | Hare | |
| 5,665,070 A | 9/1997 | McPhee | |
| 5,681,024 A | 10/1997 | Lisec et al. | |
| 5,702,618 A | 12/1997 | Saaski et al. | |
| 5,705,018 A | 1/1998 | Hartley | |
| 5,716,852 A | 2/1998 | Yager et al. | |
| 5,726,751 A | 3/1998 | Altendorf et al. | |
| 5,750,015 A | 5/1998 | Soane et al. | |
| 5,757,482 A | 5/1998 | Fuchs et al. | |
| 5,759,014 A | 6/1998 | Van Lintel | |
| 5,775,371 A | 7/1998 | Pan et al. | |
| 5,779,868 A | 7/1998 | Parce et al. | |
| 5,788,468 A | 8/1998 | Dewa et al. | |
| 5,800,690 A | 9/1998 | Chow et al. | |
| 5,807,522 A | 9/1998 | Brown et al. | |
| 5,833,926 A | 11/1998 | Wurzel et al. | |
| 5,836,750 A | 11/1998 | Cabuz | |
| 5,837,200 A | 11/1998 | Diessel et al. | |
| 5,842,787 A | 12/1998 | Kopf-Sill et al. | |
| 5,852,495 A | 12/1998 | Parce | |
| 5,854,684 A | 12/1998 | Stabile et al. | |
| 5,856,174 A | 1/1999 | Lipshutz et al. | |
| 5,858,187 A | 1/1999 | Ramsey et al. | |
| 5,858,649 A | 1/1999 | Asgari et al. | |
| 5,863,502 A | 1/1999 | Southgate et al. | |
| 5,863,801 A | 1/1999 | Southgate et al. | |
| 5,869,004 A | 2/1999 | Parce et al. | |
| 5,872,010 A | 2/1999 | Karger et al. | |
| 5,875,817 A | 3/1999 | Carter | |
| 5,876,187 A | 3/1999 | Afromowitz | |
| 5,880,071 A | 3/1999 | Parce et al. | |
| 5,904,824 A | 5/1999 | Oh | |
| 5,932,799 A | 8/1999 | Moles | |
| 5,942,443 A | 8/1999 | Parce et al. | |
| RE36,350 E | 10/1999 | Swedberg et al. | |
| 5,971,355 A | 10/1999 | Biegelsen et al. | |
| 5,994,696 A | 11/1999 | Tai et al. | |
| 5,997,961 A | 12/1999 | Feng et al. | |
| 6,004,442 A * | 12/1999 | Choulga et al. | 204/416 |
| 6,007,309 A | 12/1999 | Hartley | |
| 6,042,709 A | 3/2000 | Parce et al. | |
| 6,043,080 A | 3/2000 | Lipshutz et al. | |
| 6,056,428 A | 5/2000 | Devoino et al. | |
| 6,089,534 A | 7/2000 | Biegelsen et al. | |
| 6,103,537 A | 8/2000 | Ullman et al. | |
| 6,107,044 A | 8/2000 | Nikiforov | |
| 6,123,769 A | 9/2000 | Sanjoh | |
| 6,132,685 A | 10/2000 | Kercso et al. | |
| 6,149,787 A | 11/2000 | Chow et al. | |
| 6,149,870 A | 11/2000 | Parce et al. | |
| 6,155,282 A | 12/2000 | Zachary et al. | |
| 6,167,910 B1 | 1/2001 | Chow | |
| 6,174,365 B1 | 1/2001 | Sanjoh | |
| 6,182,020 B1 | 1/2001 | Fairbanks | |
| 6,221,654 B1 | 4/2001 | Quake et al. | |
| 6,235,175 B1 | 5/2001 | Dubrow et al. | |
| 6,246,330 B1 | 6/2001 | Nielsen | |
| 6,274,337 B1 | 8/2001 | Parce et al. | |
| 6,296,673 B1 | 10/2001 | Santarsiero et al. | |
| 6,321,791 B1 | 11/2001 | Chow | |
| 6,329,209 B1 | 12/2001 | Wagner et al. | |
| 6,345,502 B1 | 2/2002 | Tai et al. | |
| 6,358,387 B1 | 3/2002 | Kopf-Sill et al. | |
| 6,375,871 B1 | 4/2002 | Bentsen et al. | |
| 6,376,971 B1 | 4/2002 | Pelrine et al. | |
| 6,409,832 B2 | 6/2002 | Weigl et al. | |
| 6,437,551 B1 * | 8/2002 | Krulevitch et al. | 324/71.1 |
| 6,488,832 B2 | 12/2002 | Heller | |
| 6,488,872 B1 | 12/2002 | Beebe et al. | |
| 6,500,323 B1 | 12/2002 | Chow et al. | |
| 6,508,988 B1 | 1/2003 | Van Dam et al. | |
| 6,520,936 B1 | 2/2003 | Mann | |
| 6,533,914 B1 | 3/2003 | Liu | |
| 6,537,799 B2 | 3/2003 | Chow et al. | |
| 6,540,895 B1 | 4/2003 | Quake et al. | |
| 6,541,071 B1 | 4/2003 | Bookbinder et al. | |
| 6,563,111 B1 | 5/2003 | Moon et al. | |
| 6,569,382 B1 | 5/2003 | Edman et al. | |
| 6,581,441 B1 | 6/2003 | Paul | |
| 6,585,939 B1 | 7/2003 | Dapprich | |
| 6,596,545 B1 | 7/2003 | Wagner et al. | |
| 6,605,472 B1 | 8/2003 | Skinner et al. | |
| 6,627,076 B2 | 9/2003 | Griffiths | |
| 6,662,818 B2 | 12/2003 | Paul et al. | |
| 6,664,104 B2 | 12/2003 | Pourahmadi et al. | |
| 6,667,124 B2 | 12/2003 | Suenaga et al. | |
| 6,677,131 B2 | 1/2004 | Yuen | |
| 6,689,473 B2 | 2/2004 | Guire et al. | |
| 6,713,327 B2 | 3/2004 | Leedy | |
| 6,716,378 B2 | 4/2004 | Yang et al. | |
| 6,736,978 B1 * | 5/2004 | Porter et al. | 210/695 |
| 6,749,814 B1 | 6/2004 | Bergh et al. | |
| 6,752,922 B2 | 6/2004 | Huang et al. | |
| 6,765,279 B2 | 7/2004 | Leedy | |

| | | | |
|---|---|---|---|
| 6,767,706 B2 | 7/2004 | Quake et al. | |
| 6,829,753 B2 | 12/2004 | Lee et al. | |
| 6,847,153 B1 | 1/2005 | Balizer | |
| 6,866,785 B2 | 3/2005 | Zare et al. | |
| 6,884,346 B2 | 4/2005 | Zare et al. | |
| 6,885,982 B2 | 4/2005 | Harris et al. | |
| 6,960,437 B2 | 11/2005 | Enzelberger et al. | |
| 2001/0027745 A1 | 10/2001 | Weigl et al. | |
| 2001/0041357 A1 | 11/2001 | Fouillet et al. | |
| 2002/0005354 A1 | 1/2002 | Spence et al. | |
| 2002/0014673 A1 | 2/2002 | Leedy | |
| 2002/0037499 A1 | 3/2002 | Quake et al. | |
| 2002/0045297 A1 | 4/2002 | Leedy | |
| 2002/0058332 A1 | 5/2002 | Quake et al. | |
| 2002/0064885 A1 | 5/2002 | Bedingham et al. | |
| 2002/0108096 A1 | 8/2002 | Lee et al. | |
| 2002/0108097 A1 | 8/2002 | Harris et al. | |
| 2002/0109114 A1 | 8/2002 | Driggs et al. | |
| 2002/0127736 A1* | 9/2002 | Chou et al. | 436/180 |
| 2002/0158022 A1 | 10/2002 | Huang et al. | |
| 2002/0164816 A1 | 11/2002 | Quake | |
| 2002/0183996 A1 | 12/2002 | Lee et al. | |
| 2002/0197603 A1 | 12/2002 | Chow et al. | |
| 2003/0008308 A1 | 1/2003 | Enzelberger et al. | |
| 2003/0049659 A1 | 3/2003 | Lapidus et al. | |
| 2003/0080442 A1 | 5/2003 | Unger | |
| 2003/0134129 A1 | 7/2003 | Lammertink et al. | |
| 2003/0143120 A1 | 7/2003 | Ruediger et al. | |
| 2003/0175947 A1 | 9/2003 | Liu et al. | |
| 2004/0096960 A1 | 5/2004 | Burd Mehta et al. | |
| 2004/0141887 A1 | 7/2004 | Mainquist et al. | |
| 2004/0209354 A1 | 10/2004 | Mathies et al. | |
| 2004/0248167 A1 | 12/2004 | Quake et al. | |
| 2005/0000900 A1 | 1/2005 | Huang et al. | |
| 2005/0019792 A1 | 1/2005 | McBride et al. | |
| 2005/0037471 A1 | 2/2005 | Liu et al. | |
| 2005/0053952 A1 | 3/2005 | Hong et al. | |
| 2005/0065735 A1 | 3/2005 | Lee et al. | |
| 2005/0084421 A1 | 4/2005 | Unger et al. | |
| 2005/0129581 A1 | 6/2005 | McBride et al. | |
| 2005/0164376 A1 | 7/2005 | Balagadde et al. | |
| 2005/0180891 A1 | 8/2005 | Webster | |
| 2005/0197652 A1 | 9/2005 | Nat | |

FOREIGN PATENT DOCUMENTS

| | | |
|---|---|---|
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| EP | 1 065 378 A2 | 1/2001 |
| GB | 2 097 692 A | 11/1982 |
| GB | 2 155 152 A | 9/1985 |
| GB | 2 308 460 A | 6/1997 |
| WO | WO 98/07069 A1 | 2/1998 |
| WO | WO 98/39645 A1 | 9/1998 |
| WO | WO 98/52691 A1 | 11/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 99/61888 A2 | 12/1999 |
| WO | WO 00/00678 A1 | 1/2000 |
| WO | WO 00/21666 A1 | 4/2000 |
| WO | WO 00/22409 A2 | 4/2000 |
| WO | WO 00/30167 A1 | 5/2000 |
| WO | WO 00/43748 A1 | 7/2000 |
| WO | WO 00/60345 A1 | 10/2000 |
| WO | WO 01/01025 A2 | 1/2001 |
| WO | WO 01/06529 A1 | 1/2001 |
| WO | WO 01/06575 A1 | 1/2001 |
| WO | WO 01/09595 A2 | 2/2001 |
| WO | WO 01/09595 A3 | 2/2001 |
| WO | WO 01/53794 A1 | 7/2001 |
| WO | WO 01/94635 A2 | 12/2001 |
| WO | WO 02/30486 A2 | 4/2002 |
| WO | WO 02/43615 A2 | 6/2002 |
| WO | WO 02/060582 A2 | 8/2002 |
| WO | WO 02/082047 A2 | 10/2002 |
| WO | WO 03/037781 A1 | 5/2003 |

OTHER PUBLICATIONS

"Last Chance For Micromachines," The Economist Technology Quarterly, 8 pages, Dec. 7, 2000.

"The Liver Chip," Technology Review, pp. 64-67, Mar. 2003.

Affholter, Joseph et al., "Engineering a Revolution," Chemistry in Britain, pp. 48-51, Apr. 1999.

Anderson, Janelle R. et al., "Fabrication of Topologically Complex Three-Dimensional Microfluidic Systems in PDMS by Rapid Prototyping," Analytical Chemistry, vol. 72, No. 14, pp. 3158-3164, Jul. 15, 2000.

Angell, James B. et al., "Silicon Micromechanical Devices," Scientific American, pp. cover, 44-55, Apr. 1983.

Armani, Deniz et al., "Re-Configurable Fluid Circuits by PDMS Elastomer Micromachining," IEEE Int. Conf. Micro Electro Mech. Syst. Tech. Digest, vol. 12, pp. 222-227, 1999.

Arnold, Frances H., "Design by Directed Evolution," Accounts of Chemical Research, vol. 31, No. 3, pp. 125-131, 1998.

Ashkin, A. et al., "Optical Trapping and Manipulation of Single Cells Using Infrared Laser Beams," Nature, vol. 330, No. 24, pp. 769-771, Dec. 31, 1987.

Ashkin, A. et al., "Optical Trapping and Manipulation of Viruses and Bacteria," Science, vol. 235, pp. 1517-1520, Mar. 20, 1987.

Ballantyne, J. P. et al., "Selective Area Metallization by Electron-Beam Controlled Direct Metallic Deposition," J. Vac. Sci. Technol., vol. 10, No. 6, pp. 1094-1097, Nov. 1973.

Barron, Annelise E. et al., "Capillary Electrophoresis of DNA in Uncross-Linked Polymer Solutions," Journal of Chromatography A, vol. 652, pp. 3-16, 1993.

Barron, Annelise E. et al., "DNA Separations by Slab Gel and Capillary Electrophoresis—Theory and Practice," Separation and Purification Methods, vol. 24, No. 1, pp. 1-118, 1995.

Barron, Annelise E. et al., "The Use of Coated and Uncoated Capillaries for the Electrophoretic Separation of DNA in Dilute Polymer-Solutions," Electrophoresis, vol. 16, pp. 64-74, 1995.

Belgrader, Phillip et al., "Rapid Pathogen Detection Using a Microchip PCR Array Instrument," Clinical Chemistry, vol. 44, No. 10, pp. 2191-2194, 1998.

Benard, W. L. et al., "A Titanium-Nickel Shape-Memory Alloy Actuated Micropump," Transducers '97, 1998 International Conference on Soild-State Sensors and Acutators, Chicago, Illionois, pp. 361-364, Jun. 16-19, 1997.

"Biochips," Nature Biotechnology, vol. 18, Supplement 2000, pp. IT43-IT44, 2000.

Black, Harvey, "Tiny Technology Promises Tremendous Profits," The Scientist, vol. 15, No. 21, 4 pages, Oct. 29, 2001.

Blanch, Harvey W. et al., Biochemical Engineering, pp. 2 cover pages and 305, 1996.

Blankenstein, Gert et al., "Modular Concept of a Laboratory on a Chip for Chemical and Biochemical Analysis," Biosensors & Bioelectronics, vol. 13, Nos. 3-4, pp. 427-438, 1998.

Bloomstein, T.M. et al., "Laser-Chemical Three-Dimensional Writing for Microelectromechanics and application to Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brechtel, R. et al., "Control of the Electroosmotic Flow by Metal-Salt-Containing Buffers," Journal of Chromatography A, vol. 716, pp. 97-105, 1995.

Brush, Michael, "Automated Laboratories," The Scientist, vol. 13, No. 4, 10 pages, Feb. 15, 1999.

Bryzek, Janusz et al., "Micromachines on The March", IEEE Spectrum, vol. 31, No. 5, pp. 20-31, May 1994.

Buchaillot, Lionel et al., "Silicon Nitride Thin Films Young's Modulus Determination by an Optical Non Destructive Method," Jpn. J. Appl. Phys., vol. 36, Part 2, No. 6B, pp. L794-L797, Jun. 15, 1997.

Budowle, Bruce et al., "Analysis of the VNTR Locus DIS80 by the PCR Followed by High-Resolution PAGE," Am. J. Hum. Genet., vol. 48, pp. 137-144, 1991.

Bucan, Tudor N. et al., "Automated Single-Cell Manipulation and Sorting by Light Trapping," Applied Optics, vol. 26, No. 24, pp. 5311-5316, Dec. 15, 1987.

Burbaum, Jonathan J. et al., "New Technologies for High-Throughput Screening," Current Opinion in.Chemical Biology, vol. 1, pp. 72-78, 1997.

Cai, Weiwen, et al., "High Resoltion Restriction Maps of Bacterial Artificial Chromosomes Constructed by Optical Mapping," Proc. Natl. Acad. Sci. USA, vol. 95, pp. 33-90-3395, Mar. 1998.

Calkins, Kathryn, "Mycometrix: Rubber Chips," BioCentury, 2 pages, Oct. 16, 2000.

Castro, Alonso et al., "Fluorescence Detection and Size Measurement of Single DNA Molecules," Analytical Chemistry, vol. 85, No. 7, pp. 849-852, Apr. 1, 1993.

Chan, Jason H. et al., "Microfabricated Polymer Devices for Automated Sample Delivery of Peptides For Analysis by Electrospray Ionization Tandem Mass Spectrometry," Analytical Chemistry, vol. 71, No. 20, pp. 4437-4444, Oct. 15, 1999.

Chang, Jun Keun et al., "Functional Integration of Serial Dilution and Capillary Electrophoresis on a PDMS Microchip," Biotechnology and Bioprocess Engineering, vol. 8, No. 4, pp. 233-239, 2003.

Chen, Chihchen et al., "Gray-Scale Photolithography Using Microfluidic Photomasks," PNAS, vol. 100, No. 4, pp. 1499-1504, Feb. 18, 2003.

Chiang, Yuh-Min et al., "Characterizing the Process of Cast Molding Microfluidic Systems," SPIE, vol. 3877, pp. 303-311, Sep. 1999.

Chiu, Chi-Sung et al., "Single Molecule Measurements Calibrate Green Fluorescent Protein Surface Densities on Transparent Beads for Use With 'Knock-In' Animals and Other Expression Systems," Journal of Neuroscience Methods, vol. 105, pp. 55-63, 2001.

Chiu, Daniel T. et al., "Patterned Deposition of Cells and Proteins Onto Surfaces by Using Three-Dimensional Dimensional Microfluidic Systems," PNAS, vol. 97, No. 6, pp. 2408-2413, Mar. 14, 2000.

Chou, Hou-Pu et al., "A Microfabricated Device for Sizing and Sorting DNA Molecules," Proc. Natl. Acad. Sci., vol. 96, pp. 11-13, Jan. 1999.

Chou, Hou-Pu et al., "A Microfabricated Rotary Pump," Biomedical Microdevices, vol. 3, No. 4, pp. 323-330, 2001.

Chou, Hou-Pu et al., "Disposable Microdevices for DNA Analysis and Cell Sorting," Proc. Solid-State Sensor and Actuator Workshop, Hilton Head, South Carolina, pp. 11-14, Jun. 8-11, 1998.

Chou, Hou-Pu et al., "Integrated Elastomer Fluidic Lab-On-A-Chip-Surface Patterning and DNA Diagnostics," Proceedings of the Solid State Actuator and Sensor Workshop, Hilton Head, South Carolina, 4 pages, 2000.

Chou, Hou-Pu et al., "Microfabricated Devices for Sizing DNA and Sorting Cells," Micro- and Nanofabricated Structures and Devices for Biomedical Environmental Applications, Proceedings of SPIE, vol. 3258, pp. 181-187, 1998.

Chou, Hou-Pu et al., "Multiple Disease Diagnostics on a Single Chip," Biophysics Lab, Caltech, pp. 1-4, Mar. 1, 2000.

Costerton, J. William et al., "Microbial Biofilms," Annu. Rev. Microbiol., vol. 49, pp. 711-745, 1995.

Cowen, S. et al., "An On-Chip Miniature Liquid Chromatography System: Design, Construction and Characterization," Mirco Total Analysis Systems. Proceedings of the µTAS '94 Workshop, University of Twente, The Netherlands, pp. 2 cover pages and 295-298, 1995.

Crosland-Taylor, P. J., "A Device for Counting Small Particles Suspended in a Fluid Through a Tube," Nature, vol. 171, pp. 37-38, Jan. 3, 1953.

Delamarche, Emmanuel et al., "Patterned Delivery of Immunoglobulins to Surfaces Using Microfluidic Networks," Science, vol. 276, pp. 779-781, May 2, 1997.

Delisa, Matthew P. et al., "Mapping Stress-Induced Changes in Autoinducer Al-2 Production in Chemostat-Cultivated *Escherichia coli* K-12," Journal of Bacteriology, vol. 183, No. 9, pp. 2918-2928, May 2001.

Dharmatilleke, Saman et al., "Three-Dimensional Silicone Device Fabrication and Interconnection Scheme for Microfluidic Application Using Sacrificial Wax Layers," Micro-Electro-Mechanical Systems (MEMS), vol. 2, pp. 413-418, 2000.

Duffy, David C. et al., "Patterning Electroluminescent Materials With Feature Sizes As Small As 5µm Usisng Elastometric Membranes as Masks for Dry Lift-Off," Advanced Materials, vol. 11, No. 7, pp. 546-552, 1999.

Duffy, David C. et al., "Rapid Prototyping of Microfluidic Switches in Poly(dimethyl siloxane) and Their Actuation by Electro-Osmotic Flow," J. Micromech. Microeng., vol. 9, pp. 211-217, 1999.

Duffy, David C. et al., "Rapid Prototyping of Microfluidic Systems in Poly(dimethylsiloxane)," Analytical Chemistry, vol. 70, No. 23, pp. 4974-4984, Dec. 1, 1998.

Effenhauser, Carlo S. et al., "Integrated Capillary Electrophoresis on Flexible Silicone Microdevices: Analysis of DNA Restriction Fragments and Detection of Single DNA Molecules on Microchips," Analytical Chemistry, vol. 69, No. 17, pp. 3451-3457, Sep. 1, 1997.

Effenhauser, Carlo S. et al., "Integrated Chip-Based Capillary Electrophoresis," Electrophoresis, vol. 18, pp. 2203-2213, 1997.

Effenhauser, Carlo S., "Integrated Chip-Based Microcolumn Separation Systems," Topics in Current Chemistry, vol. 194, pp. cover, 52-82, 1998.

Effenhauser, Carlo S. et al., "Miniaturizing a Whole Analytical Laboratory Down to Chip Size," American Laboratory, vol. 26, No. 14, pp. cover, 15, 16, 18, 1994.

Ericson, Christer et al., "Electroosmosis- and Pressure-Driven Chromatography in Chips Using Continuous Beds," Analytical Chemistry, vol. 72, No. 1, pp. 81-87, Jan. 1, 2000.

Eyal, Shulamit et al., "Velocity-Independent Microfluidic Flow Cytometry," Electrophoresis, vol. 23, pp. 2653-2657, 2002.

Fahrenberg, J. et al., "A Microvalve System Fabricated by Thermoplastic Molding," J. Micromech. Microeng., vol. 5, pp. 169-171, 1995.

Felix, Arthur M. et al., "Pegylated Peptides IV—Enhanced Biological Activity of Site-Directed Pegylated GRF Analogs," International Journal of Peptide & Protein Research, vol. 46, pp. 253-264, 1995.

Felix, Arthur M., "Site-Specific Poly(ethylene glycol)ylation of Peptides," Poly(Ethylene Glycol) Chemistry and Biological Applications, vol. ACS Symposium Series 680, pp. 2 cover pages, 218-238, 1997.

Fettinger, J. C. et al., "Stacked Modules for Micro Flow Systems in Chemical Analysis: Concept and Studies Using an Enlarged Model," Sensors and Actuators B, vol. 17, pp. 19-25, 1993.

Fielder, Stefan et al., "Dielectrophoretic Sorting of Particles and Cells in a Mircosystem," Analytical Chemistry, vol. 70, No. 9, pp. 1909-1915, May 1, 1998.

Figeys, Daniel et al., "An Integrated Microfluidics-Tandem Mass Spectrometry System for Automated Protein Analysis," Analytical Chemistry, vol. 70, No. 18, pp. 3728-3734, Sep. 15, 1998.

Figeys, Daniel et al., "Nanoflow Solvent Gradient Delivery From a Microfabricated Device for Protein Identifications by Electrospray Ionization Mass Spectrometry," Analytical Chemistry, vol. 70, No. 18, pp. 3721-3727, Sep. 15, 1998.

Fitzgerald, Deborah A., "Making Every Nanoliter Count," The Scientist, vol. 15, No. 21, 8 pages, Oct. 29, 2001.

Folch, A. et al., "Molding of Deep Polydimethylsiloxane Microstructures for Microfluidics and Biological Applications," Journal of Biomechanical Engineering, vol. 121, pp. 28-34, Feb. 1999.

Fu, Anne Y. et al., "A Microfabricated Fluorescence-Activated Cell-Sorter," Nature Biotechnology, vol. 17, pp. 1109-1111, Nov. 1999.

Fu, Anne Y. et al., "An Integrated Microfabricated Cell Sorter," Analytical Chemistry, vol. 74, No. 11, pp. 2451-2457, Jun. 1, 2002.

Fulwyler, M. J., "Electronic Separation of Biological Cells by Volume,"Science, pp. 910-911, Nov. 1965.

Galambos, Paul et al., "Electrical and Fluidic Packaging of Surface Micromachined Electro-Microfluidic Devices," 8 pages, no date.

Gao, Jun et al., "Integrated Microfluidic System Enabling Protein Digestion, Peptide Separation, and Protein Identification," Analytical Chemistry, vol. 73, No. 11, pp. 2648-2655, Jun. 1, 2001.

Garno, Jayne C. et al., "Production of Periodic Arrays of Protein Nanostructures Using Particle Lithography," Langmuir, vol. 18, No. 21, pp. 8186-8192, 2002.
Gass, V. et al., "Integrated Flow-Regulated Silicon Micropump," Sensors and Actuators A, vol. 43, pp. 335-338, 1994.
Geng, Xindu et al., "Retention Model for Proteins in Reversed-Phase Liquid Chromatography," Journal of Chromatography, vol. 296, pp. 15-30, 1984.
Gerlach, Torsten, "Pumping Gases by a Silicon Micro Pump With Dynamic Passive Valves," Transducers '97, 1997 International Conference on Solid-State Sensors and Actuators, Chicago, Illinois, pp. 357-360, Jun. 16-19, 1997.
Ginsberg, Michael A., "New Laser System Measure DNA Fragments," Biophotonics International, p. 20, Nov./Dec. 1996.
Giusti, Alan et al., "Application of Deoxyribonucleic Acid (DNA) Polymorphisms to the Analysis of DNA Recovered From Sperm," Journal of Forensic Sciences, vol. 31, No. 2, pp. 409-417, Apr. 1986.
Goll, C. et al., "Microvalves With Bistable Buckled Polymer Diaphragms," J. Micromech. Microeng., vol. 6, pp. 77-79, 1996.
Gombotz, W. R. et al., "Pegylation: A Tool to Enhance Protein Delivery," Abstracts of Papers, American Chemical Society, vol. 217, Part 2, 2 pages, Mar. 21-25, 1999.
Gonzalez, Jesus E. et al., "Improved Indicators of Cell Membrane Potential That Use Fluorescence Resonance Energy Transfer," Chemistry & Biology, vol. 4, No. 4, pp. 269-277, Apr. 1997.
Goodwin, Peter M. et al., "Rapid Sizing of Individual Fluorescently Stained DNA Fragments by Flow Cytometry," Nucleic Acids Research, vol. 21, No. 4, pp. 803-806, 1993.
Gravesen, Peter et al., "Microfluidics—A Review," J. Micromech. Microeng., vol. 3, pp. 168-192, 1993.
Greene, Chana, "Characterizing the Properties of PDMS," pp. 1-11, Summer 2000.
Grover, William H. et al., "Monolithic Membrane Valves and Diaphragm Pumps for Practical Large-Scale Integration Into Glass Microfluidic Devices," Sensors and Actuators B, vol. 89, pp. 315-323, 2003.
Guérin, L. J. et al., "Simple and Low Cost Fabrication of Embedded Micro-Channels by Using a New Thick-Film Photoplastic," Transducers '97, 1997 International Conference on Solid-State Sensors and Actuators, Chicago, Illinois, pp. 1419-1422, Jun. 18-19, 1997.
Guerra, Patricia I. et al., "PEGylation Prevents the N-Terminal Degradation of Megakaryocyte Growth and Development Factor," Pharmaceutical Research, vol. 15, No. 12, pp. 1822-1827, 1998.
Hancock, Robert E. W., "A Brief on Bacterial Biofilms," Nature Genetics, vol. 29, p. 360, Dec. 2001.
Hanes, Jozef, et al., "In Vitro Selection and Evolution of Functional Proteins by Using Ribosome Display," Proc. Natl. Acad. Sci. USA, vol. 94, pp. 4937-4942, May 1997.
Hansen, Carl. L. et al., "A Robust and Scalable Microfluidic Metering Method That Allows Protein Crystal Growth by Free Interface Diffusion," PNAS, vol. 99, No. 26, pp. 16531-16536, Dec. 24, 2002.
Hansen, Carl. L. et al., "Systematic Investigation of Protein-Phase Behavior With a Microfluidic Formulator," PNAS Early Edition, 6 pages, 2004.
Harrison, D. Jed et al., "Integration of Analytical Systems Incorporating Chemical Reactions and Electrophoretic Separation," Micro Total Analysis Systems, Proceedings of the μTAS '94 Workshop, University of Twente, The Netherlands, pp. 2 cover pages and 105-115, 1995.
Harrison, D. Jed et al., "Micromachining a Miniaturized Capillary Electrophoresis-Based Chemical Analysis System on a Chip," Science, vol. 261, pp. 895-897, Aug. 13, 1993.
Henion, Jack et al., "Capillary Electrophoresis/Mass Spectrometry: From One Meter Capillaries to Chip-Based Devices," 2 pages, 1999.
Heo, Jinseok et al., "A Microfluidic Bioreactor Based on Hydrogel-Entrapped E. coli: Cell Viability, Lysis, and Intracellular Enzyme Reactions," Analytical Chemistry, vol. 75, No. 1, Jan. 1, 2003.
Herbert, D., "Continue Culture of Bacteria," The Journal of General Microbiology, vol. 15, pp. 2 cover pages and iv, 1956.
Herbet, D. et al., "The Continuous Culture of Bacteria: A Theortical and Experimental Study," J. Gen. Microbiol., vol. 14, pp. 601-622, 1956.
Hermanson, Greg T. et al., "Chapter 2—Activation Methods," Immobilized Affinity Ligand Techniques, Academic Press, pp. 2 cover pages, 51-136, 1992.
Hicks, Jennifer, "Genetics and Drug Discovery Dominate Microarray Research," R&D Magazine, pp. 28-33, Feb. 1999.
Hoffmuller, Ulrich et al., "In Vitro Evolution and Selectrion of Proteins: Ribosome Display for Larger Libraries," Agnew. Chem. Int. Ed., vol. 37, No. 23, pp. 3241-3243, 1998.
Hofmann, Oliver et al., "Modular Appraoch to Fabrication of Three-Dimensional Microchannel Sytems in PDMS—Application to Sheath Flow Mircochips," Lab on a Chip, vol. 1, pp. 108-114, 2001.
Hong, Jong Wook et al., "A Nanoliter-Scale Nucleic Acid Processor with Parallel Architecture," Nature Biotechnology, vol. 22, No. 4, pp. 1-5, Apr. 2004.
Hopfgartner, Gerard et al., "Exact Mass Measurement of Product Ions for the Structural Elucidation of Drug Metabolites with a Tandem Quadrupole Orthogonal-Acceleration Time-Of-Flight Mass Spectrometer," Journal of The American Society for Mass Spectrometry, vol. 10, pp. cover, 1305-1314, Dec. 1999.
Horn, Howard, "Lab Chips Sector: Microtechnologies are Changing Healthcare and More," Life Sciences, pp. 19-21, Mar. 20, 2001.
Hornbeck, Larry J. et al., "Bistable Deformable Miorror Device," Spatial Light Modulations and Applications 1988 Technical Digest Series, vol. 8, Postconference Edition, pp. cover, 107-110, Jun. 15-17, 1988.
Hosokawa, Kazuo et al., "Microfluidic Device for Mixing of Capillary-Driven Liquids," IEEJ Trans. SM, vol. 123, No. 1, pp. 23-24, 2003.
Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.
Hosokawa, Kazuo et al., "Handling of Picoliter Liquid Samples in a Poly(dimethylsiloxane)-Based Microfluidic Device," Analytical Chemistry, vol. 71, No. 20, pp. 4781-4785, Oct. 15, 1999.
Ikuta, Koji et al., "Three Dimensional Micro Integrated Fluid Systems (MIFS) Fabricated by Stereo Lithography," IEEE, pp. 1-6, 1994.
Ingraham, John L. et al., Growth of the Bacterial Cell, pp. 3 cover pages and 230, 1983.
Jacobson, Ken et al., "International Workshop on the Application of Fluorescence Photobleaching Techniques to Problems in Cell Biology," Federation Proceedings, vol. 42, No. 1, pp. 72-79, Jan. 1983.
Jacobson, Stephen C. et al., "High-Speed Separations on a Microchip," Analytical Chemistry, vol. 66, No. 7, pp. 1114-1118, Apr. 1, 1994.
Jacobson, Stephen C. et al., "Microfluidic Devices for Electrokinetically Driven Parallel and Serial Mixing," Analytical Chemistry, vol. 71, No. 20, pp. 4455-4459, Oct. 15, 1999.
Jacobson, Stephen C. et al., "Open Channel Electrochromatography on a Microchip," Analytical Chemistry, vol. 66, No. 14, pp. 2369-2373, Jul. 15, 1994.
Jannasch, H. W. et al., "Experimental Bacterial Ecology Studied in Continuous Culture," Advances in Microbial Physiology, vol. 11, pp. cover and 165-212, 1974.
Jeffreys, Alec J. et al., "Hypervariable 'Minisatellite' Regions in Human DNA," Nature, vol. 314, pp. 67-73, Mar. 7, 1985.
Jerman, Hal, "Electrically-Activated, Normally-Closed Diaphragm Valves," Transducers '91, 1991 International Conference on Solid-State Sensors and Actuators, pp. cover, 1045-1048, 1991.
Jermutus, Lutz, et al., "Recent Advances in Producing and Selecting Functional Proteins by Using Cell-Free Translation," Current Opinion in Biotechnology, vol. 9, pp. 534-548, 1998.
Jo, Byung-Ho et al., "Fabrication of Three-Dimensional Microfluidic Systems by Stacking Molded Polydimethylsiloxane (PDMS) Layers" SPIE, vol. 3877, pp. 222-229, Sep. 1999.
Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.
Ju, Li-Ya et al., "Application of Silver Staining to the Rapid Typing of the Polymorphism of HLA-DQ Alleles by Enzymatic Amplification and Allele-Specific Restriction Fragment Length Polymorphism," Electrophoresis, vol. 12, pp. 270-273, 1991.

Juárez-Martinez, G. et al., "High-Throughput Screens for Postgenomics: Studies of Protein Crystallization Using Microsystems Technology," Analytical Chemistry, vol. 74, No. 14, pp. 3505-3510, Jul. 15, 2002.
Jung, D. R. et al., "Chemical and Physical Interactions At Metal/Self-Assembled Organic Monolayer Interfaces," pp. 1-54, 1994.
Kagan, C. R., "Organic-Inorganic Hybrid Materials As Semiconducting Channels in Thin-Film Field-Effect Transistors," Science, vol. 286, pp. 945-947, Oct. 29, 1999.
Kamentsky, Louis A. et al., "Spectrophotometer: New Instrument for Ultrarapid Cell Analysis," Science, vol. 150, pp. 630-631, Oct. 29, 1965.
Kanter, Evan et al., "Analysis of Restriction Fragment Length Polymorphisms in Deoxyribonucleic Acid (DNA) Recovered From Dried Bloodstains," Journal of Forensic Sciences, vol. 31, No. 2, pp. 403-408, Apr. 1986.
Kapur, Ravi et al., "Fabrication and Selective Surface Modification of 3-Dimensionally Textured Biomedical Polymers From Etched Silicon Substrates," Journal of Biomedical Materials Research, vol. 33, pp. 205-216, 1996.
Kawano, Yasushi et al., "Rapid Isolation and Identification of *Staphylococcal exoproteins* by Reverse Phase Capillary High Performance Liquid Chromatography-Electrospray Ionization Mass Spectrometry," FEMS Microbiology Letters, vol. 189, pp. 103-108, 2000.
Keller, Richard A. et al., "Single-Molecule Fluorescence Analysis in Solution," Applied Spectroscopy, vol. 50, No. 7, pp. 12A-30A, Jul. 1996.
Kenis, Paul J. A. et al., "Microfabrication Inside Capillaries Using Multiphase Laminar Flow Patterning," Science, vol. 285, pp. 83-85, Jul. 2, 1999.
Khoo, Melvin et al., "A Novel Micromachined Magnetic Membrane Microfluid Pump," pp. 1-4, no date.
Kim, Enoch et al., "Micromolding in Capillaries: Applications in Materials Science," J. Am. Chem. Soc., vol. 118, No. 24, pp. 5722-5731, 1996.
Kim, Enoch et al., "Polymer Microstructures Formed by Moulding in Capillaries," Nature, vol. 376, pp. 581-584, Aug. 17, 1995.
Kirk-Othmer, "Concise Encyclopedia of Chemical Technology" John Wiley & Songs, 5 pages, 1985.
Kodera, Yoh et al., "Pegylation of Proteins and Bioactive Substances for Medical and Technical Applications," Prog. Polym. Sci., vol. 23, pp. 1233-1271, 1998.
Kopp, Martin U. et al., "Chemical Amplification: Continuous-Flow PCR on a Chip," Science, vol. 280, pp. 1046-1048, May 15, 1998.
Kuhn, Lawrence et al., "Silicon Charge Electrode Array for Ink Jet Printing," IEEE Transactions on Electron Devices, vol. ED-25, No. 10, pp. 1257-1260, Oct. 1978.
Kumar, Amit et al., "Features of Gold Having Micrometer to Centimeter Dimensions Can Be Formed Through a Combination of Stamping With an Elastomeric Stamp and an Alkanethiol 'Ink' Followed by Chemical Etching," Appl. Phys. Lett., vol. 63, No. 14, pp. 2002-2004, Oct. 4, 1993.
Kumar, Amit et al., "Patterning Self-Assembled Monolayers: Applications in Materials Science," Langmuir, vol. 10, pp. 1498-1511, 1994.
Lagally, Eric T. et al., "Fully Integrated PCR-Capillary Electrophoresis Microsystem for DNA Analysis," Lab on a Chip, vol. 1, pp. 102-107, 2001.
Lagally, Eric T. et al., "Monolithic Integrated Microfluidic DNA Amplification and Capillary Electrophoresis Analysis Syetem," Sensors and Actuators B, vol. 63, pp. 138-146, 2000.
Lagally, E. T. et al., "Single-Molecule DNA Amplification and Analysis in an Integrated Microfluidic Device," Analytical Chemistry, vol. 73, No. 3, pp. 565-570, Feb. 1, 2001.
Lammerink, T. S. J. et al., "Modular Concept for Fluid Handling Systems," IEEE, pp. 389-394, 1996.
Lane, P. G., "Analysis of a Continuous-Culture Technique for the Selection of Mutants Tolerent to Extreme Environmental Stress," Biotechnology and Bioengineering, vol. 65, No. 4, pp. 397-406, Nov. 20, 1999.
Lawrence, J. R. et al., "Optical Sectioning of Microbial Biofilms," Journal of Bacteriology, vol. 173, No. 20, pp. 6558-6567, Oct. 1991.

Lazar, Iulia M. et al., "Novel Microfabricated Device for Electrokinetically Induced Pressure Flow and Electrospray Ionization Mass Spectrometry," Journal of Chromatography A, vol. 892, pp. 195-201, 2000.
Lee, L. Stanford et al., "Prolonged Circulating Lives of Single-Chain Fv Proteins Conjugated With Polyethylene Glycol: A Comparison of Conjugation Chemistries and Compounds," Bioconjugate Chem., vol. 10, pp. 973-981, 1999.
Lessard, Guillaume A. et al., "A Scanning Apertureless Fluorescence Microscope," 8 pages, 1999.
Levine, Leanna M. et al., "Measurement of Specific Protease Activity Utilizing Fluorescence Polarization," Analytical Biochemistry, vol. 247, pp. 83-88, 1997.
Li, Jianjun et al., "Integration of Microfabricated Devices to Capillary Electrophoresis-Electrospray Mass Spectrometry Using a Low Dead Volume Connection: Application to Rapid Analyses of Proteolytic Digests," Analytical Chemistry, vol. 71, No. 15, pp. 3036-3045, Aug. 1, 1999.
Li, Paul C. H. et al., "Transport, Manipulation, and Reaction of Biological Cells On-Chip Using Electrokinetic Effects," Analytical Chemistry, vol. 69, No. 8, pp. 1564-1568, Apr. 15, 1999.
Licklider, Larry et al., "A Micromachined Chip-Based Electrospray Source for Mass Spectrometry," Analytical Chemistry, vol. 72, No. 2, pp. 367-375, Jan. 15, 2000.
Lin, L. Y. et al., "Free-Space Micromachined Optical Switches for Optical Networking," IEEE Journal of Selected Topics in Quantum Electronics, vol. 5, No. 1, pp. 4-9, Jan. 1999.
Lin, Yuehe et al., "Laser Micromachined Isoelectric Focusing Device on Polymer Substrate for Electrospray Mass Spectrometry," SPIE, vol. 3877, pp. 28-35, Sep. 1999.
Liu, Hanghui et al., "Development of Multichannel Devices With an Array of Electrospray Tips for High-Throughput Mass Spectrometry," Analytical Chemistry, vol. 72, No. 14, pp. 3303-3310, Jul. 15, 2000.
Liu, Jian et al., "A Nanoliter Rotary Device for Polymerase Chain Reaction," Electrophoresis, vol. 23, pp. 1531-1536, 2002.
Llopis, Juan et al., "Ligand-Dependent Interactions of Coactivators Steroid Receptor Coactivator-1 and Peroxisome Proliferator-Activated Receptor Binding Protein With Nuclear Hormone Receptors Can Be Imaged in Live Cells and are Required for Transcription," PNAS, vol. 97, No. 8, pp. 4363-4368, Apr. 11, 2000.
Lötters, J C et al., "The Mechanical Properties of the Rubber Elastic Polymer Polydimethylsiloxane for Sensor Applications," J. Micromech. Microeng., vol. 7, pp. 145-147, 1997.
Lucy, Charles A. et al., "Characterization of the Cationic Surfactant Induced Reversal of Electroosmotic Flow in Capillary Electrophoresis," Anal. Chem., vol. 68, pp. 300-305, 1996.
Maluf, N., "An Introduction to Microelectromechanical Systems Engineering," Artech House Publishers, Boston London, pp. 42-45, Dec. 1999.
Manz, A. et al., "Micromachining of Monocrystalline Silicon and Glass for Chemical Analysis Systems," Trends in Analytical Chemistry, vol. 10, No. 5, pp. 144-149, 1991.
Marešová, H. et al., "A Chemostat Culture As a Tool for the Improvement of a Recombinant *E. coli* Strain Over-Producing Penicillin G Acylase," Biotechnology and Bioengineering, vol. 75, No. 1, pp. 46-52, Oct. 5, 2001.
Marshall, Sid, "Fundamental Changes Ahead for Lab Instrumentation," R&D Magazine, 5 pages, Feb. 1999.
Marsili, Ray, "Lab-On-A-Chip Poised to Revolutionize Sample Prep," R&D Magazine, 5 pages, Feb. 1999.
Mason, T. G. et al., "Shear Rupturing of Droplets in Complex Fluids," Langmuir, vol. 13, pp. 4600-4613, 1997.
Mastrangelo, C. H. et al., "Vacuum-Sealed Silicon Micromachined Incandescent Light Source," IEDM, pp. 503-506, 1989.
Maule, John, "Pulsed-Field Gel Electrophoresis," Molecular Biotechnology, vol. 9, pp. 107-126, 1998.
McDonald, J. Cooper et al., "Fabrication of Microfluidic Systems in Poly(dimethylsiloxane)," Electrophoresis, vol. 21, pp. 27-40, 2000.
McDonald, J. Cooper et al., "Poly(dimethylsiloxane) as a Material for Fabricating Microfluidic Devices," Accounts of Chemical Research, vol. 35, No. 7, pp. 491-499, 2002.

Menchen, Steve et al., "Flowable Networks As DNA Sequencing Media in Capillary Columns," Electrophoresis, vol. 17, pp. 1451-1459, 1996.

Moldavan, Andrew, "Photo-Electric Technique for the Counting of Microscopical Cells," Science, vol. 80, No. 2069, pp. 188-189, Aug. 24, 1934.

Monod, Jacques, "The Growth of Bacterial Cultures," Annual Review of Microbiology, vol. III, pp. cover and 371-394, 1949.

Muller, Richard S. et al., "Surface-Micromachined Microoptical Elements and Systems," Proceedings of the IEEE, vol. 86, No. 8, pp. 1705-1720, Aug. 1998.

Murray, Vincent et al., "Detection of Polymorphisms Using Thermal Cycling With a Single Oligonucleotide on a DNA Sequencing Gel," Human Mutation, vol. 2, pp. 118-122, 1983.

Nagai, Yasuo et al., "A Fluorescent Indicator for Visualizing cAMP-Induced Phosphorylation in Vivo," Nature Biotechnology, vol. 18, pp. 313-316, Mar. 2000.

Nakamura, Yusuke et al., "Variable Number of Tanden Repeat (VNTR) Markers for Human Gene Mapping," Science, vol. 235, pp. 1616-1622, Mar. 27, 1987.

New Objective, Inc., "What Is Electrospray," www.newobjective.com/electrospray/electrospray.html, 4 pages, 1999.

Ng, Jessamine M. K. et al., "Components for Integrated Poly(Dimethylsiloxane) Microfluidic Systems," Electrophoresis, vol. 23, pp. 3461-3473, 2002.

Nielsen, Jens et al., Bioreaction Engineering Principles, Second Edition, pp. 2 cover pages and 42-45, 2003.

Novick, Aaron et al., "Description of the Chemostat," Science, vol. 112, pp. 715-716, Dec. 15, 1950.

Novick, Aaron et al., "Experiments With the Chemostat on Spontaneous Mutations of Bacteria," Proc. N. A. S., vol. 36, pp. 708-719, 1950.

Oleschuk, Richard D. et al., "Analytical Microdevices for Mass Spectrometry," Trends in Analytical Chemistry, vol. 19, No. 6., pp. 379-388, 2000.

Olsson, Anders et al., "Simulation Studies of Diffuser and Nozzle Elements for Valve-Less Micropumps," Transducers '97, 1997 International Conference on Solid-State Sensors and Actuators, Chicago, Illinois, pp. 1039-1042, Jun. 16-19, 1997.

O'Reilly, Marie-Anne J. et al., "The Technique of Pulsed Field Gel Electrophoresis and its Impact on Molecular Immunology," Journal of Immunological Methods, vol. 131, pp. 1-13, 1990.

Parker, Gregory J. et al., "Development of High Throughput Screening Assays Using Fluorescence Polarization Nuclear Receptor-Ligand Binding and Kinase/Phophatase Assays," Journal of Biomolecular Screening, vol. 5, No. 2, pp. 77-85, 2000.

Petty, Jeffrey T. et al., "Characterization of DNA Size Determination of Small Fragments by Flow Cytometry," Anal. Chem., vol. 67, pp. 1755-1761, 1995.

Pethig, Ronald et al., "Applications of Dielectrophoresis in Biotechnology," Tibtech, vol. 15, pp. 426-432, Oct. 1997.

Poplawski, M. E. et al., "A Sample Packagin Process for Chemical Sensors," Solid-State Sensor and Actuator Workshop, Hilton-Head, South Caroline, pp. 25-28, Jun. 13-16, 1994.

Protana website, "NanoES Products," www.protana.com/products/default.asp, 3 pages, Sep. 19, 2000.

Qin, Dong et al., "Elastomeric Light Valves," Adv. Mater., vol. 9, No. 5, pp. 407-410, 1997.

Qin, Dong et al., "Photolithography with Transparent Reflective Photomasks" J. Vac. Sci. Technol. B, vol. 16, No. 1, pp. 98-103, Jan. 1998.

Qu, Mingbo et al., "Toxicity and Biodegradation of Formaldehyde in Anaerobic Methanogenic Culture," Biotechnology and Bioengineering, vol. 55, No. 5, pp. 727-736, Sep. 5, 1997.

Quake, Stephen R. et al., "From Micro- to Nanofabrication With Soft Materials," Science, vol. 290, pp. 1536-1540, Nov. 24, 2000.

Rapp, R. et al., "LIGA Micropump for Gases and Liquids," Sensors and Actuators A, vol. 40, pp. 57-61, Jan. 1994.

Roberts, Richard W. et al., "RNA-Peptide Fusions for the in Vitro Selection of Peptides and Proteins," Proc. Natl. Acad. Sci. USA, vol. 94, pp. 12297-12302, Nov. 1997.

Rotman, Boris, "A Simplified Device for Continuous Growth of Microorganisms," Journal of Bacteriology, vol. 70, pp. 485-486, 1955.

Rouhi, Maureen, "Sizing, Sorting DNA One Piece At a Time," C&EN, pp. 5-6, Jan. 11, 1999.

Roylance, Lynn Michelle et al., "A Batch-Fabricated Silicon Accelerometer," IEEE Transactions on Electron Devices, vol. ED-26, No. 12, pp. 1911-1917, Dec. 1979.

Samad, Akhtar et al., "Optical Mapping: A Novel, Single-Molecule Approach to Genomic Analysis," Genome Research, pp. 1-4, 1995.

Sandia National Laboratories, "Electro Microfluidic Dual In-Line Package (EMDIP)," 2 pages, no date.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Prototyping and Development of Microfluidic and BioMEMS Devices," IVD Technology, 12 pages, Jun. 2002.

Schasfoort, Richard B. M. et al., "Field-Effect Flow Control for Microfabricated Fluidic Networks," Science, vol. 286, pp. 942-945, Oct. 29, 1999.

Schomburg, W. K. et al., "Fabrication of Polymer Microcomponents With the AMANDA-Process," New Materials and Directions, Eurosensors XII, pp. 711-714, Sep. 13-16, 1998.

Schueller, Oliver J. A. et al., "Fabrication of Glass Carbon Microstructures by Soft Lithography," Sensors and Actuators A, vol. 72, pp. 126-139, 1999.

Schwartz, David C. et al., "Optical Mapping Approaches to Molecular Genomics," Current Opinion in Biotechnology, vol. 8, pp. 70-74, 1997.

Seethala, Ramakrishna et al., "A Fluorescence Polarization Competition Immunoassay for Tyrosine Kinases," Anaylytical Biochemistry, vol. 255, pp. 257-262, 1998.

Shevchenko, Andrej et al., "Rapid 'de Novo' Peptide Sequencing by a Combination of Nanoelectospray, Isotopic Labeling and a Quadrupole/Time-Of-Flight Mass Spectometer," Rapid Communications in Mass Spectrometry, vol. 11, pp. 1015-1024, 1997.

Shinohara, Jun et al., "A High Pressure-Resistance Micropump Using Active and Normally-Closed Valves," IEEE, pp. 86-91, 2000.

Shoji, Shuichi, "Fluids for Sensor Systems," Topics in Current Chemistry, vol. 194, pp. 163-188, 1998.

Shoji, Shuichi et al., "Smallest Dead Volume Microvalves for Integrated Chemical Analyzing Systems," Transducers '91, 1991 International Conference on Solid-State Sensors and Actuators, San Francisco, California, pp. cover, 1052-1055, 1991.

Shuler, Michael L. et al., "Chapter 6—How Cells Grow," Bioprocess Engineering Basic Concepts, Second Edition, pp. 2 cover pages and 155-200, 2002.

Sklar, Larry A. et al., Sample Handling for Kinetics and Molecular Assembly in Flow Cytometry, SPIE, vol. 3256, pp. 144-153, 1998.

Smits, J.G., "Piezoelectric Micropump with Three Valves Working Peristaltically," Sensors and Actuators, vol. A21-A23, pp. 203-206, 1990

Sohn, L. L. et al., "Capacitance Cytometry: Measuring Biological Cells One by One," PNAS, vol. 97, No. 20, pp. 10687-10690, Sep. 26, 2000.

Spicer, C. C., "The Theory of Bacterial Constant Growth Apparatus," Biometrics, pp. 225-230, Jun. 1955.

Stemmer, Willem P. C. et al., "Rapid Evolution of a Protein in vitro by DNA Shuffling," Nature, vol. 370, pp. 389-390, Aug. 4, 1994.

Sussman, Norman L. et al., "The Predictive Nature of High-Throughput Toxicity Screening Using a Human Hepatocyte Cell Line," Cell Notes, Issue 3, pp. 7-10, 2002.

Swart, Remco et al., "Recent Progress in Open Tubular Liquid Chromatography," Trends in Analytical Chemistry, vol. 16, No. 6, pp. 332-342, 1997.

Sweet, Richard G., "Chapter 9—Flow Sorters for Biologic Cells," Flow Cytometry and Sorting, John Wiley & Sons, pp. 5 cover pages and 177-189, 1979.

Takahashi, Akiyuki et al., "Measurement of Intracellular Calcium," Physiological Reviews, vol. 79, No. 4, pp. 1089-1125, Oct. 1999.

Tatari, Zohreh et al., "HLA-Cw Allele Analysis by PCR-Restriction Fragment Length Polymorphism: Study of Known and Additional Alleies," Proc. Natl. Acad. Sci. USA, vol. 92, pp. 8803-8807, Sep. 1995.

Tawfik, Dan S. et al., "Man-Made Cell-Like Compartments for Molecular Evolution," Nature Biotechnology, vol. 16, pp. 652-656, Jul. 1998.

Taylor, Anne M. et al., "Microfluidic Multicompartment Device for Neuroscience Research," Langmuir, vol. 19, pp. 1551-1556, 2003.

Terry, Stephen C. et al., "A Gas Chromatographic Air Analyzer Fabricated on a Silicon Wafer," IEEE Transactions on Electron Devices, vol. ED-26, pp. 1880-1886, Dec. 1979.

Todd, Paul et al., "Chapter 12—Cell Electrophoresis," Flow Cytometry and Sorting, John Wiley & Sons, pp. 5 cover pages and 217-229, 1979.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Inustrial Chemistry, Sections 6 to 6.3, Topic: Carbon Black, Sixth Edition, 7 pages, 1999.

Unger, Marc A. et al., "Monolithic Microfrabicated Valves and Pumps by Multilayer Soft Lithography," Science, vol. 288, pp. 113-116, Apr. 7, 2000.

Unger, M., et al., "Single-Molecule Fluorescence Observed With Mercury Lamp Illumination," Biotechniques, vol. 27, No. 5, pp. 1008-1014, Nov. 1999.

Vahey, Paul G. et al., "Development of a Positive Pressure Driven Micro-Fabricated Liquid Chromatographic Analyzer Through Rapid-Prototyping With Poly(dimethylsiloxane) Optimizing Chromatographic Efficiency With Sub-Nanoliter Injections," Talanta, vol. 51, pp. 1205-1212, 2000.

Van De Pol, F.C.M. et al., "A Thermo-Pneumatic Actuation Principle for a Microminiature Pump and Other Micromechanical Devices," Sensors and Actuators, vol. 17, Nos. 1-2, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of the μTAS '94 Workshop, University of Twente, The Netherlands, 17 pages, Nov. 21-22, 1994.

Van Der Woerd, Mark et al., "Lab-On-A-Chip Based Protein Crystallization," National Aeronautics and Space Administration and Caliper, pp. 1-27, Oct. 25, 2001.

Van Der Woerd, Mark et al., "The Promise of Macromolecular Crystallization in Microfluidic Chips," Journal of Structural Biology, vol. 142, pp. 180-187, 2003.

Van Dilla, M. A. et al., "Cell Microfluorometry: A Method for Rapid Fluorescence Measurement," Science, vol. 163, pp. 1213-1214, Mar. 14, 1969.

Van Dilla, Marvin A. et al., "Chapter 2—Introduction and Resume of Flow Cytometry and Sorting," Flow Cytometry and Sorting, John Wiley & Sons, pp. 5 cover pages and 11-37, 1979.

Velev, Orlin D., "On-Chip Manipulation of Free Droplets," Nature, vol. 426, pp. 515-516, Dec. 4, 2003.

Veronese, F. M. et al., "Influence of PEGylation on the Release of Low and High Molecular-Weight Proteins From PVA Matrices," Journal of Bioactive and Compatible Polymers, vol. 14, pp. 315-330, Jul. 1999.

Veronese, Francesco M., "Peptide and Protein PEGylation: A Review of Problems and Solutions," Biomaterials, vol. 22, pp. 405-417, 2001.

Verpoorte, Elisabeth M. J. et al., "Three-Dimensional Micro Flow Manifolds for Miniaturized Chemical Analysis Systems," J. Micromech. Microeng., vol. 7, pp. 246-256, 1994.

Vieider, Christian et al., "A Pneumatically Actuated Micro Valve With a Silicon Rubber Membrane for Integration With Fluid Handling Systems," Transducers '95, 8th International Conference on Solid-State Sensors and Actuators and Eurosensors IX, Stockholm, Sweden, pp. 284-286, Jun. 25-29, 1995.

Vogelstein, Bert et al., "Digital PCR," Proc. Natl. Acad. Sci. USA, vol. 96, pp. 9236-9241, Aug. 1989.

Volkmuth, W. D. et al., "DNA Electrophoresis in Microlithographic Arrays," Nature, vol. 358, pp. 600-602, Aug. 13, 1992.

Ward, Keith B. et al., "Automatic Preparation of Protein Crystals Using Laboratory Robotics and Automated Visual Inspection," Journal of Crystal Growth, vol. 90, pp. 325-339, 1988.

Washizu, Masao et al., "Molecular Dielectrophoresis of Biopolymers," IEEE Transactions on Industry Applications, vol. 30, No. 4. pp. 835-843, Jul. 1994.

Webster, J. R. et al., "Monolithic Capillary Gel Electrophoresis Stage With On-Chip Detector," IEEE, pp. 491-496, 1996.

Weigl, Bernhard H., "Microfluidics-Based Lab-On-A-Chip Systems," IVD Technology Magazine, 8 pages, Nov./Dec. 2000.

Whelen, A. Christian et al., "The Role of Nucleic Acid Amplification and Detection in The Clinical Microbiology Laboratory," Annu. Rev. Microbiol., vol. 50, pp. 349-373, 1996.

Whitesides, George M. et al., "Flexible Methods for Microfluidics," Physics Today, pp. 42-48, Jun. 2001.

Whitesides, George M. et al., "Soft Lithography in Biology and Biochemistry," Annu. Rev. Biomed. Eng., vol. 3, pp. 335-373, 2001.

Wiebe, Marilyn G. et al., "Evolution of a Recombinant (Gucoamylase-Producing) Strain of Fusarium venenatum A3/5 in Chemostat Culture," Biotechnology and Bioengineering, vol. 73, No. 2, pp. 146-156, Apr. 20, 2001.

Wilbur, James L. et al., "Lithographic Molding: A Convenient Route to Structures With Sub-Micrometer Dimensions," Adv. Mater., vol. 7, No. 7, pp. 649-652, 1995.

Wilm, Matthias et al., "Femtomole Sequencing of Proteins From Polyacrylamide Gels by Nano-Electrospray Mass Spectrometry," Nature, vol. 379, pp. 466-469, Feb. 1, 1996.

Wu, Chunhung et al., "Viscosity-Adjustable Block Copolymer for DNA Separation by Capillary Electrophoresis," Electrophoresis, vol. 19, pp. 231-241, 1998.

Wu, Hongkai et al., "Fabrication of Complex Three-Dimensional Microchannel Systems in PDMS," J. Am. Chem. Soc., vol. 125, No. 2, pp. 554-559, 2003.

Xia, Younan et al., "Complex Optical Surfaces Formed by Replica Molding Against Elastomeric Masters," Science, vol. 273, pp. 347-349, Jul. 19, 1996.

Xia, Younan et al., "Micromolding of Polymers in Capillaries: Applications in Microfabrication," Chem. Mater., vol. 8, No. 7, pp. 1559-1566, 1996.

Xia, Younan et al., "Reduction in the Size of Features of Patterned SAMs Generated by Microcontact Printing With Mechanical Compression of the Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures by Soft Lithography," Adv. Mater., vol. 11, No. 14, pp. 1186-1189, 1999.

Xu, Jingdong et al., "Room-Temperature Imprinting Method for Plastic Microchannel Fabrication," Analytical Chemistry, vol. 72, No. 8, pp. 1930-1933, Apr. 15, 2000.

Xu, Xiang et al., "Detection of Programmed Cell Death Using Fluorescence Energy Transfer," Nucleic Acids Research, vol. 26, No. 8, pp. 2034-2035, 1998.

Xue, Qifeng et al., "Integrated Multichannel Microchip Electrospray Ionization Mass Spectrometry: Analysis of Peptides From On-Chip Tryptic Digestion of Melittin," Rapid Communcation in Mass Spectrometry, vol. 11, 1253-1256, 1997.

Xue, Qifeng et al., "Multichannel Microchip Electrospray Mass Spectrometry," Analytical Chemistry, vol. 69, No. 3, pp. 426-430, Feb. 1, 1997.

Yang, T. J. et al., "An Apertureless Near-Field Microscope for Fluorescence Imaging," Applied Physics Letters, vol. 76, No. 3, pp. 378-380, Jan. 17, 2000.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoys, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Yokobayashi, Yohei et al., "Evolutionary Design of Genetic Circuits and Cell-Cell Communications," Advances in Complex Systems, vol. 6, No. 1, pp. 37-45, 2003.

Young, A. M. et al., "Contoured Elastic-Membrane Microvalves for Microfluidic Network Integration," Journal of Biomechanical Engineering, vol. 121, pp. 2-6, Feb. 1999.

Zaccolo, Manuela et al., "Genetically Encoded, Fluorescent Indicator for Cyclic AMP in Living Cells," Nature Cell Biology, vol. 2, pp. 25-29, Jan. 2000.

Zalipsky, Samuel, "Chemistry of Polyethyelene Glycol Conjugates With Biologically Active Molecules," Advanced Drug Delivery Reviews, vol. 16, pp. 157-182, 1995.

Zdeblick, Mark J. et al., "A Microminiature Electric-To-Fluidic Valve," Transducers '87, Proceedings of the 4th International Conference on Solid-State Sensors and Actuators, reprinted in Micromechanics and MEMS Classic and Seminal Papers to 1990, pp. 2 cover pages, 437-439, Jun. 1987.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation of Microminiaturized Membrane Pumps," 7th International Conference on Solid-State Sensors and Actuators, Yokohama, Japan, pp. 2 cover pages, 105-109, Jun. 7-10, 1993

Zhang, B. et al., "Microfabricated Devices for Capillary Electrophoresis-Electrospray Mass Spectrometry," Analytical Chemistry, vol. 71, No. 15, pp. 3258-3264, Aug. 1, 1999.

Zhao, Zhan, et al., "An Integrated Biochip Design and Fabrication," Proceedings of SPIE, vol. 4936, pp. 321-326, 2002.

Zheng, Bo et al., "A Droplet-Based, Composite PDMS/Glass Capillary Microfluidic System for Evaluating Protein Crystallization Conditions by Microbatch and Vapor-Diffusion Methods with On-Chip-X-Ray Diffraction," Angew, Chem., pp. 1-4, 2004.

Busch, J. et al., Methods for the Differentiation of Microorganisms, Journal of Chromatography B, vol. 722, pp. 263-278, 1999.

Jacobson, Ken et al., "International Workshop on the Application of Fluoroscence Photobleaching Techniques to Problems in Cell Biology," Federation Proceedings, vol. 42, No. 1, pp. 72-79, Jan. 1983.

Volkmuth, W. D. et al., "DNA Electrodiffusion in a 2D Array of Posts," Physical Revier Letters, vol. 72, No. 13, pp. 2117-2120, Mar. 28, 1994.

* cited by examiner

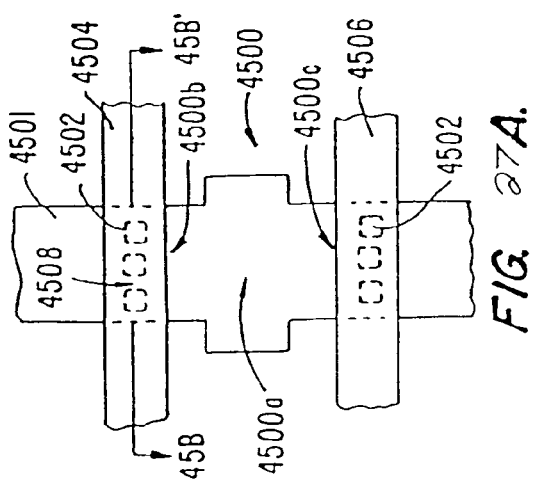
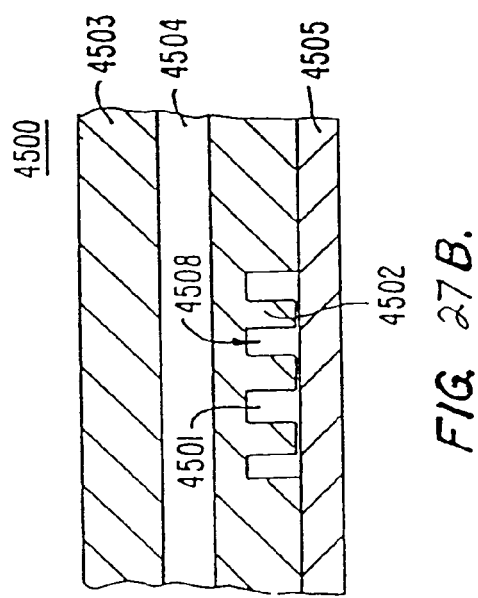
FIG. 27A.
FIG. 27B.

leads ①④ as source, drain
leads ②③ as sensing leads to voltage measurement

METHODS AND DEVICES FOR ELECTRONIC AND MAGNETIC SENSING OF THE CONTENTS OF MICROFLUIDIC FLOW CHANNELS

CROSS-REFERENCE TO RELATED APPLICATION

This application is a continuation of U.S. patent application Ser. No. 10/273,406, entitled "METHODS AND DEVICES FOR ELECTRONIC AND MAGNETIC SENSING OF THE CONTENTS OF MICROFLUIDIC FLOW CHANNELS," filed Oct. 16, 2002 by Hany Nassef et al., now abandoned ("the '406 application"). The '406 application is a nonprovisional of, and claims the benefit of the filing date of, U.S. Prov. Pat. Appl. No. 60/348,448, filed Oct. 26, 2001. Both the foregoing applications are incorporated herein by reference in their entireties for all purposes.

BACKGROUND OF THE INVENTION

U.S. patent application Ser. No. 09/605,520 ("the '520 application") describes in detail the use of elastomeric materials to fabricate microfluidic structures. The '520 application is hereby incorporated by reference in its entirety for all purposes.

The microfabricated elastomeric structures disclosed in the '520 application may be employed for a wide variety of purposes. One application for which these structures are particularly suited is sorting. In a sorting structure, a sample containing a sortable entity is flowed down a flow channel to a detection region, such that only one sortable entity may be located within the detection region at a time. The detection region is then interrogated to identify the sortable entity. The sortable entity is then flowed to a junction, and then down one or another branch at the junction based upon the identification process.

As described in the '520 application, the width of the flow channels may be defined utilizing photolithographic techniques conventionally employed in semiconductor fabrication processes. Accordingly, the dimensions of the flow channels may extremely small (<1 µm), allowing for sorting of entities on the cellular or molecular scale.

One of the most important steps of a sorting process is the accurate detection and identification of an entity prior to its sorting. This detection/identification task is made more difficult when the entity is extremely small.

Accordingly, there is a need in the art for methods and structures for detecting and identifying the contents of the extremely narrow flow channels of microfluidic devices.

BRIEF SUMMARY OF THE INVENTION

The presence of a detectable entity within a detection region of a microfabricated elastomeric structure is detected through a change in the electrical or magnetic environment of the detection region. In embodiments utilizing electronic detection, an electric field is applied to the detection region and a change in impedance or current due to the presence of the detectable entity is measured. In embodiments utilizing magnetic detection, the magnetic properties of a detected entity alter the magnetic field of the detection volume and can be sensed by induced currents, changed electric fields, or changes in the behavior of magnetoresistive elements.

An embodiment of a method of detecting an entity in a microfabricated elastomeric structure comprises providing a microfabricated elastomeric structure including a flow channel and a deflectable elastomeric membrane. Defined within the flow channel is a detection volume receiving one detectable entity or an ensemble of detected entities at a time. An electric field is applied to the detection volume, and a change is measured in one of a voltage across and a current through the detection volume as the detectable entity traverses the detection volume.

An embodiment of a method of detecting an entity in a microfabricated elastomeric structure comprises providing the microfabricated elastomeric structure including a flow channel and a deflectable elastomeric membrane. A detection volume is defined within the flow channel, the detection volume receiving one magnetized detectable entity or an ensemble of magnetized detected entities at a time. A conductive coil is provided proximate to the detection volume, and a current induced in the coil structure by passage of the magnetized detectable entity through the detection volume is measured.

An embodiment of a microfabricated elastomeric structure in accordance with the present invention comprises a flow channel formed in an elastomeric material. A control recess overlies and is separated from the flow channel by an elastomeric membrane deflectable into the flow channel. A detection volume is defined within the flow channel to receive one detectable entity or ensemble of detected entities at a time. A first electrode and a second electrode formed in the elastomer material are in communication with a power supply and configured to apply an electric field to the detection volume.

These and other embodiments of the present invention, as well as its advantages and features, are described in more detail in conjunction with the text below and attached figures.

BRIEF DESCRIPTION OF THE DRAWINGS

FIGS. 27A-27B show plan and cross-sectional views illustrating operation of one embodiment of a cell cage structure in accordance with the present invention.

DETAILED DESCRIPTION OF THE INVENTION

I. Microfabrication Overview

The following discussion relates to formation of microfabricated fluidic devices utilizing elastomer materials, as described generally in U.S. patent application Ser. Nos. 09/826,585 filed Apr. 6, 2001, 09/724,784 filed Nov. 28, 2000, and 09/605,520, filed Jun. 27, 2000. These patent applications are hereby incorporated by reference.

1. Methods of Fabricating

Exemplary methods of fabricating the present invention are provided herein. It is to be understood that the present invention is not limited to fabrication by one or the other of these methods. Rather, other suitable methods of fabricating the present microstructures, including modifying the present methods, are also contemplated.

FIGS. 1 to 7B illustrate sequential steps of a first preferred method of fabricating the present microstructure, (which may be used as a pump or valve). FIGS. 8 to 18 illustrate sequential steps of a second preferred method of fabricating the present microstructure, (which also may be used as a pump or valve).

As will be explained, the preferred method of FIGS. 1 to 7B involves using pre-cured elastomer layers which are assembled and bonded. In an alternative method, each layer of elastomer may be cured "in place". In the following description "channel" refers to a recess in the elastomeric structure which can contain a flow of fluid or gas.

Figure 1:
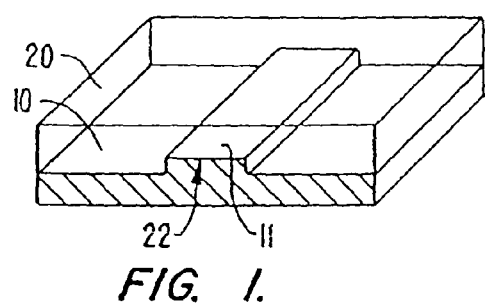
FIG. 1 is an illustration of a first elastomeric layer formed on top of a micromachined mold.

Referring to FIG. 1, a first micro-machined mold 10 is provided. Micro-machined mold 10 may be fabricated by a number of conventional silicon processing methods, including but not limited to photolithography, ion-milling, and electron beam lithography.

As can be seen, micro-machined mold 10 has a raised line or protrusion 11 extending therealong. A first elastomeric layer 20 is cast on top of mold 10 such that a first recess 21 will be formed in the bottom surface of elastomeric layer 20, (recess 21 corresponding in dimension to protrusion 11), as shown.

Figure 2:
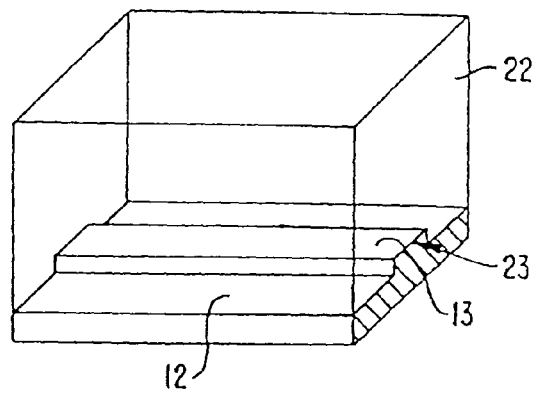
FIG. 2 is an illustration of a second elastomeric layer formed on top of a micromachined mold.

As can be seen in FIG. 2, a second micro-machined mold 12 having a raised protrusion 13 extending therealong is also provided. A second elastomeric layer 22 is cast on top of mold 12, as shown, such that a recess 23 will be formed in its bottom surface corresponding to the dimensions of protrusion 13.

Figure 3:
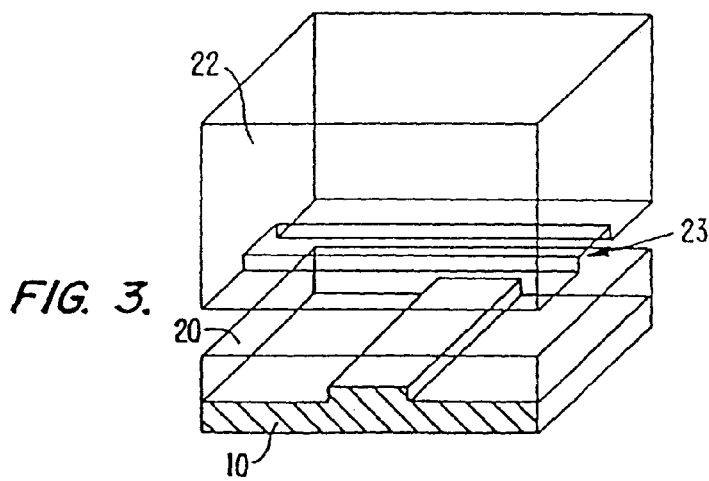
FIG. 3 is an illustration of the elastomeric layer of FIG. 2 removed from the micromachined mold and positioned over the top of the elastomeric layer of FIG. 1
Figure 4:
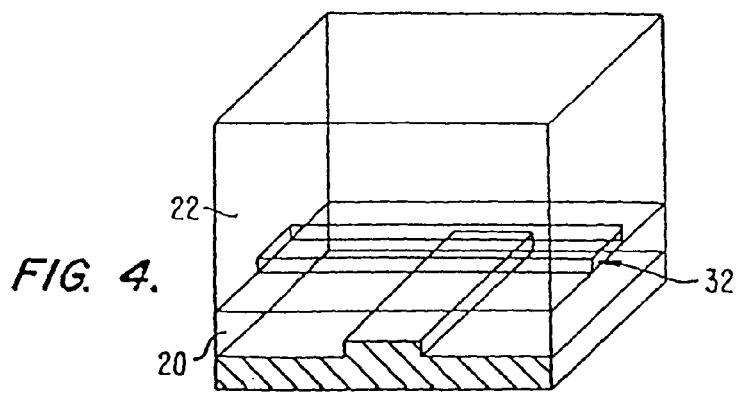
FIG. 4 is an illustration corresponding to FIG. 3, but showing the second elastomeric layer positioned on top of the first elastomeric layer.

As can be seen in the sequential steps illustrated in FIGS. 3 and 4, second elastomeric layer 22 is then removed from mold 12 and placed on top of first elastomeric layer 20. As can be seen, recess 23 extending along the bottom surface of second elastomeric layer 22 will form a flow channel 32.

Figure 5:
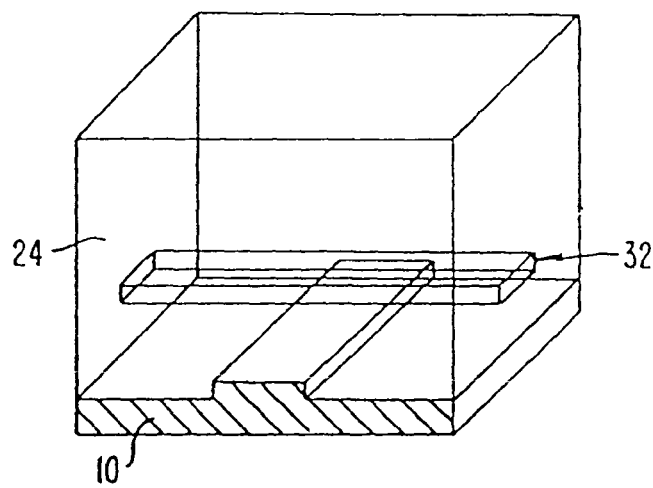
FIG. 5 is an illustration corresponding to FIG. 4, but showing the first and second elastomeric layers bonded together.

Referring to FIG. 5, the separate first and second elastomeric layers 20 and 22 (FIG. 4) are then bonded together to form an integrated (i.e.: monolithic) elastomeric structure 24.

Figure 6:
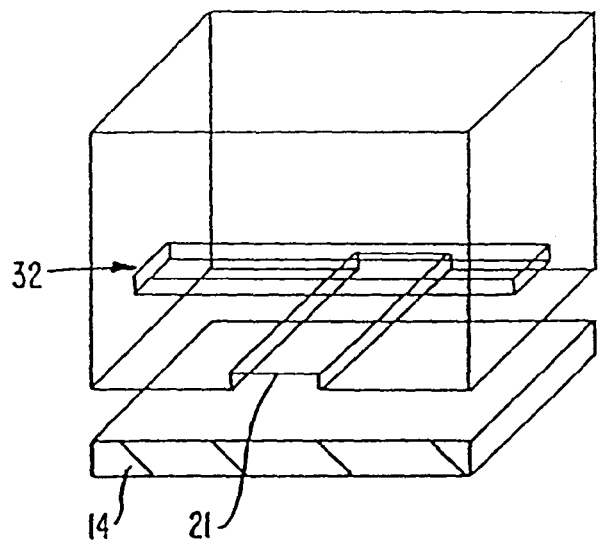
FIG. 6 is an illustration corresponding to FIG. 5, but showing the first micromachined mold removed and a planar substrate positioned in its place.
Figure 7A:
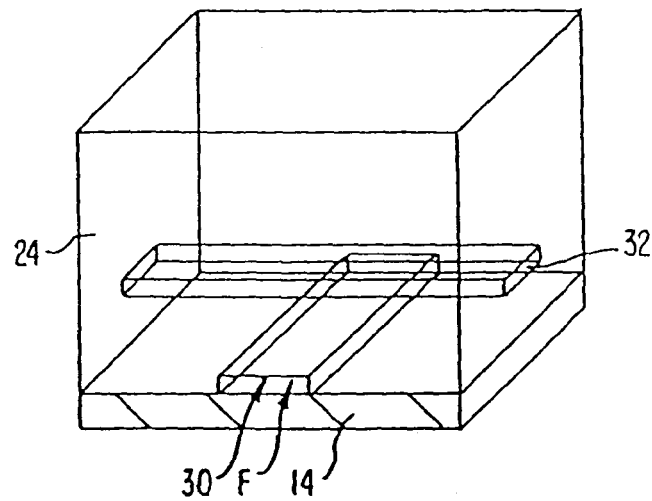
FIG. 7A is an illustration corresponding to FIG. 6, but showing the elastomeric structure sealed onto the planar substrate.
Figure 7B:
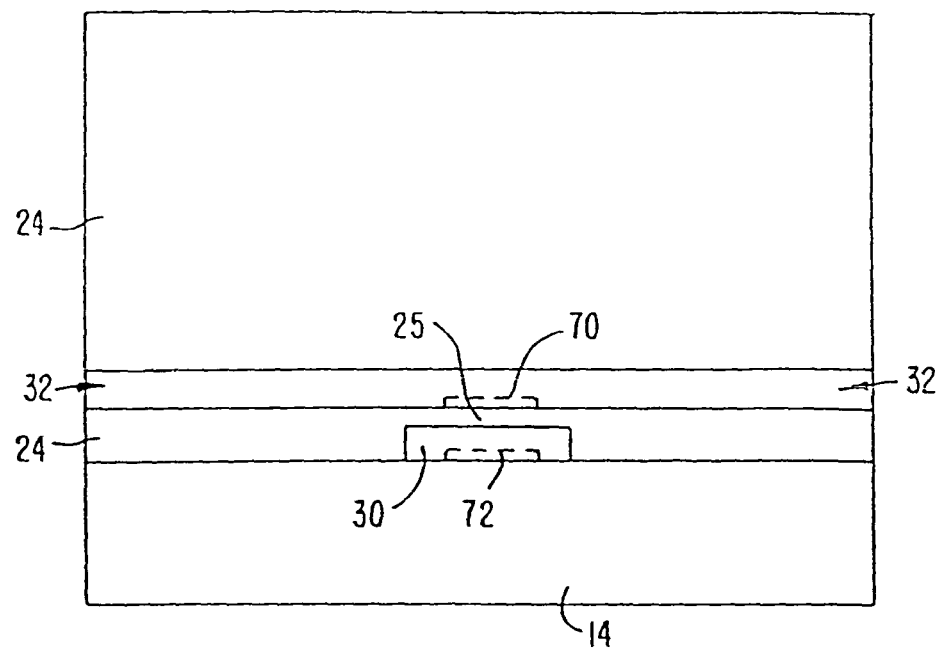
FIG. 7B is a front sectional view corresponding to FIG. 7A, showing an open flow channel.

As can been seen in the sequential step of FIGS. 6 and 7A, elastomeric structure 24 is then removed from mold 10 and positioned on top of a planar substrate 14. As can be seen in FIGS. 7A and 7B, when elastomeric structure 24 has been sealed at its bottom surface to planar substrate 14, recess 21 will form a flow channel 30.

The present elastomeric structures form a reversible hermetic seal with nearly any smooth planar substrate. An advantage to forming a seal this way is that the elastomeric structures may be peeled up, washed, and re-used. In preferred aspects, planar substrate 14 is glass. A further advantage of using glass is that glass is transparent, allowing optical interrogation of elastomer channels and reservoirs. Alternatively, the elastomeric structure may be bonded onto a flat elastomer layer by the same method as described above, forming a permanent and high-strength bond. This may prove advantageous when higher back pressures are used.

As can be seen in FIGS. 7A and 7B, flow channels 30 and 32 are preferably disposed at an angle to one another with a small membrane 25 of substrate 24 separating the top of flow channel 30 from the bottom of flow channel 32.

In preferred aspects, planar substrate 14 is glass. An advantage of using glass is that the present elastomeric structures may be peeled up, washed and reused. A further advantage of using glass is that optical sensing may be employed. Alternatively, planar substrate 14 may be an elastomer itself, which may prove advantageous when higher back pressures are used.

The method of fabrication just described may be varied to form a structure having a membrane composed of an elastomeric material different than that forming the walls of the channels of the device. This variant fabrication method is illustrated in FIGS. 7C-7G.

Figure 7H:
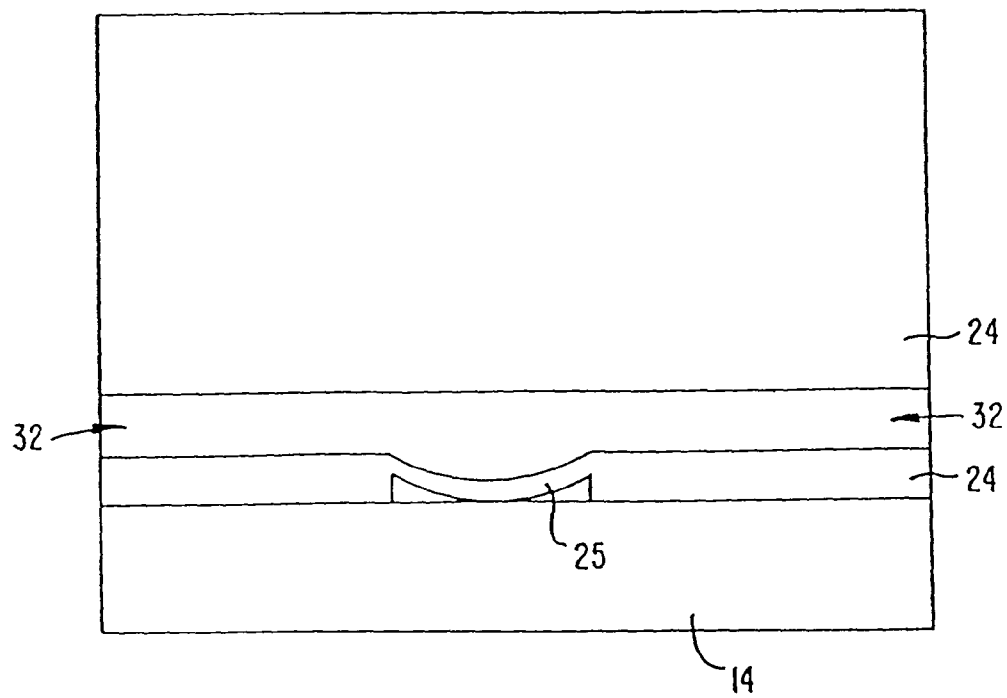
FIG. 7H together shows the closing of a first flow channel by pressurizing a second flow channel.
Figure 7C:
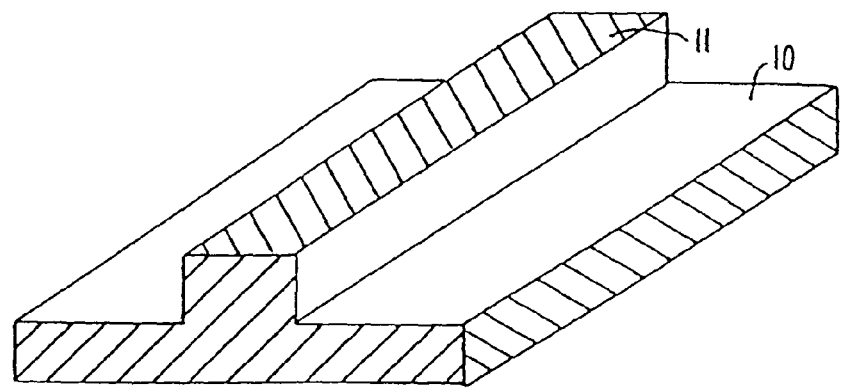
FIGS. 7C-7G are illustrations showing steps of a method for forming an elastomeric structure having a membrane formed from a separate elastomeric layer.
Figure 7D:
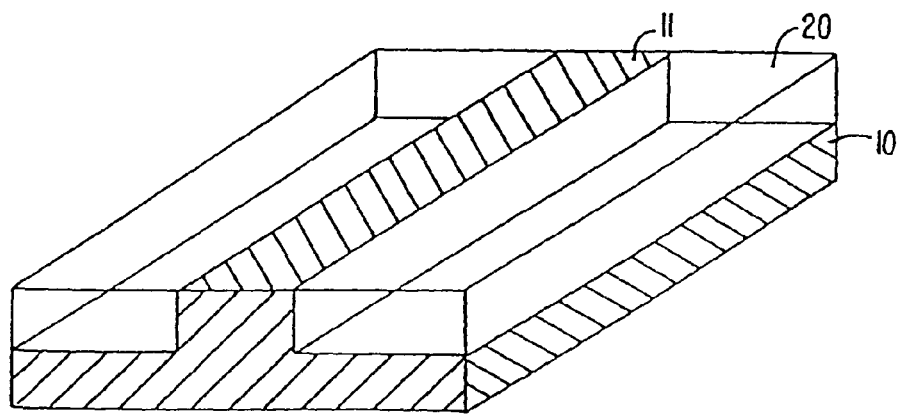

Referring to FIG. 7C, a first micro-machined mold 10 is provided. Micro-machined mold 10 has a raised line or protrusion 11 extending therealong. In FIG. 7D, first elastomeric layer 20 is cast on top of first micro-machined mold 10 such that the top of the first elastomeric layer 20 is flush with the top of raised line or protrusion 11. This may be accomplished by carefully controlling the volume of elastomeric material spun onto mold 10 relative to the known height of raised line 11. Alternatively, the desired shape could be formed by injection molding.

Figure 7E:
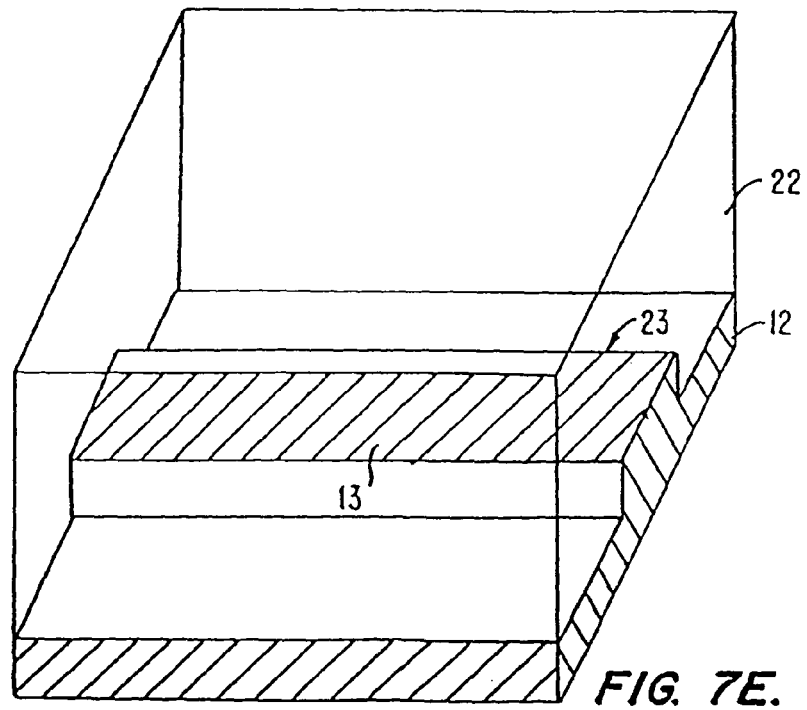

In FIG. 7E, second micro-machined mold 12 having a raised protrusion 13 extending therealong is also provided. Second elastomeric layer 22 is cast on top of second mold 12 as shown, such that recess 23 is formed in its bottom surface corresponding to the dimensions of protrusion 13.

Figure 7F:
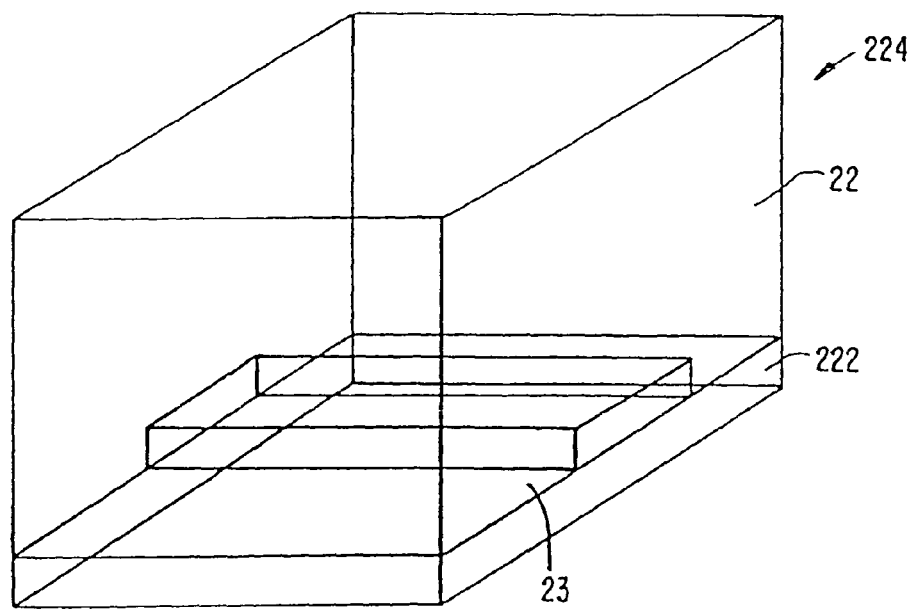

In FIG. 7F, second elastomeric layer 22 is removed from mold 12 and placed on top of third elastomeric layer 222. Second elastomeric layer 22 is bonded to third elastomeric layer 20 to form integral elastomeric block 224 using techniques described in detail below. At this point in the process, recess 23 formerly occupied by raised line 13 will form flow channel 23.

Figure 7G:
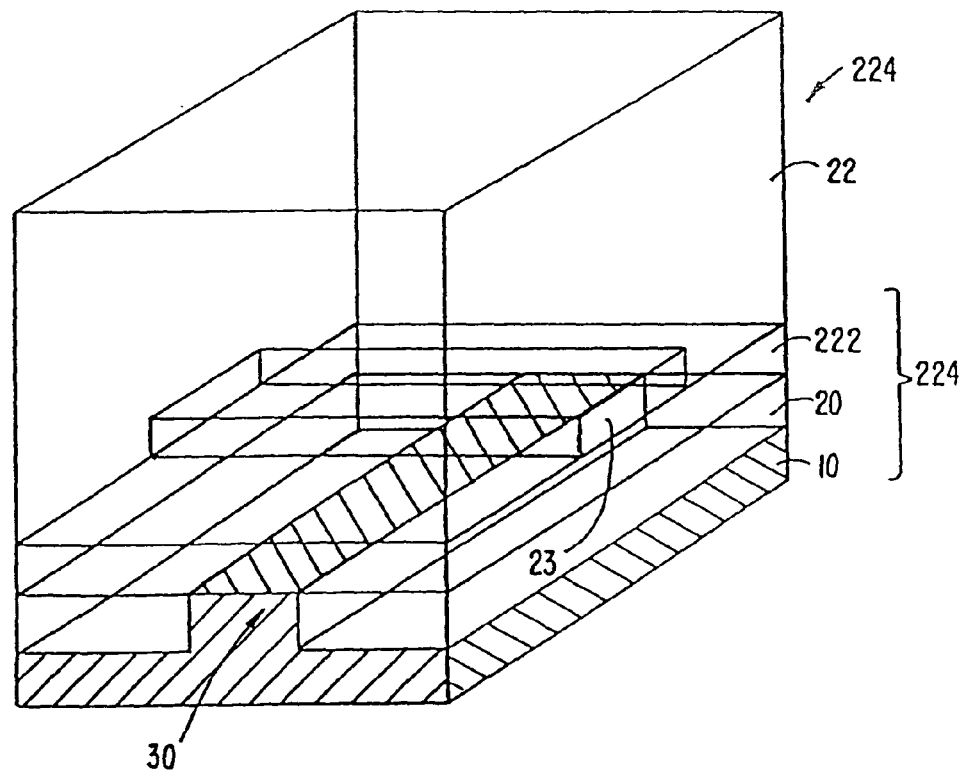

In FIG. 7G, elastomeric block 224 is placed on top of first micro-machined mold 10 and first elastomeric layer 20. Elastomeric block and first elastomeric layer 20 are then bonded together to form an integrated (i.e.: monolithic) elastomeric structure 24 having a membrane composed of a separate elastomeric layer 222.

When elastomeric structure 24 has been sealed at its bottom surface to a planar substrate in the manner described above in connection with FIG. 7A, the recess formerly occupied by raised line 11 will form flow channel 30.

The variant fabrication method illustrated above in conjunction with FIGS. 7C-7G offers the advantage of permitting the membrane portion to be composed of a separate material than the elastomeric material of the remainder of the structure. This is important because the thickness and elastic properties of the membrane play a key role in operation of the device. Moreover, this method allows the separate elastomer layer to readily be subjected to conditioning prior to incorporation into the elastomer structure. As discussed in detail below, examples of potentially desirable condition include the introduction of magnetic or electrically conducting species to permit actuation of the membrane, and/or the introduction of dopant into the membrane in order to alter its elasticity.

While the above method is illustrated in connection with forming various shaped elastomeric layers formed by replication molding on top of a micromachined mold, the present invention is not limited to this technique. Other techniques could be employed to form the individual layers of shaped elastomeric material that are to be bonded together. For example, a shaped layer of elastomeric material could be formed by laser cutting or injection molding, or by methods utilizing chemical etching and/or sacrificial materials as discussed below in conjunction with the second exemplary method.

An alternative method fabricates a patterned elastomer structure utilizing development of photoresist encapsulated within elastomer material. However, the methods in accordance with the present invention are not limited to utilizing photoresist. Other materials such as metals could also serve as sacrificial materials to be removed selective to the surrounding elastomer material, and the method would remain within the scope of the present invention. For example, gold metal may be etched selective to RTV 615 elastomer utilizing the appropriate chemical mixture.

2. Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 μm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels 30, 32, 60 and 62 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 μm, 1 μm, 2 μm, 5 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, and 250 μm.

Flow channels 30, 32, 60, and 62 have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 μm, 0.02 μm, 0.05 μm, 0.1 μm, 0.2 μm, 0.5 μm, 1 μm, 2 μm, 3 μm, 4 μm, 5 μm, 7.5 μm, 10 μm, 12.5 μm, 15 μm, 17.5 μm, 20 μm, 22.5 μm, 25 μm, 30 μM, 40 μm, 50 μm, 75 μM, 100 μm, 150 μm, 200 μm, and 250 μm.

The flow channels are not limited to these specific dimension ranges and examples given above, and may vary in width in order to affect the magnitude of force required to deflect the membrane as discussed at length below in conjunction with FIG. 27. For example, extremely narrow flow channels having a width on the order of 0.01 μm may be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

The Elastomeric layers may be cast thick for mechanical stability. In an exemplary embodiment, elastomeric layer 22 of FIG. 1 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 7B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 μm, 0.02 μm, 0.03 μm, 0.05 μm, 0.1 μm, 0.2 μm, 0.3 μm, 0.5 μm, 1 μm, 2 μm, 3 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, 250 μm, 300 μm, 400 μm, 500 μm, 750 μm, and 1000 μm.

3. Soft Lithographic Bonding

Preferably, elastomeric layers are bonded together chemically, using chemistry that is intrinsic to the polymers comprising the patterned elastomer layers. Most preferably, the bonding comprises two component "addition cure" bonding.

In a preferred aspect, the various layers of elastomer are bound together in a heterogenous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

In one embodiment in accordance with the present invention, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolyte corporation. The assembled layers were then cured for an additional 30 minutes. Reaction was catalyzed by a 0.5% vol./vol. mixture of Irgacure 500 manufactured by Ciba-Geigy Chemicals. The resulting elastomeric material exhibited moderate elasticity and adhesion to glass.

In another embodiment in accordance with the present invention, two-layer elastomeric structures were fabricated from a combination of 25% Ebe 270/50% Irr 245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolyte corporation. The assembled layers were then cured for an additional 30 minutes. Reaction was catalyzed by a 0.5% vol./vol. mixture of Irgacure 500 manufactured by Ciba-Geigy Chemicals. The resulting elastomeric material exhibited moderate elasticity and adhered to glass.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly (dimethylsiloxane)", *Analytical Chemistry* (1998), 70, 4974-4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Referring to the first method of FIGS. 1 to 7B, first elastomeric layer 20 may be created by spin-coating an RTV mixture on microfabricated mold 12 at 2000 rpm's for 30 seconds yielding a thickness of approximately 40 microns. Second elastomeric layer 22 may be created by spin-coating an RTV mixture on microfabricated mold 11. Both layers 20 and 22 may be separately baked or cured at about 80° C. for 1.5 hours. The second elastomeric layer 22 may be bonded onto first elastomeric layer 20 at about 80° C. for about 1.5 hours.

Micromachined molds 10 and 12 may be patterned photoresist on silicon wafers. In an exemplary aspect, a Shipley SJR 5740 photoresist was spun at 2000 rpm patterned with a high resolution transparency film as a mask and then developed yielding an inverse channel of approximately 10 microns in height. When baked at approximately 200° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

4. Suitable Elastomeric Materials

Allcock et al, Contemporary *Polymer Chemistry*, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

The systems of the present invention may be fabricated from a wide variety of elastomers. In an exemplary aspect, the elastomeric layers may preferably be fabricated from silicone rubber. However, other suitable elastomers may also be used.

In an exemplary aspect of the present invention, the present systems are fabricated from an elastomeric polymer such as GE RTV 615 (formulation), a vinyl-silane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, polybutadiene, polychloroprene:

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene:

Pure polyisobutylene has no double bonds, but is crosslinked to use as an elastomer by including a small amount (~1%) of isoprene in the polymerization. The isoprene monomers give pendant double bonds on the polyisobutylene backbone, which may then be vulcanized as above.

Poly(styrene-butadiene-styrene):

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethane's:

Polyurethane's are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones:

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

5. Operation of Device

FIGS. 7B and 7H together show the closing of a first flow channel by pressurizing a second flow channel, with FIG. 7B (a front sectional view cutting through flow channel 32 in corresponding FIG. 7A), showing an open first flow channel 30; with FIG. 7H showing first flow channel 30 closed by pressurization of the second flow channel 32.

Referring to FIG. 7B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 7H, pressurization of flow channel 32 (either by gas or liquid introduced therein) causes membrane 25 to deflect downward, thereby pinching off flow F passing through flow channel 30. Accordingly, by varying the pressure in channel 32, a linearly actuable valving system is provided such that flow channel 30 can be opened or closed by moving membrane 25 as desired. (For illustration purposes only, channel 30 in FIG. 7G is shown in a "mostly closed" position, rather than a "fully closed" position).

Since such valves are actuated by moving the roof of the channels themselves (i.e.: moving membrane 25) valves and pumps produced by this technique have a truly zero dead volume, and switching valves made by this technique have a dead volume approximately equal to the active volume of the valve, for example about 100×100×10 μm=100 pL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 uL, 100 aL to 100 mL, 1 fL to 10 mL, 100 fL to 1 mL, and 1 pL to 100 pL The extremely small volumes capable of being delivered by pumps and valves in accordance with the present invention represent a substantial advantage. Specifically, the smallest known volumes of fluid capable of being manually metered is around 0.1 μl. The smallest known volumes capable of being metered by automated systems is about ten-times larger (1 μl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$$w=(BPb^4)/(Eh^3), \tag{1}$$

where:
 $w$=deflection of plate;
 $B$=shape coefficient (dependent upon length vs. width and support of edges of plate);
 $P$=applied pressure;
 $b$=plate width
 $E$=Young's modulus; and
 $h$=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticities, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

Figure 8A:
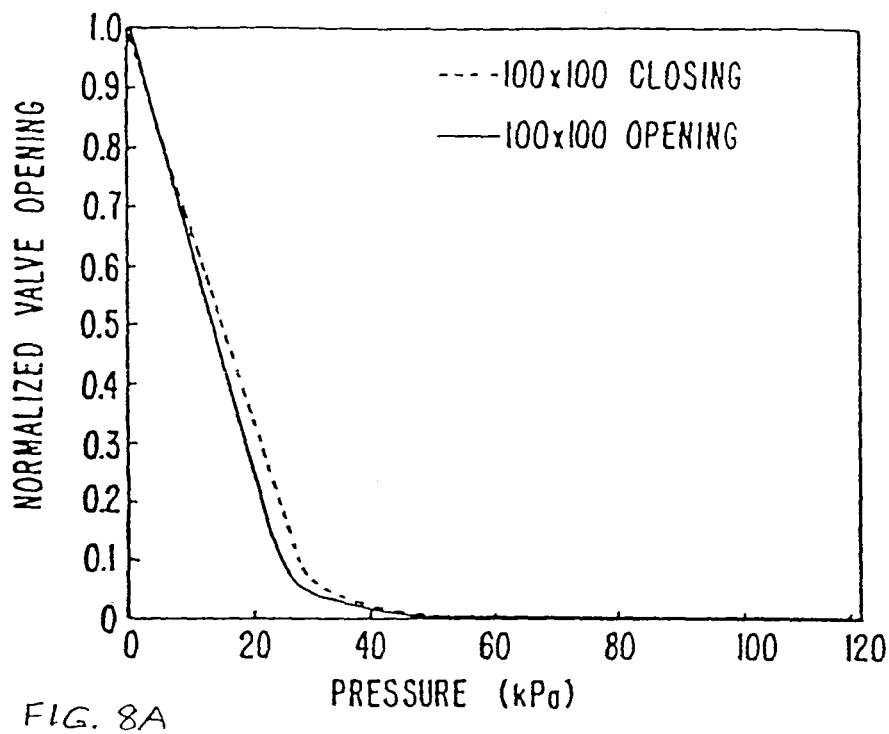
FIGS. 8A and 8B illustrates valve opening vs. applied pressure for various flow channels.
Figure 8B:
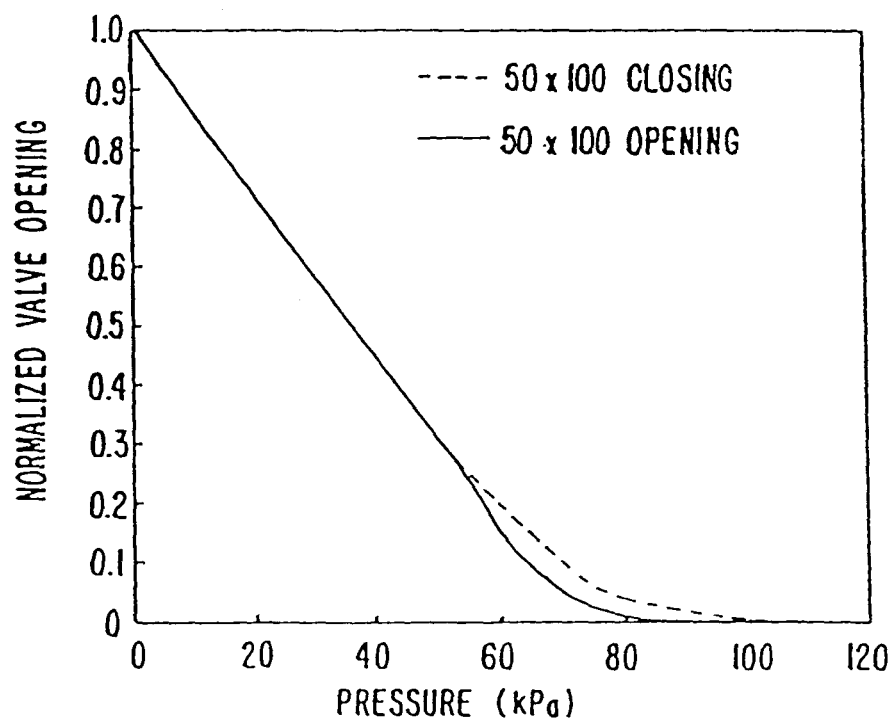
Figure 21A:
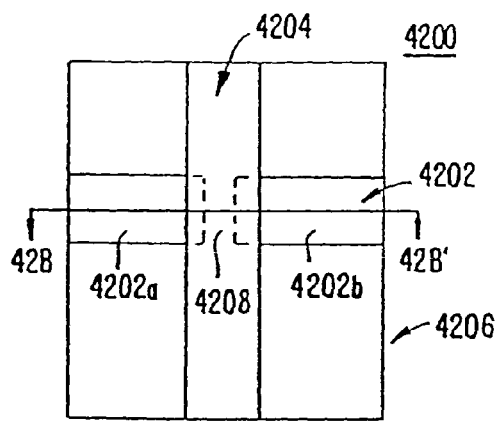
FIGS. 21A-21J show views of one embodiment of a normally-closed valve structure in accordance with the present invention.

FIGS. 8A and 8B illustrate valve opening vs. applied pressure for a 100 μm wide first flow channel 30 and a 50 μm wide second flow channel 32. The membrane of this device was formed by a layer of General Electric Silicones RTV 615 having a thickness of approximately 30 μm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

While control of the flow of material through the device has so far been described utilizing applied gas pressure, other fluids could be used.

For example, air is compressible, and thus experiences some finite delay between the time of application of pressure by the external solenoid valve and the time that this pressure is experienced by the membrane. In an alternative embodiment of the present invention, pressure could be applied from an external source to a noncompressible fluid such as water or hydraulic oils, resulting in a near-instantaneous transfer of applied pressure to the membrane. However, if the displaced volume of the valve is large or the control channel is narrow, higher viscosity of a control fluid may contribute to delay in actuation. The optimal medium for transferring pressure will therefore depend upon the particular application and device configuration, and both gaseous and liquid media are contemplated by the invention.

While external applied pressure as described above has been applied by a pump/tank system through a pressure regulator and external miniature valve, other methods of applying external pressure are also contemplated in the present invention, including gas tanks, compressors, piston systems, and columns of liquid. Also contemplated is the use of naturally occurring pressure sources such as may be found inside living organisms, such as blood pressure, gastric pressure, the pressure present in the cerebro-spinal fluid, pressure present in the intra-ocular space, and the pressure exerted by muscles during normal flexure. Other methods of regulating external pressure are also contemplated, such as miniature valves, pumps, macroscopic peristaltic pumps, pinch valves, and other types of fluid regulating equipment such as is known in the art.

As can be seen, the response of valves in accordance with embodiments of the present invention have been experimentally shown to be almost perfectly linear over a large portion of its range of travel, with minimal hysteresis. Accordingly, the present valves are ideally suited for microfluidic metering and fluid control. The linearity of the valve response demonstrates that the individual valves are well modeled as Hooke's Law springs. Furthermore, high pressures in the flow channel (i.e.: back pressure) can be countered simply by increasing the actuation pressure. Experimentally, the present inventors have achieved valve closure at back pressures of 70 kPa, but higher pressures are also contemplated. The following is a nonexclusive list of pressure ranges encompassed by the present invention: 10 Pa-25 MPa; 100 Pa-10 Mpa, 1 kPa-1 MPa, 1 kPa-300 kPa, 5 kPa-200 kPa, and 15 kPa-100 kPa.

While valves and pumps do not require linear actuation to open and close, linear response does allow valves to more easily be used as metering devices. In one embodiment of the invention, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation may be easily determined from the pressure in the flow channel. If actuation is linear, increased pressure in the flow channel may be countered by adding the same pressure (force per unit area) to the actuated portion of the valve.

Linearity of a valve depends on the structure, composition, and method of actuation of the valve structure. Furthermore, whether linearity is a desirable characteristic in a valve depends on the application. Therefore, both linearly and non-linearly actuable valves are contemplated in the present invention, and the pressure ranges over which a valve is linearly actuable will vary with the specific embodiment.

Figure 9:
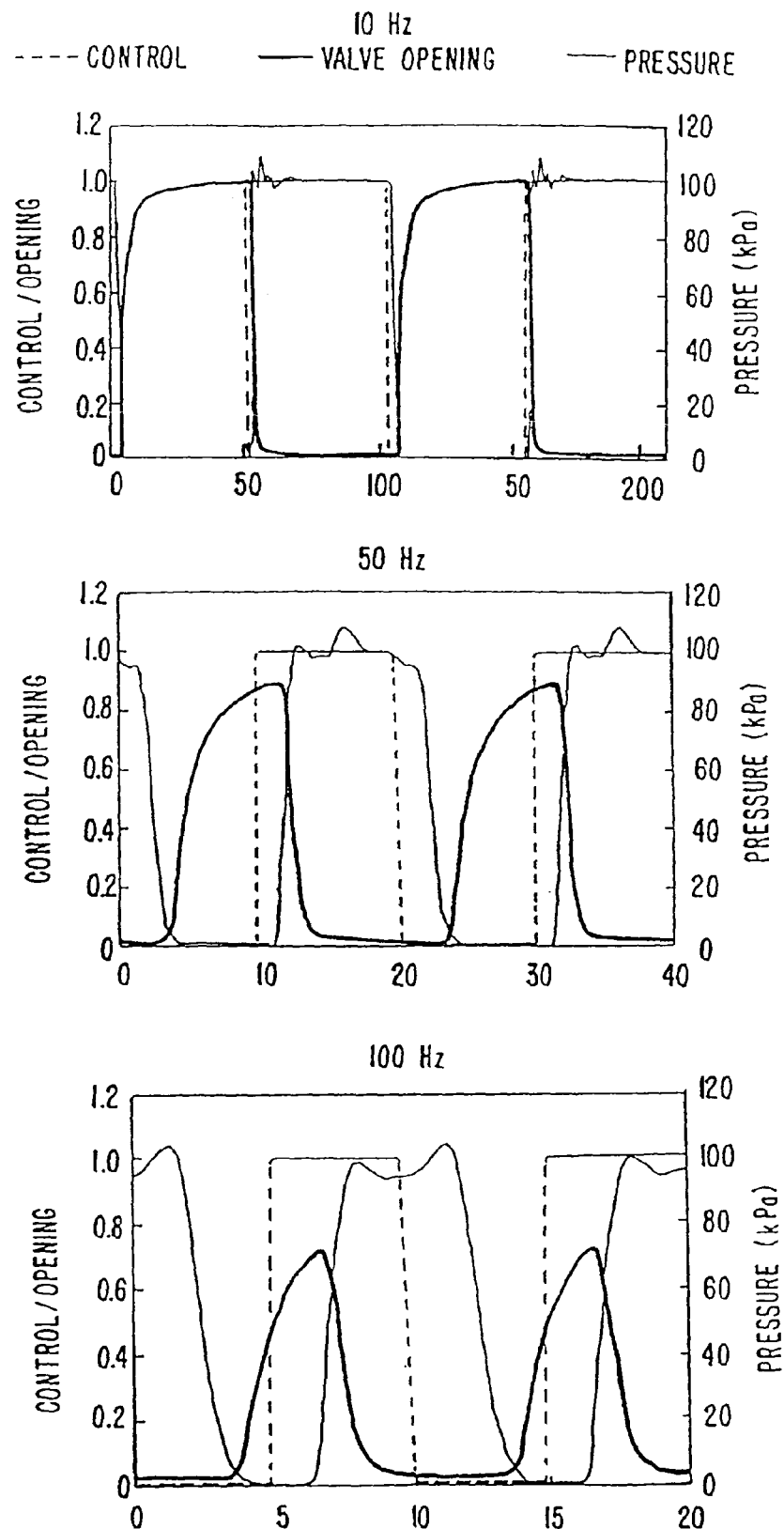
FIG. 9 illustrates time response of a 100 µm×100 µm×10 µm RTV microvalve.

FIG. 9 illustrates time response (i.e.: closure of valve as a function of time in response to a change in applied pressure) of a 100 µm×100 µm×10 µm RTV microvalve with 10-cm-long air tubing connected from the chip to a pneumatic valve as described above.

Two periods of digital control signal, actual air pressure at the end of the tubing and valve opening are shown in FIG. 9. The pressure applied on the control line is 100 kPa, which is substantially higher than the ~40 kPa required to close the valve. Thus, when closing, the valve is pushed closed with a pressure 60 kPa greater than required. When opening, however, the valve is driven back to its rest position only by its own spring force ($\leq 40$ kPa). Thus, $\tau_{close}$ is expected to be smaller than $\tau_{open}$. There is also a lag between the control signal and control pressure response, due to the limitations of the miniature valve used to control the pressure. Calling such lags t and the 1/e time constants τ, the values are: $t_{open}$=3.63 ms, $\tau_{open}$=1.88 ms, $t_{close}$=2.15 ms, $\tau_{close}$=0.51 ms. If 3τ each are allowed for opening and closing, the valve runs comfortably at 75 Hz when filled with aqueous solution.

If one used another actuation method which did not suffer from opening and closing lag, this valve would run at ~375 Hz. Note also that the spring constant can be adjusted by changing the membrane thickness; this allows optimization for either fast opening or fast closing. The spring constant could also be adjusted by changing the elasticity (Young's modulus) of the membrane, as is possible by introducing dopant into the membrane or by utilizing a different elastomeric material to serve as the membrane (described above in conjunction with FIGS. 7C-7H.)

When experimentally measuring the valve properties as illustrated in FIG. 9 the valve opening was measured by fluorescence. In these experiments, the flow channel was filled with a solution of fluorescein isothiocyanate (FITC) in buffer (pH 8) and the fluorescence of a square area occupying the center ~⅓ rd of the channel is monitored on an epi-fluorescence microscope with a photomultiplier tube with a 10 kHz bandwidth. The pressure was monitored with a Wheatstone-bridge pressure sensor (SenSym SCC15GD2) pressurized simultaneously with the control line through nearly identical pneumatic connections.

6. Flow Channel Cross Sections

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows.

Figure 10:
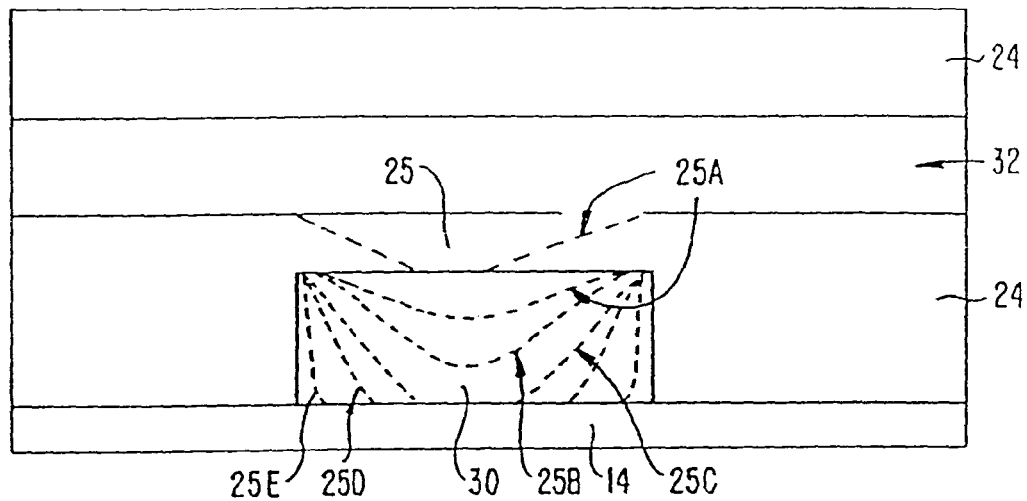
FIG. 10 is a cross sectional view of flow channel 30 which is rectangular in shape, being closed when flow channel 32 is pressurized.

Referring to FIG. 10, a cross sectional view (similar to that of FIG. 7B) through flow channels 30 and 32 is shown. As can be seen, flow channel 30 is rectangular in cross sectional shape. In an alternate preferred aspect of the invention, as shown in FIG. 20, the cross-section of a flow channel 30 instead has an upper curved surface.

Referring first to FIG. 10, when flow channel 32 is pressurized, the membrane portion 25 of elastomeric block 24 separating flow channels 30 and 32 will move downwardly to the successive positions shown by the dotted lines 25A, 25B, 25C, 25D, and 25E. As can be seen, incomplete sealing may possibly result at the edges of flow channel 30 adjacent planar substrate 14.

Figure 11:
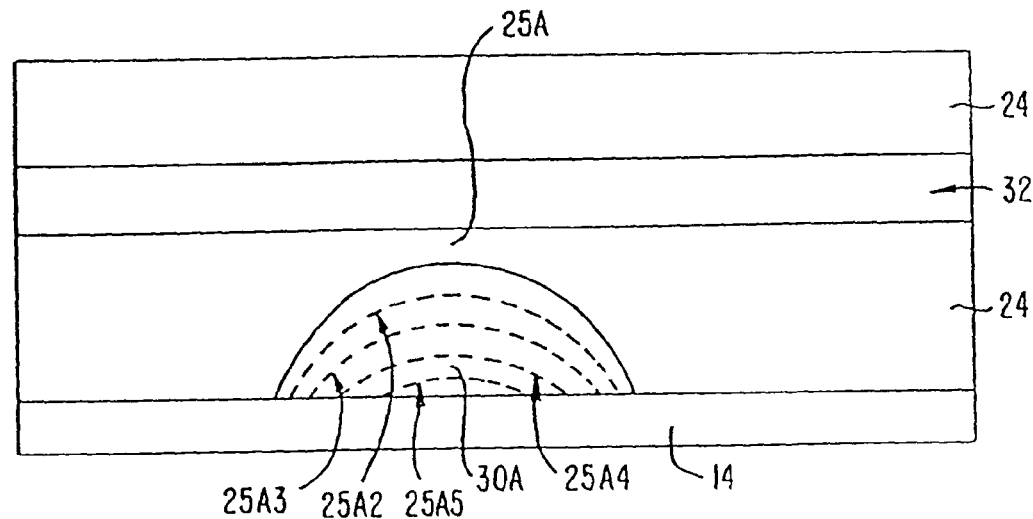
FIG. 11 shows flow channel 30A with a curved upper wall 25A. When flow channel 32 is pressurized, membrane portion 25A will move downward to produce a more complete seal.

In the alternate preferred embodiment of FIG. 11, flow channel 30a has a curved upper wall 25A. When flow channel 32 is pressurized, membrane portion 25 will move downwardly to the successive positions shown by dotted lines 25A2, 25A3, 25A4 and 25A5, with edge portions of the membrane moving first into the flow channel, followed by top membrane portions. An advantage of having such a curved upper surface at membrane 25A is that a more complete seal will be provided when flow channel 32 is pressurized. Specifically, the upper wall of the flow channel 30 will provide a continuous contacting edge against planar substrate 14, thereby avoiding the "island" of contact seen between wall 25 and the bottom of flow channel 30 in FIG. 10.

Another advantage of having a curved upper flow channel surface at membrane 25A is that the membrane can more readily conform to the shape and volume of the flow channel in response to actuation. Specifically, where a rectangular flow channel is employed, the entire perimeter (2× flow channel height, plus the flow channel width) must be forced into the flow channel. However where an arched flow channel is used, a smaller perimeter of material (only the semi-circular arched portion) must be forced into the channel. In this manner, the membrane requires less change in perimeter for actuation and is therefore more responsive to an applied actuation force to block the flow channel In an alternate aspect, (not illustrated), the bottom of flow channel 30 is rounded such that its curved surface mates with the curved upper wall 25A as seen in FIG. 20 described above.

In summary, the actual conformational change experienced by the membrane upon actuation will depend upon the configuration of the particular elastomeric structure. Specifically, the conformational change will depend upon the length, width, and thickness profile of the membrane, its attachment to the remainder of the structure, and the height, width, and shape of the flow and control channels and the material properties of the elastomer used. The conformational change may also depend upon the method of actuation, as actuation of the membrane in response to an applied pressure will vary somewhat from actuation in response to a magnetic or electrostatic force.

Moreover, the desired conformational change in the membrane will also vary depending upon the particular application for the elastomeric structure. In the simplest embodiments described above, the valve may either be open or closed, with metering to control the degree of closure of the valve. In other embodiments however, it may be desirable to alter the shape of the membrane and/or the flow channel in order to achieve more complex flow regulation. For instance, the flow channel could be provided with raised protrusions beneath the membrane portion, such that upon actuation the membrane shuts off only a percentage of the flow through the flow channel, with the percentage of flow blocked insensitive to the applied actuation force.

Many membrane thickness profiles and flow channel cross-sections are contemplated by the present invention, including rectangular, trapezoidal, circular, ellipsoidal, parabolic, hyperbolic, and polygonal, as well as sections of the above shapes. More complex cross-sectional shapes, such as the embodiment with protrusions discussed immediately above or an embodiment having concavities in the flow channel, are also contemplated by the present invention.

In addition, while the invention is described primarily above in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel. In general, monolithic elastomer structures as described elsewhere in the instant application are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

7. Alternate Valve Actuation Techniques

In addition to pressure based actuation systems described above, optional electrostatic and magnetic actuation systems are also contemplated, as follows.

Electrostatic actuation can be accomplished by forming oppositely charged electrodes (which will tend to attract one another when a voltage differential is applied to them) directly into the monolithic elastomeric structure. For example, referring to FIG. 7B, an optional first electrode 70 (shown in phantom) can be positioned on (or in) membrane 25 and an optional second electrode 72 (also shown in phantom) can be positioned on (or in) planar substrate 14. When electrodes 70 and 72 are charged with opposite polarities, an attractive force between the two electrodes will cause membrane 25 to deflect downwardly, thereby closing the "valve" (i.e.: closing flow channel 30).

For the membrane electrode to be sufficiently conductive to support electrostatic actuation, but not so mechanically stiff so as to impede the valve's motion, a sufficiently flexible electrode must be provided in or over membrane 25. Such an electrode may be provided by a thin metallization layer, doping the polymer with conductive material, or making the surface layer out of a conductive material.

In an exemplary aspect, the electrode present at the deflecting membrane can be provided by a thin metallization layer which can be provided, for example, by sputtering a thin layer of metal such as 20 nm of gold. In addition to the formation of a metallized membrane by sputtering, other metallization approaches such as chemical epitaxy, evaporation, electroplating, and electroless plating are also available. Physical transfer of a metal layer to the surface of the elastomer is also available, for example by evaporating a metal onto a flat substrate to which it adheres poorly, and then placing the elastomer onto the metal and peeling the metal off of the substrate.

A conductive electrode 70 may also be formed by depositing carbon black (i.e. Cabot Vulcan XC72R) on the elastomer surface, either by wiping on the dry powder or by exposing the elastomer to a suspension of carbon black in a solvent which causes swelling of the elastomer, (such as a chlorinated solvent in the case of PDMS). Alternatively, the electrode 70 may be formed by constructing the entire layer 20 out of elastomer doped with conductive material (i.e. carbon black or finely divided metal particles). Yet further alternatively, the electrode may be formed by electrostatic deposition, or by a chemical reaction that produces carbon. In experiments conducted by the present inventors, conductivity was shown to increase with carbon black concentration from $5.6 \times 10^{-16}$ to about $5 \times 10^{-3}$ $(\Omega\text{-cm})^{-1}$. The lower electrode 72, which is not required to move, may be either a compliant electrode as described above, or a conventional electrode such as evaporated gold, a metal plate, or a doped semiconductor electrode.

Magnetic actuation of the flow channels can be achieved by fabricating the membrane separating the flow channels with a magnetically polarizable material such as iron, or a permanently magnetized material such as polarized NdFeB. In experiments conducted by the present inventors, magnetic silicone was created by the addition of iron powder (about 1 um particle size), up to 20% iron by weight.

Where the membrane is fabricated with a magnetically polarizable material, the membrane can be actuated by attraction in response to an applied magnetic field Where the membrane is fabricated with a material capable of maintaining permanent magnetization, the material can first be magnetized by exposure to a sufficiently high magnetic field, and then actuated either by attraction or repulsion in response to the polarity of an applied in homogenous magnetic field.

The magnetic field causing actuation of the membrane can be generated in a variety of ways. In one embodiment, the magnetic field is generated by an extremely small inductive coil formed in or proximate to the elastomer membrane. The actuation effect of such a magnetic coil would be localized, allowing actuation of individual pump and/or valve structures. Alternatively, the magnetic field could be generated by a larger, more powerful source, in which case actuation would be global and would actuate multiple pump and/or valve structures at one time.

It is also possible to actuate the device by causing a fluid flow in the control channel based upon the application of thermal energy, either by thermal expansion or by production of gas from liquid. For example, in one alternative embodiment in accordance with the present invention, a pocket of fluid (e.g. in a fluid-filled control channel) is positioned over the flow channel. Fluid in the pocket can be in communication with a temperature variation system, for example a heater. Thermal expansion of the fluid, or conversion of material from the liquid to the gas phase, could result in an increase in pressure, closing the adjacent flow channel. Subsequent cooling of the fluid would relieve pressure and permit the flow channel to open.

8. Networked Systems

Figure 12A:
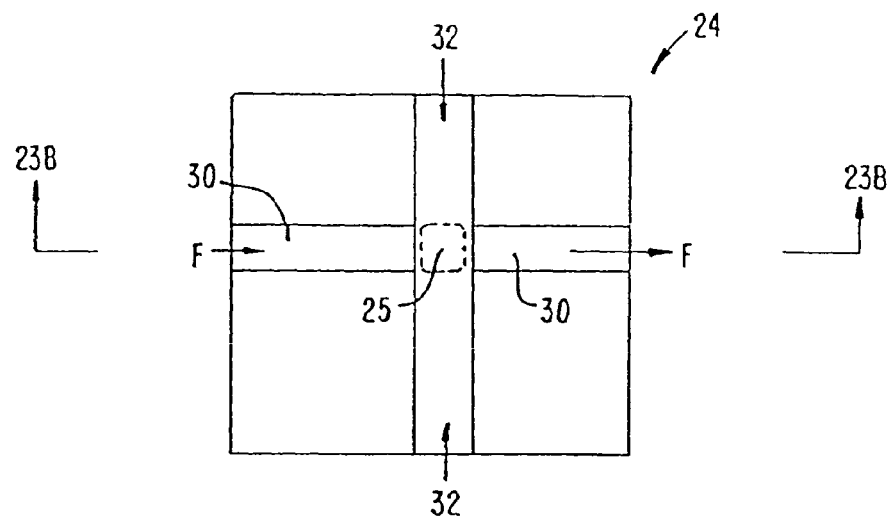
FIG. 12A is a top schematic view of an on/off valve.
Figure 13A:
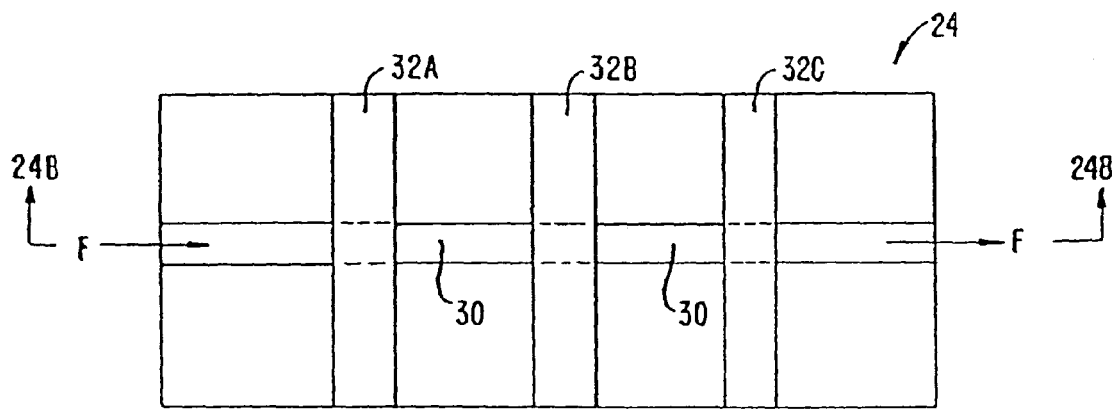
FIG. 13A is a top schematic view of a peristaltic pumping system.
Figure 12B:
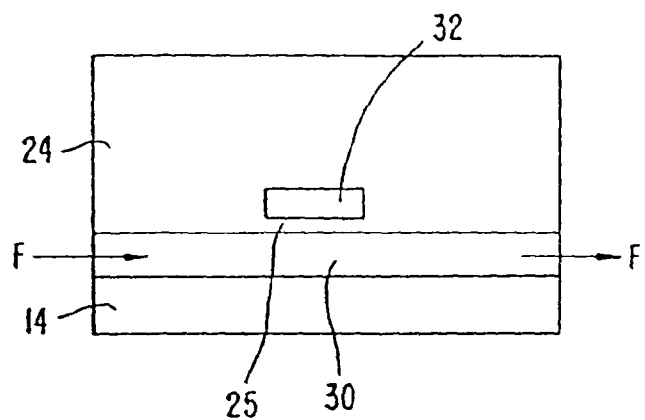
FIG. 12B is a sectional elevation view along line 23B-23B in FIG. 12A
Figure 13B:
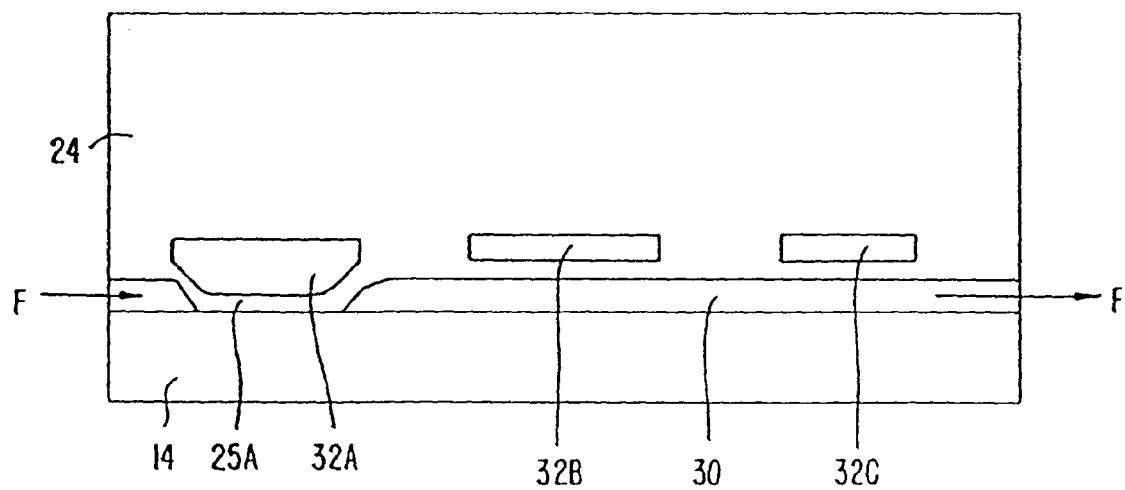
FIG. 13B is a sectional elevation view along line 24B-24B in FIG. 13A
Figure 14:
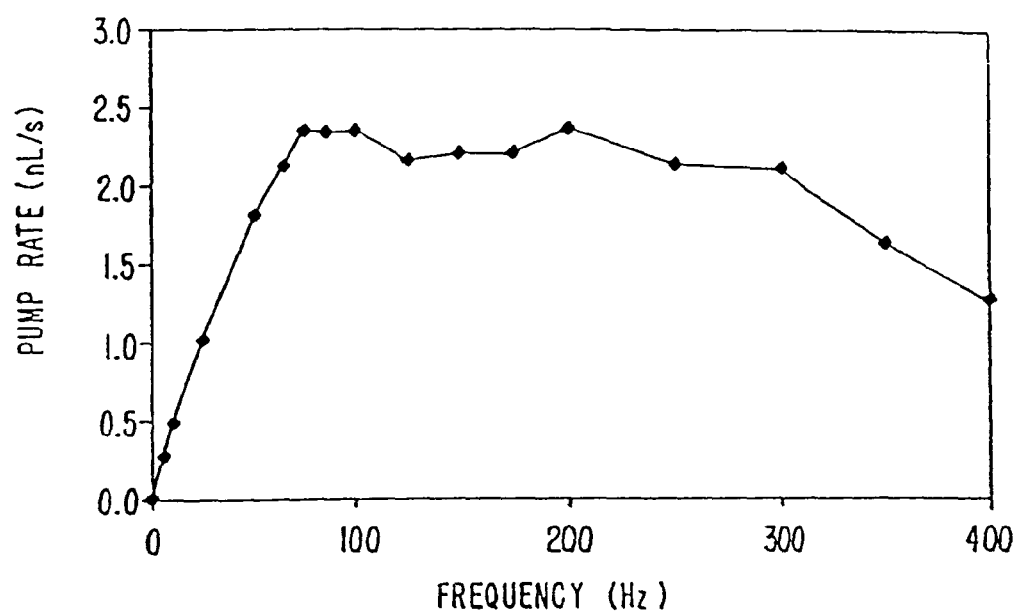
FIG. 14 is a graph showing experimentally achieved pumping rates vs. frequency for an embodiment of the peristaltic pumping system of FIG. 13.
Figure 15A:
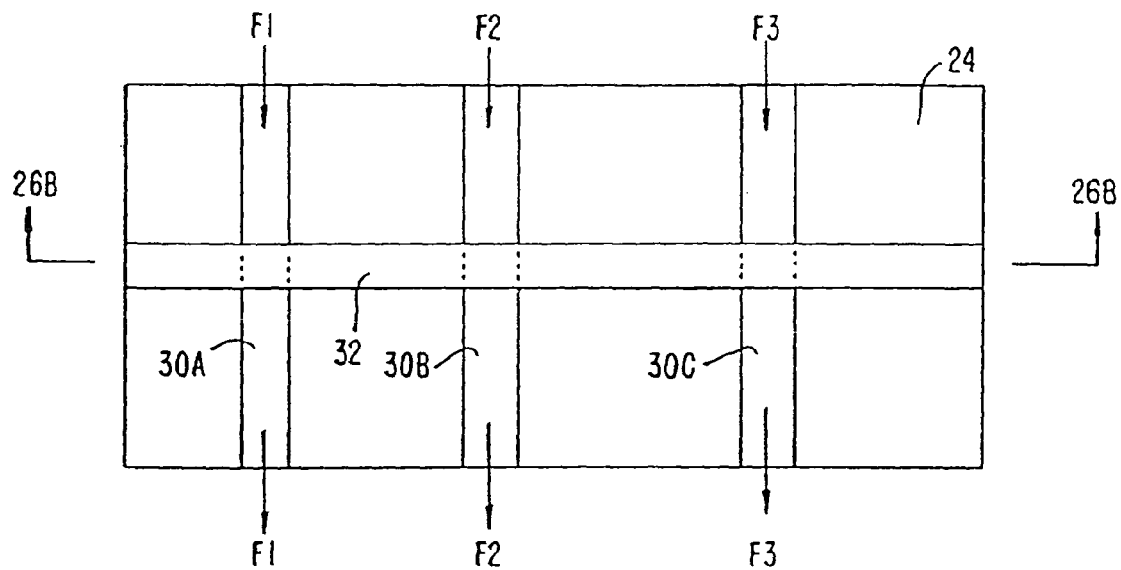
FIG. 15A is a top schematic view of one control line actuating multiple flow lines simultaneously.
Figure 15B:
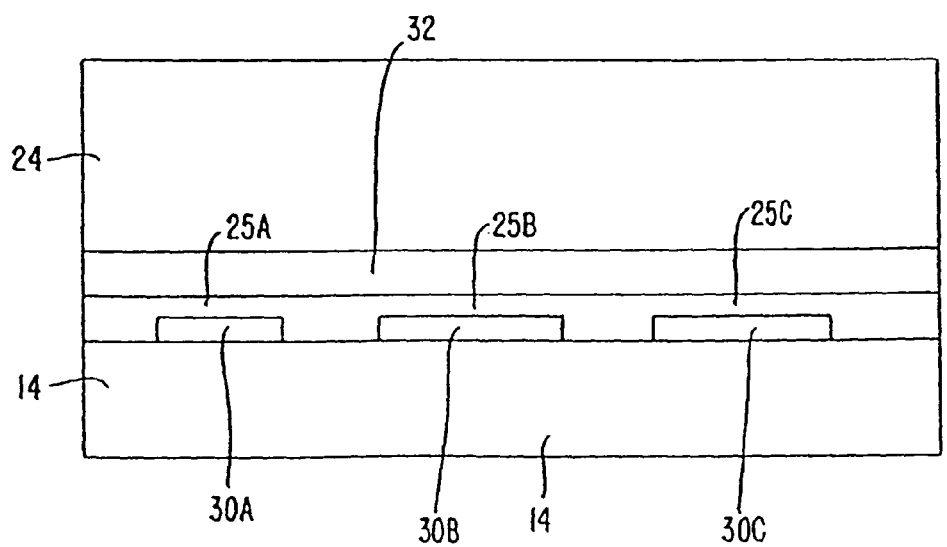
FIG. 15B is a sectional elevation view along line 26B-26B in FIG. 15A
Figure 16:
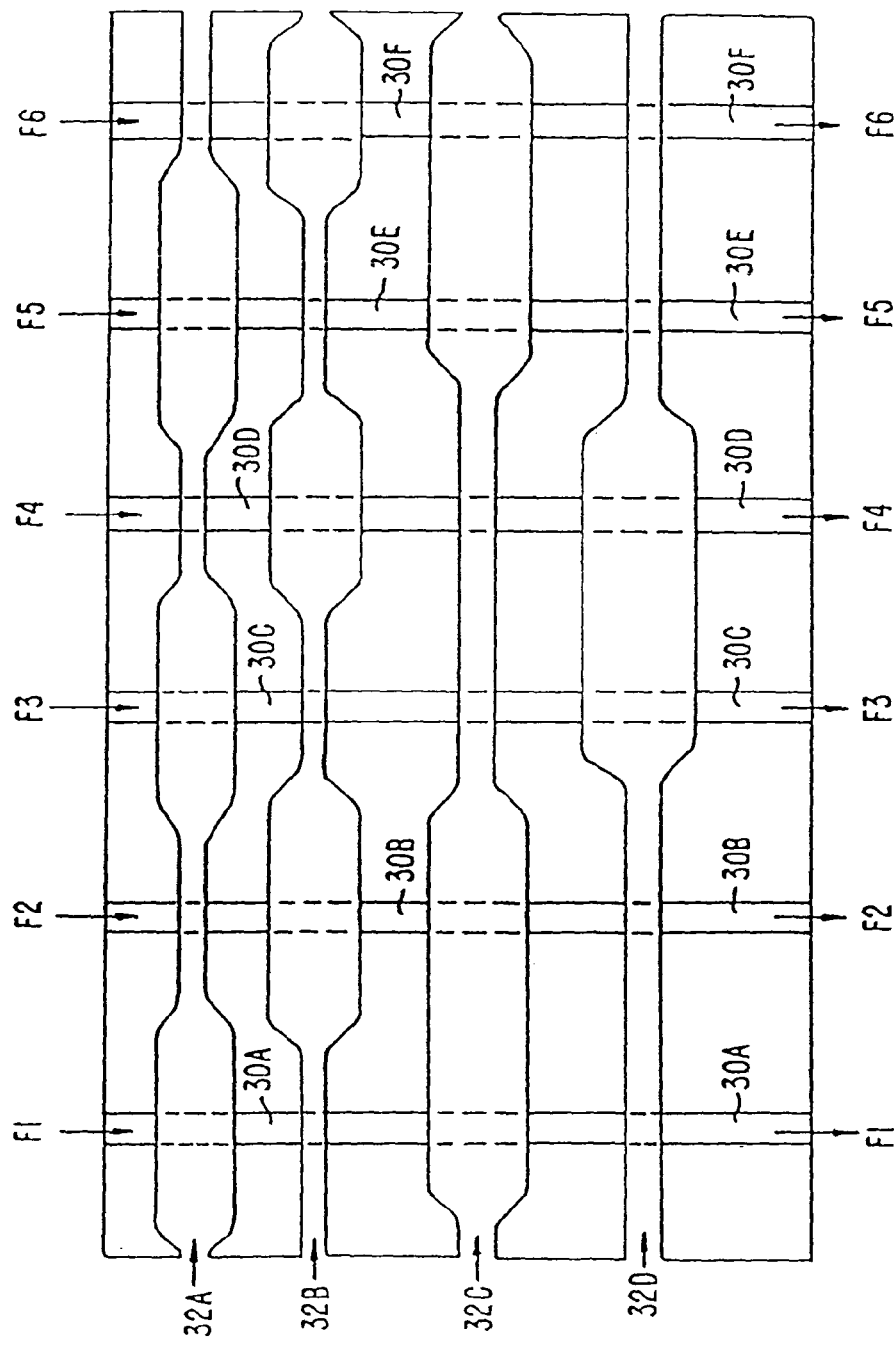
FIG. 16 is a schematic illustration of a multiplexed system adapted to permit flow through various channels.

FIGS. 12A and 12B show a views of a single on/off valve, identical to the systems set forth above, (for example in FIG. 7A). FIGS. 13A and 13B shows a peristaltic pumping system comprised of a plurality of the single addressable on/off valves as seen in FIG. 12, but networked together. FIG. 14 is a graph showing experimentally achieved pumping rates vs. frequency for the peristaltic pumping system of FIG. 13. FIGS. 15A and 15B show a schematic view of a plurality of flow channels which are controllable by a single control line. This system is also comprised of a plurality of the single addressable on/off valves of FIG. 12, multiplexed together, but in a different arrangement than that of FIG. 12. FIG. 16 is a schematic illustration of a multiplexing system adapted to permit fluid flow through selected channels, comprised of a plurality of the single on/off valves of FIG. 12, joined or networked together.

Referring first to FIGS. 12A and 12B, a schematic of flow channels 30 and 32 is shown. Flow channel 30 preferably has a fluid (or gas) flow F passing therethrough. Flow channel 32, (which crosses over flow channel 30, as was already explained herein), is pressurized such that membrane 25 separating the flow channels may be depressed into the path of flow channel 30, shutting off the passage of flow F therethrough, as has been explained. As such, "flow channel" 32 can also be referred to as a "control line" which actuates a single valve in flow channel 30. In FIGS. 12 to 15, a plurality of such addressable valves are joined or networked together in various arrangements to produce pumps, capable of peristaltic pumping, and other fluidic logic applications.

Referring to FIGS. 13A and 13B, a system for peristaltic pumping is provided, as follows. A flow channel 30 has a plurality of generally parallel flow channels (i.e.: control lines) 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc.

Each of control lines 32A, 32B, and 32C is separately addressable. Therefore, peristalsis may be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

In experiments performed by the inventors, a pumping rate of 2.35 nL/s was measured by measuring the distance traveled by a column of water in thin (0.5 mm i.d.) tubing; with 100×100×10 µm valves under an actuation pressure of 40 kPa. The pumping rate increased with actuation frequency until approximately 75 Hz, and then was nearly constant until above 200 Hz. The valves and pumps are also quite durable and the elastomer membrane, control channels, or bond have never been observed to fail. In experiments performed by the inventors, none of the valves in the peristaltic pump described herein show any sign of wear or fatigue after more than 4 million actuations. In addition to their durability, they are also gentle. A solution of E. Coli pumped through a channel and tested for viability showed a 94% survival rate.

FIG. 14 is a graph showing experimentally achieved pumping rates vs. frequency for the peristaltic pumping system of FIG. 13.

FIGS. 15A and 15B illustrates another way of assembling a plurality of the addressable valves of FIG. 12. Specifically, a plurality of parallel flow channels 30A, 30B, and 30C are provided. Flow channel (i.e.: control line) 32 passes thereover across flow channels 30A, 30B, and 30C. Pressurization of control line 32 simultaneously shuts off flows F1, F2 and F3 by depressing membranes 25A, 25B, and 25C located at the intersections of control line 32 and flow channels 30A, 30B, and 30C.

FIG. 16 is a schematic illustration of a multiplexing system adapted to selectively permit fluid to flow through selected channels, as follows. The downward deflection of membranes separating the respective flow channels from a control line passing thereabove (for example, membranes 25A, 25B, and 25C in FIGS. 15A and 15B) depends strongly upon the membrane dimensions. Accordingly, by varying the widths of flow channel control line 32 in FIGS. 15A and 15B, it is possible to have a control line pass over multiple flow channels, yet only actuate (i.e.: seal) desired flow channels. FIG. 16 illustrates a schematic of such a system, as follows.

A plurality of parallel flow channels 30A, 30B, 30C, 30D, 30E and 30F are positioned under a plurality of parallel control lines 32A, 32B, 32C, 32D, 32E and 32F. Control channels 32A, 32B, 32C, 32D, 32E and 32F are adapted to shut off fluid flows F1, F2, F3, F4, F5 and F6 passing through parallel flow channels 30A, 30B, 30C, 30D, 30E and 30F using any of the valving systems described above, with the following modification.

Each of control lines 32A, 32B, 32C, 32D, 32E and 32F have both wide and narrow portions. For example, control line 32A is wide in locations disposed over flow channels 30A, 30C and 30E. Similarly, control line 32B is wide in locations disposed over flow channels 30B, 30D and 30F, and control line 32C is wide in locations disposed over flow channels 30A, 30B, 30E and 30F.

At the locations where the respective control line is wide, its pressurization will cause the membrane (25) separating the flow channel and the control line to depress significantly into the flow channel, thereby blocking the flow passage therethrough. Conversely, in the locations where the respective control line is narrow, membrane (25) will also be narrow. Accordingly, the same degree of pressurization will not result in membrane (25) becoming depressed into the flow channel (30). Therefore, fluid passage thereunder will not be blocked.

For example, when control line 32A is pressurized, it will block flows F1, F3 and F5 in flow channels 30A, 30C and 30E. Similarly, when control line 32C is pressurized, it will block flows F1, F2, F5 and F6 in flow channels 30A, 30B, 30E and 30F. As can be appreciated, more than one control line can be actuated at the same time. For example, control lines 32A and 32C can be pressurized simultaneously to block all fluid flow except F4 (with 32A blocking F1, F3 and F5; and 32C blocking F1, F2, F5 and F6).

By selectively pressurizing different control lines (32) both together and in various sequences, a great degree of fluid flow control can be achieved. Moreover, by extending the present system to more than six parallel flow channels (30) and more than four parallel control lines (32), and by varying the positioning of the wide and narrow regions of the control lines, very complex fluid flow control systems may be fabricated. A property of such systems is that it is possible to turn on any one flow channel out of n flow channels with only 2(log 2n) control lines.

9. Selectively Addressable Reaction Chambers Along Flow Lines

In a further embodiment of the invention, illustrated in FIGS. 17A, 17B, 17C and 17D, a system for selectively directing fluid flow into one more of a plurality of reaction chambers disposed along a flow line is provided.

Figure 17A:
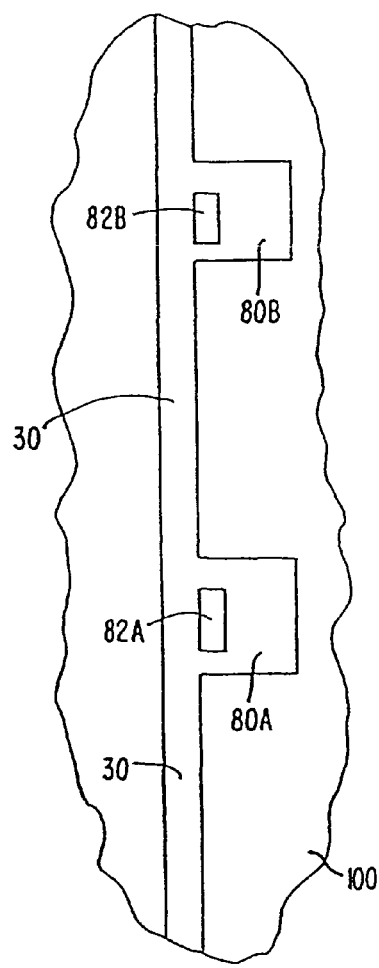
FIG. 17A is a plan view of a flow layer of an addressable reaction chamber structure.

FIG. 17A shows a top view of a flow channel 30 having a plurality of reaction chambers 80A and 80B disposed therealong. Preferably flow channel 30 and reaction chambers 80A and 80B are formed together as recesses into the bottom surface of a first layer 100 of elastomer.

Figure 17B:
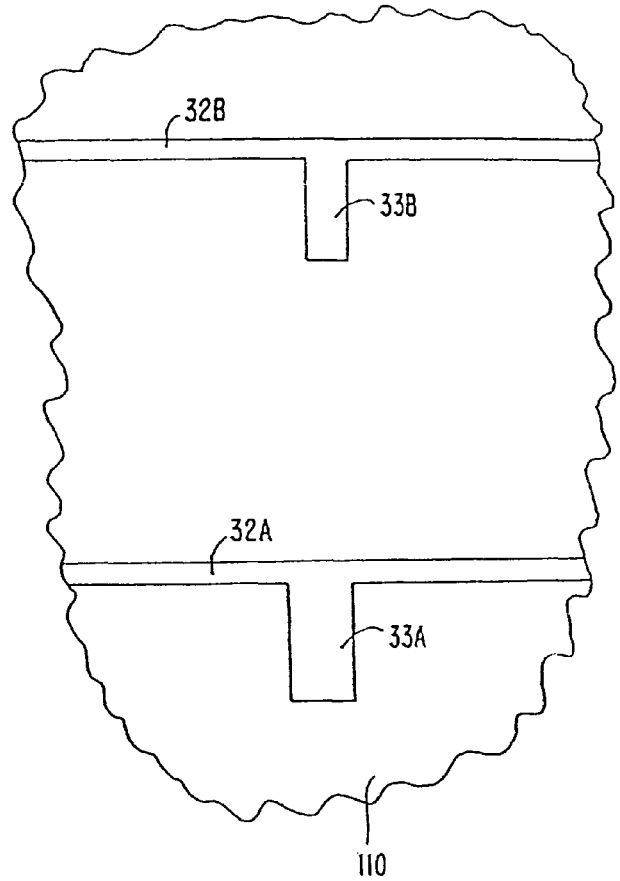
FIG. 17B is a bottom plan view of a control channel layer of an addressable reaction chamber structure.

FIG. 17B shows a bottom plan view of another elastomeric layer 110 with two control lines 32A and 32B each being generally narrow, but having wide extending portions 33A and 33B formed as recesses therein.

Figure 17C:
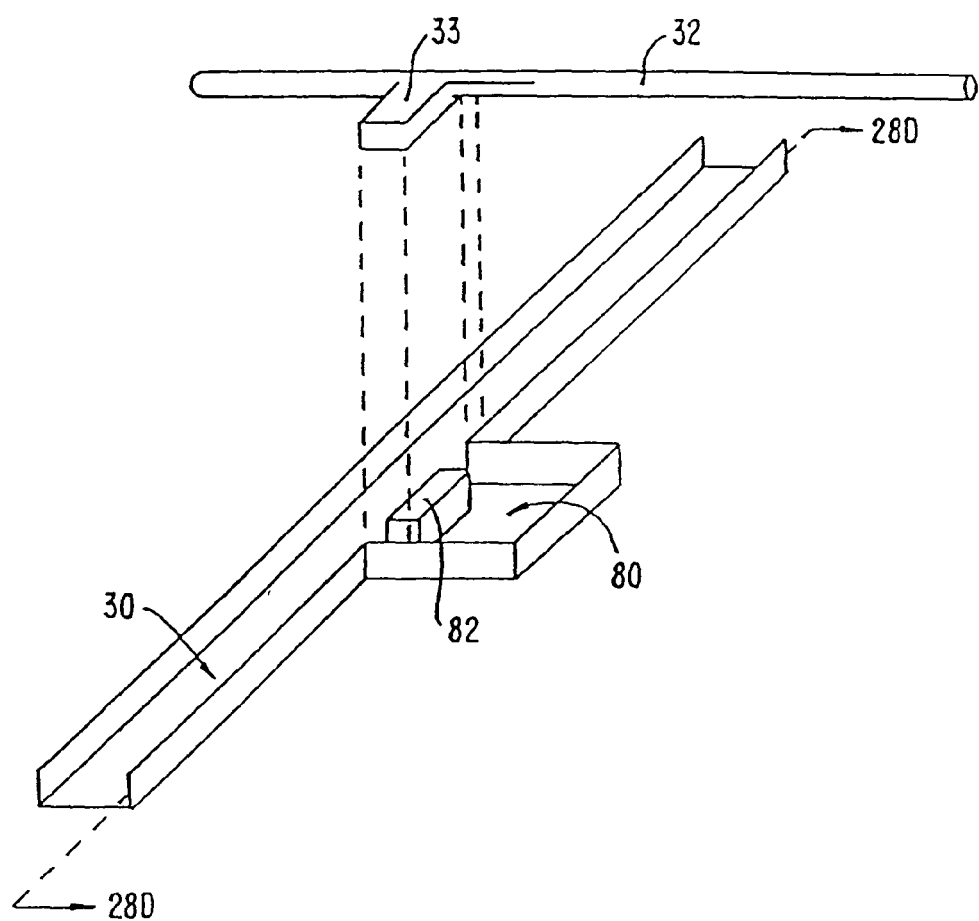
FIG. 17C is an exploded perspective view of the addressable reaction chamber structure formed by bonding the control channel layer of FIG. 17B to the top of the flow layer of FIG. 17A.
Figure 17D:
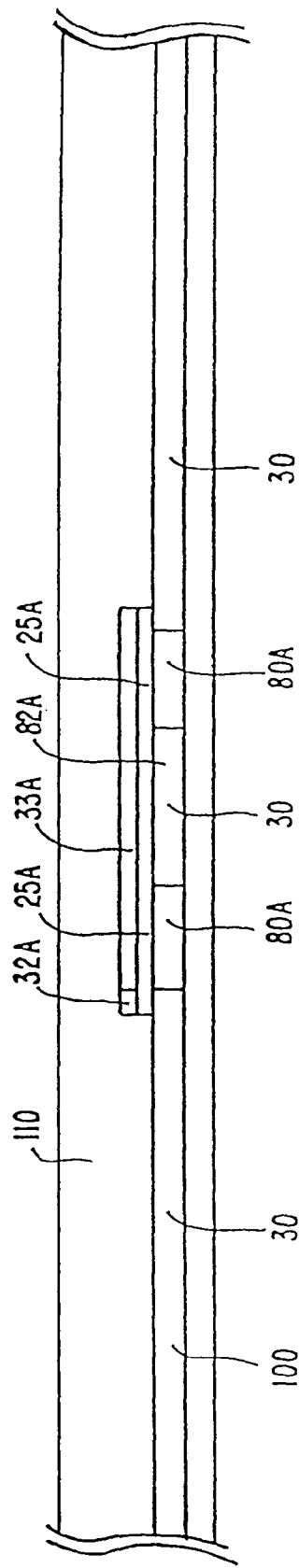
FIG. 17D is a sectional elevation view corresponding to FIG. 17C, taken along line 28D-28D in FIG. 17C.
Figure 18:
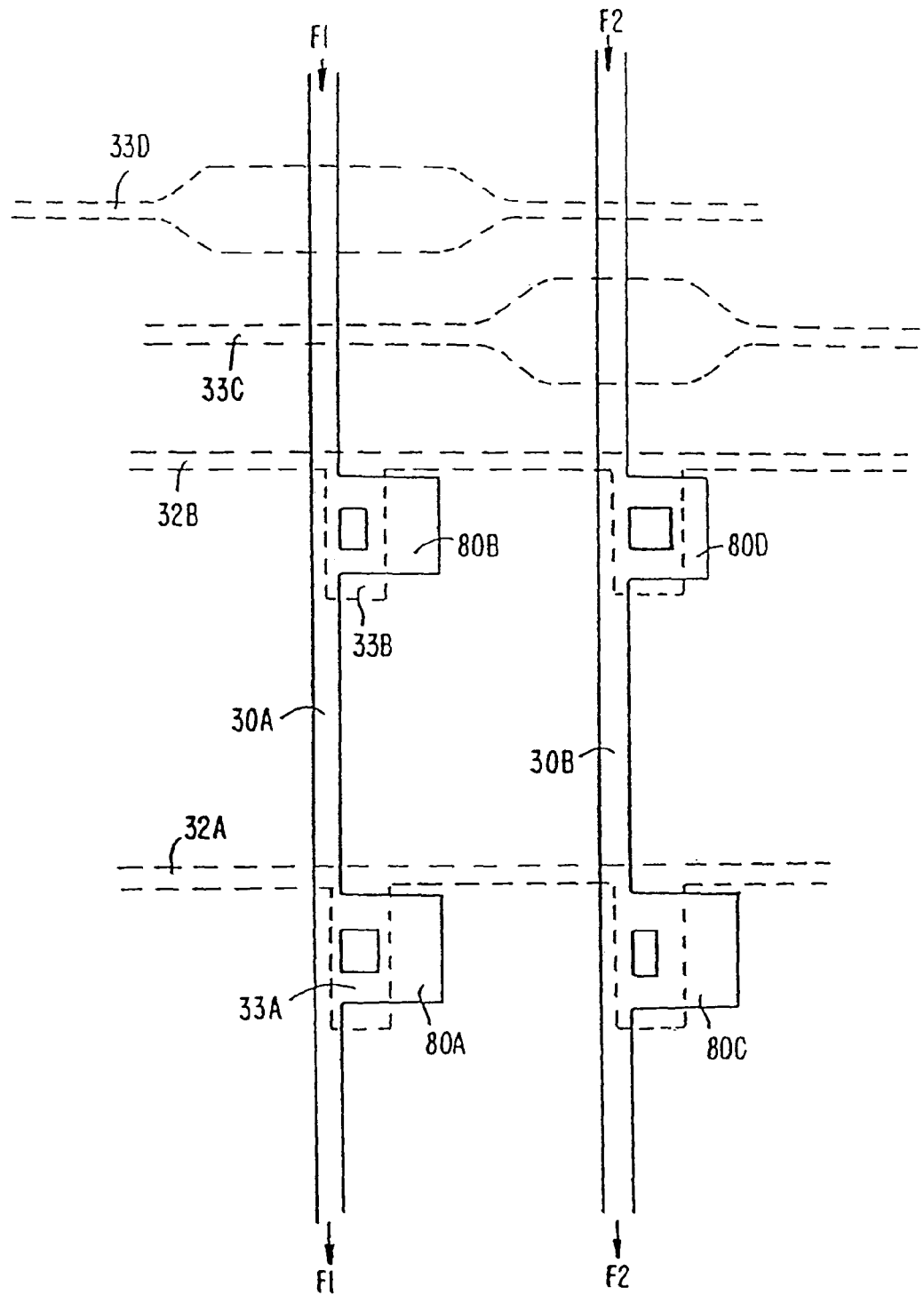
FIG. 18 is a schematic of a system adapted to selectively direct fluid flow into any of an array of reaction wells.

As seen in the exploded view of FIG. 17C, and assembled view of FIG. 17D, elastomeric layer 110 is placed over elastomeric layer 100. Layers 100 and 110 are then bonded together, and the integrated system operates to selectively direct fluid flow F (through flow channel 30) into either or both of reaction chambers 80A and 80B, as follows. Pressurization of control line 32A will cause the membrane 25 (i.e.: the thin portion of elastomer layer 100 located below extending portion 33A and over regions 82A of reaction chamber 80A) to become depressed, thereby shutting off fluid flow passage in regions 82A, effectively sealing reaction chamber 80 from flow channel 30. As can also be seen, extending portion 33A is wider than the remainder of control line 32A. As such, pressurization of control line 32A will not result in control line 32A sealing flow channel 30.

As can be appreciated, either or both of control lines 32A and 32B can be actuated at once. When both control lines 32A and 32B are pressurized together, sample flow in flow channel 30 will enter neither of reaction chambers 80A or 80B.

The concept of selectably controlling fluid introduction into various addressable reaction chambers disposed along a flow line (FIGS. 17A-D) can be combined with concept of selectably controlling fluid flow through one or more of a plurality of parallel flow lines (FIG. 16) to yield a system in which a fluid sample or samples can be can be sent to any particular reaction chamber in an array of reaction chambers. An example of such a system is provided in FIG. 18, in which parallel control channels 32A, 32B and 32C with extending portions 34 (all shown in phantom) selectively direct fluid flows F1 and F2 into any of the array of reaction wells 80A, 80B, 80C or 80D as explained above; while pressurization of control lines 32C and 32D selectively shuts off flows F2 and F1, respectively.

Figure 19:
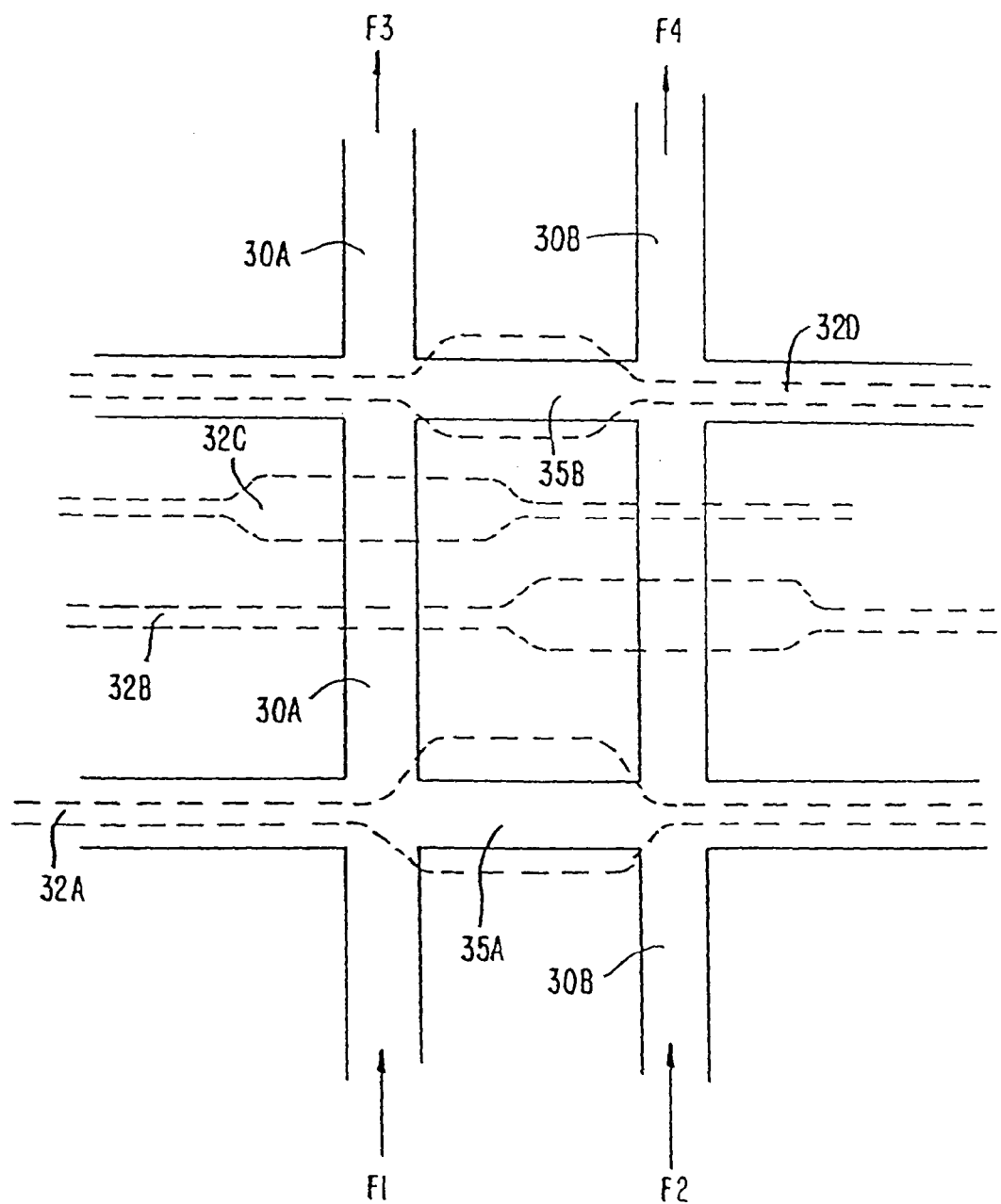
FIG. 19 is a schematic of a system adapted for selectable lateral flow between parallel flow channels.

In yet another novel embodiment, fluid passage between parallel flow channels is possible. Referring to FIG. 19, either or both of control lines 32A or 32D can be depressurized such that fluid flow through lateral passageways 35 (between parallel flow channels 30A and 30B) is permitted. In this aspect of the invention, pressurization of control lines 32C and 32D would shut flow channel 30A between 35A and 35B, and would also shut lateral passageways 35B. As such, flow entering as flow F1 would sequentially travel through 30A, 35A and leave 30B as flow F4.

10. Switchable Flow Arrays

Figure 20A:
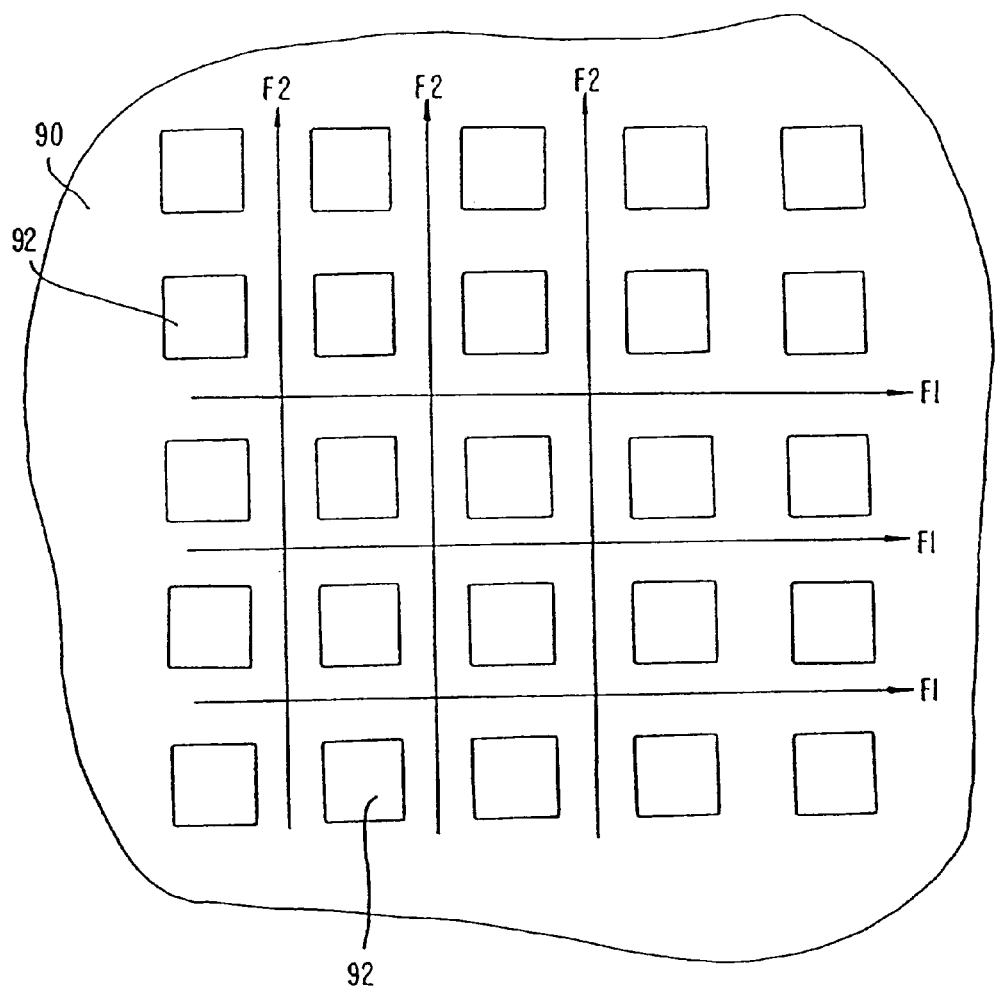
FIG. 20A is a bottom plan view of first layer (i.e.: the flow channel layer) of elastomer of a switchable flow array.
Figure 20B:
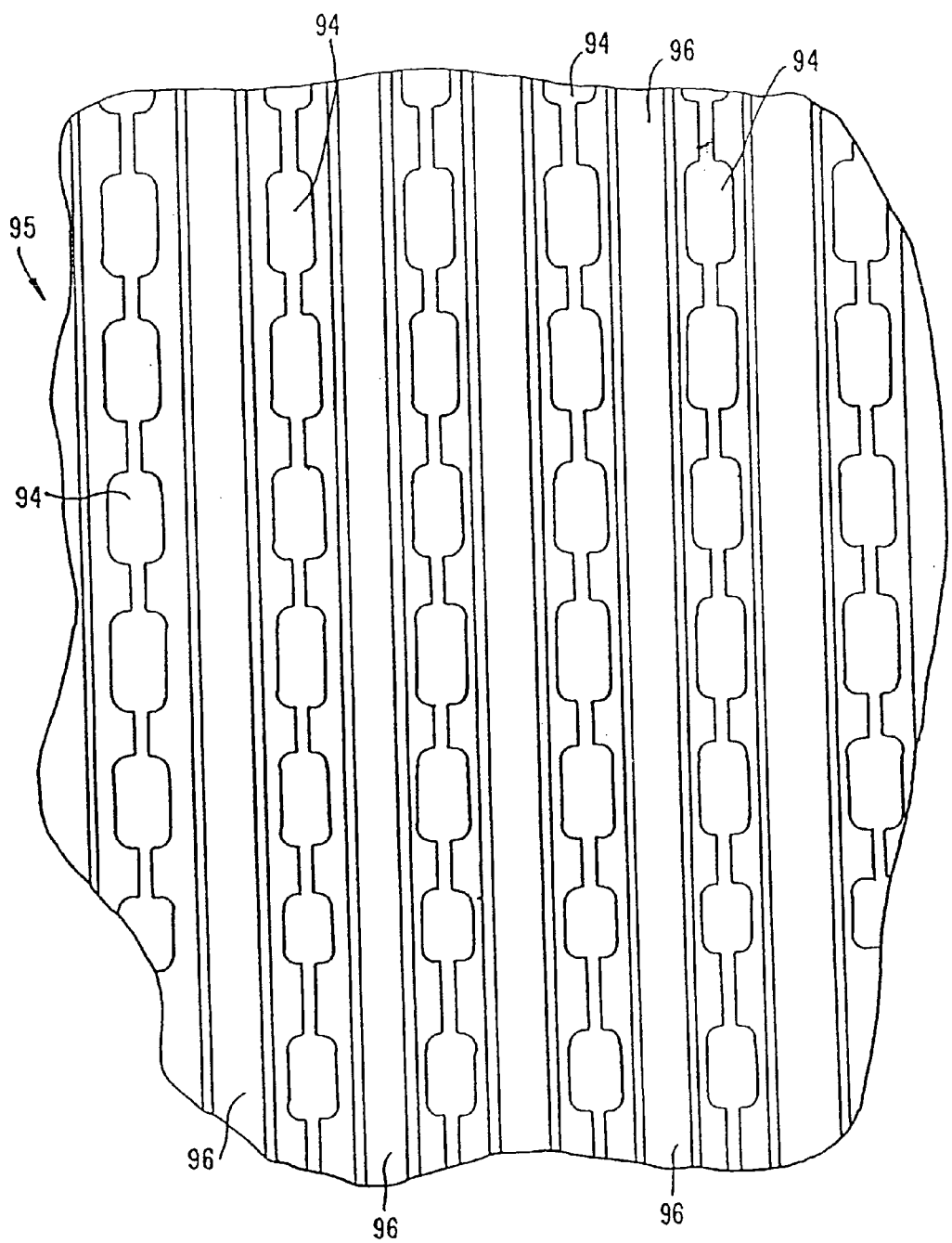
FIG. 20B is a bottom plan view of a control channel layer of a switchable flow array.

In yet another novel embodiment, fluid passage can be selectively directed to flow in either of two perpendicular directions. An example of such a "switchable flow array" system is provided in FIGS. 20A to 20D. FIG. 20A shows a bottom view of a first layer of elastomer 90, (or any other suitable substrate), having a bottom surface with a pattern of recesses forming a flow channel grid defined by an array of solid posts 92, each having flow channels passing therearound.

In preferred aspects, an additional layer of elastomer is bound to the top surface of layer 90 such that fluid flow can be selectively directed to move either in direction F1, or perpendicular direction F2. FIG. 20 is a bottom view of the bottom surface of the second layer of elastomer 95 showing recesses formed in the shape of alternating "vertical" control lines 96 and "horizontal" control lines 94. "Vertical" control lines 96 have the same width therealong, whereas "horizontal" control lines 94 have alternating wide and narrow portions, as shown.

Figure 20C:
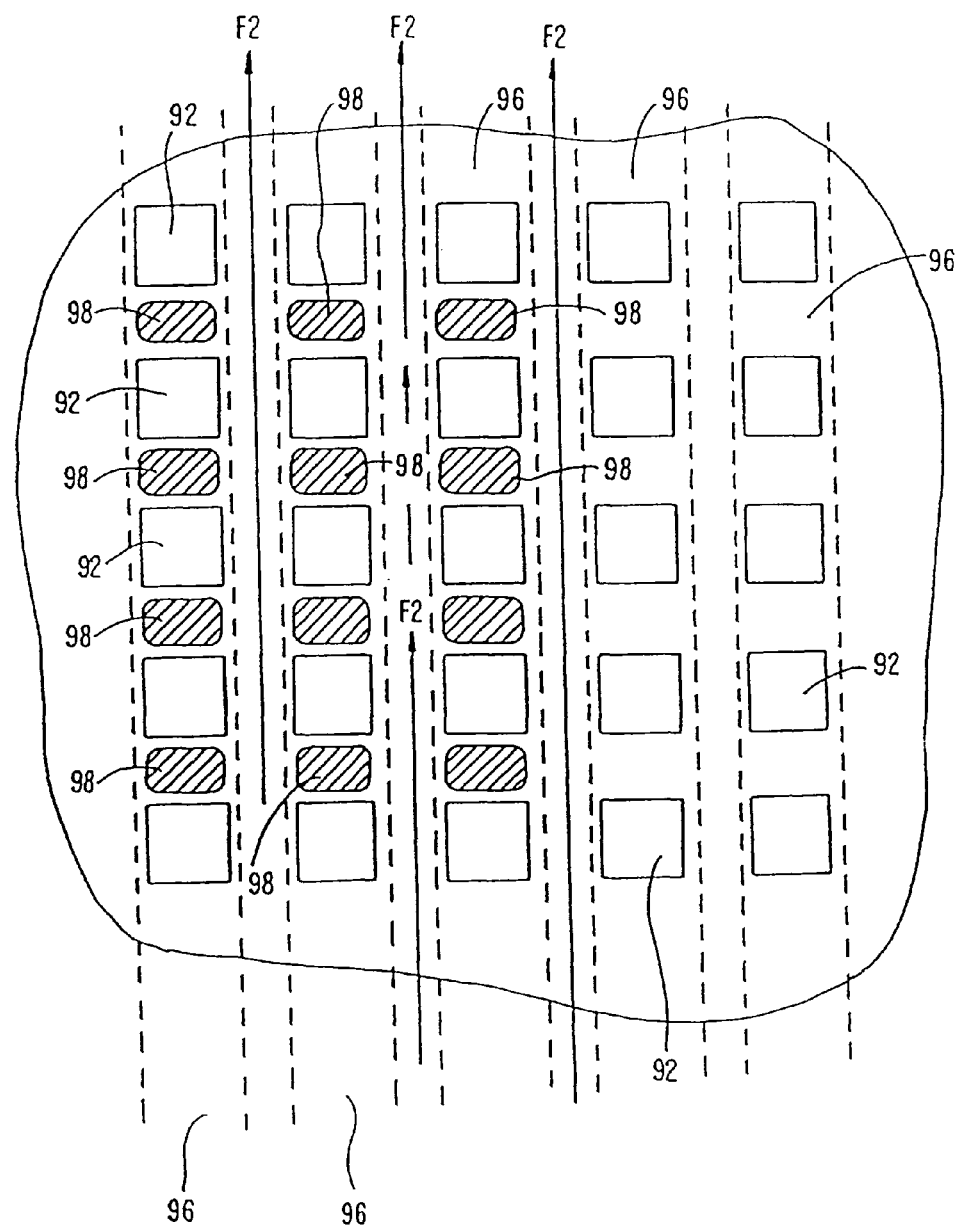
FIG. 20C shows the alignment of the first layer of elastomer of FIG. 20A with one set of control channels in the second layer of elastomer of FIG. 20B.
Figure 20D:
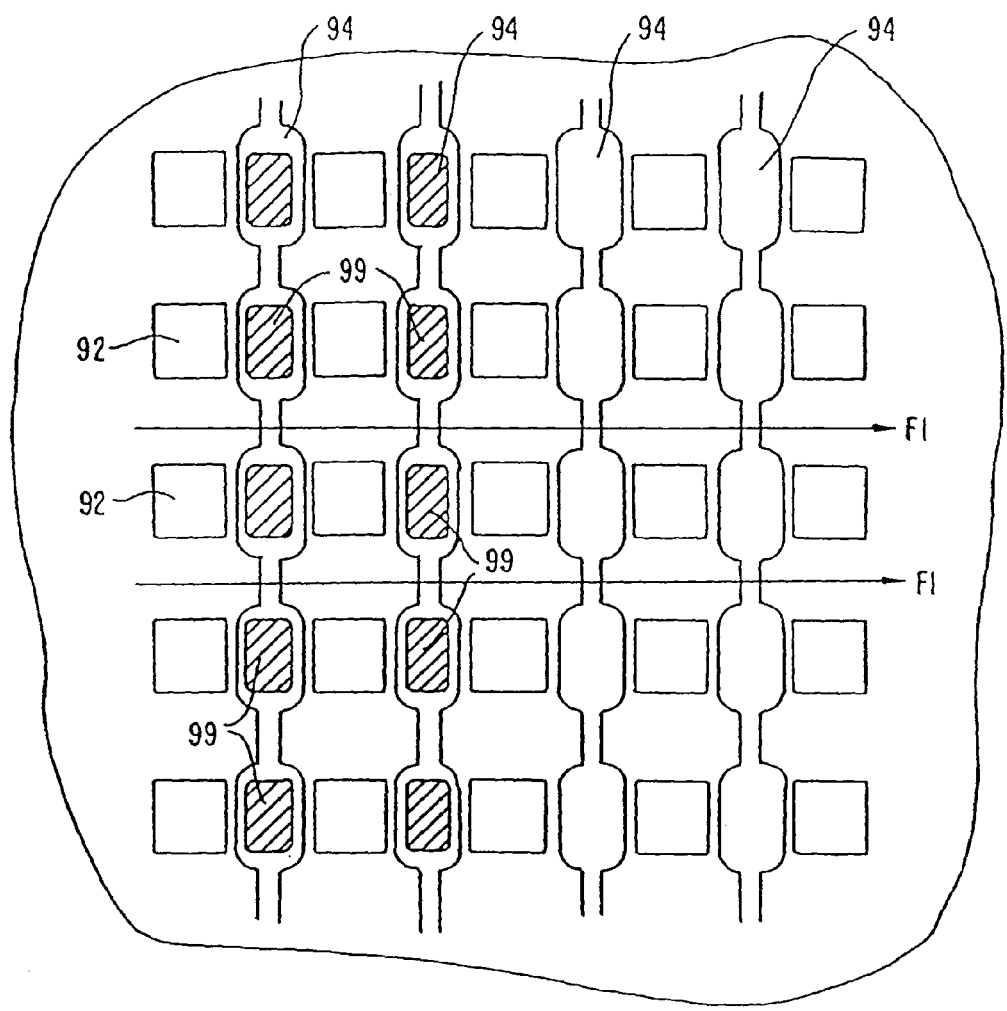
FIG. 20D also shows the alignment of the first layer of elastomer of FIG. 20A with the other set of control channels in the second layer of elastomer of FIG. 20B.

Elastomeric layer 95 is positioned over top of elastomeric layer 90 such that "vertical" control lines 96 are positioned over posts 92 as shown in FIG. 20C and "horizontal" control lines 94 are positioned with their wide portions between posts 92, as shown in FIG. 20D.

As can be seen in FIG. 20C, when "vertical" control lines 96 are pressurized, the membrane of the integrated structure formed by the elastomeric layer initially positioned between layers 90 and 95 in regions 98 will be deflected downwardly over the array of flow channels such that flow in only able to pass in flow direction F2 (i.e.: vertically), as shown.

As can be seen in FIG. 20D, when "horizontal" control lines 94 are pressurized, the membrane of the integrated structure formed by the elastomeric layer initially positioned between layers 90 and 95 in regions 99 will be deflected downwardly over the array of flow channels, (but only in the regions where they are widest), such that flow in only able to pass in flow direction F1 (i.e.: horizontally), as shown.

The design illustrated in FIG. 20 allows a switchable flow array to be constructed from only two elastomeric layers, with no vertical vias passing between control lines in different elastomeric layers required. If all vertical flow control lines 94 are connected, they may be pressurized from one input. The same is true for all horizontal flow control lines 96.

11. Normally-Closed Valve Structure

FIGS. 7B and 7H above depict a valve structure in which the elastomeric membrane is moveable from a first relaxed position to a second actuated position in which the flow channel is blocked. However, the present invention is not limited to this particular valve configuration.

FIGS. 21A-21J show a variety of views of a normally-closed valve structure in which the elastomeric membrane is moveable from a first relaxed position blocking a flow channel, to a second actuated position in which the flow channel is open, utilizing a negative control pressure.

FIG. 21A shows a plan view, and FIG. 21B shows a cross sectional view along line 42B-42B', of normally-closed valve 4200 in an unactuated state. Flow channel 4202 and control channel 4204 are formed in elastomeric block 4206 overlying substrate 4205. Flow channel 4202 includes a first portion 4202a and a second portion 4202b separated by separating portion 4208. Control channel 4204 overlies separating portion 4208. As shown in FIG. 42B, in its relaxed, unactuated position, separating portion 4008 remains positioned between flow channel portions 4202a and 4202b, interrupting flow channel 4202.

Figure 21D:
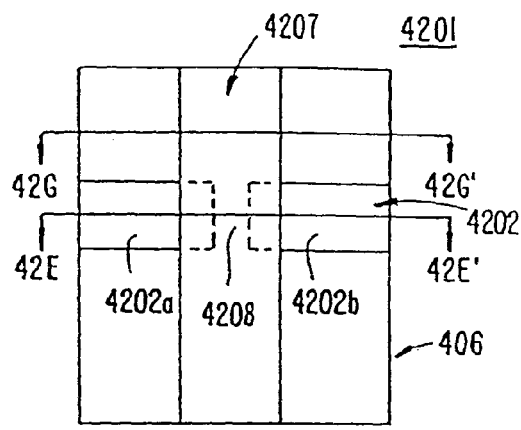
Figure 21B:
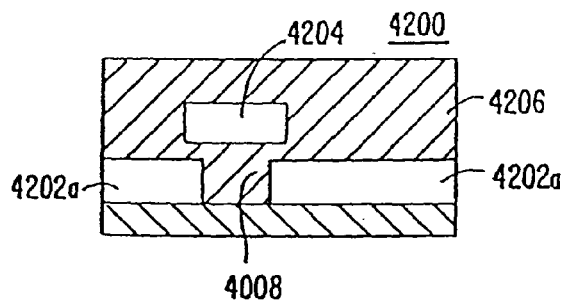
Figure 21E:
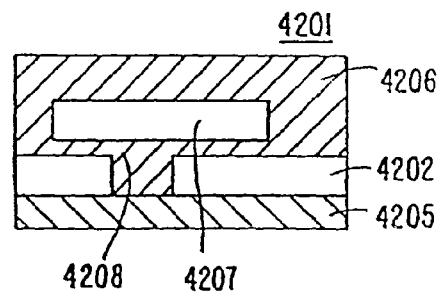
Figure 21C:
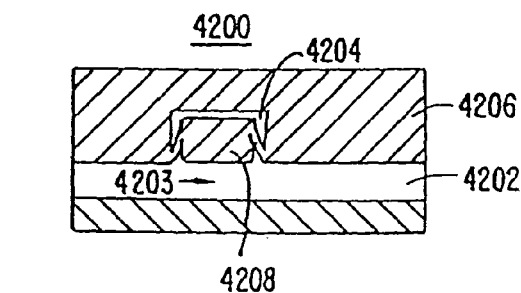
Figure 21F:
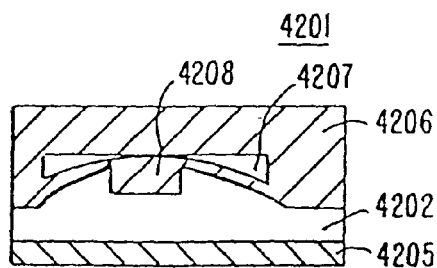

FIG. 21C shows a cross-sectional view of valve 4200 wherein separating portion 4208 is in an actuated position. When the pressure within control channel 4204 is reduced to below the pressure in the flow channel (for example by vacuum pump), separating portion 4208 experiences an actuating force drawing it into control channel 4204. As a result of this actuation force membrane 4208 projects into control channel 4204, thereby removing the obstacle to a flow of material through flow channel 4202 and creating a passageway 4203. Upon elevation of pressure within control channel 4204, separating portion 4208 will assume its natural position, relaxing back into and obstructing flow channel 4202.

The behavior of the membrane in response to an actuation force may be changed by varying the width of the overlying control channel. Accordingly, FIGS. 21D-42H show plan and cross-sectional views of an alternative embodiment of a normally-closed valve 4201 in which control channel 4207 is substantially wider than separating portion 4208. As shown in cross-sectional views FIGS. 21E-F along line 42E-42E' of FIG. 21D, because a larger area of elastomeric material is required to be moved during actuation, the actuation force necessary to be applied is reduced.

Figure 21I:
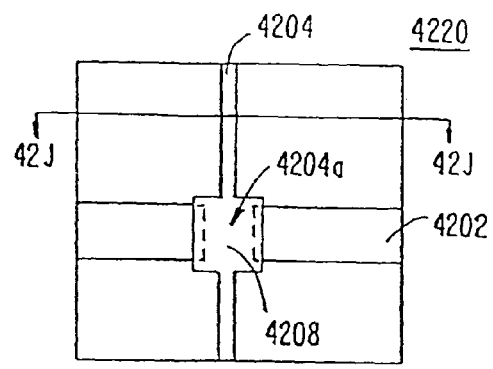
Figure 21G:
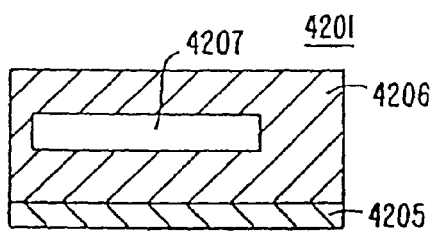

FIGS. 21G and H show a cross-sectional views along line 40G-40G' of FIG. 21D. In comparison with the unactuated valve configuration shown in FIG. 21G, FIG. 21H shows that reduced pressure within wider control channel 4207 may under certain circumstances have the unwanted effect of pulling underlying elastomer 4206 away from substrate 4205, thereby creating undesirable void 4212.

Figure 21J:
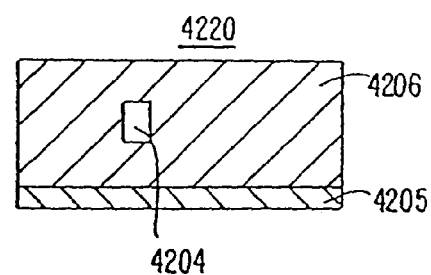
Figure 21H:
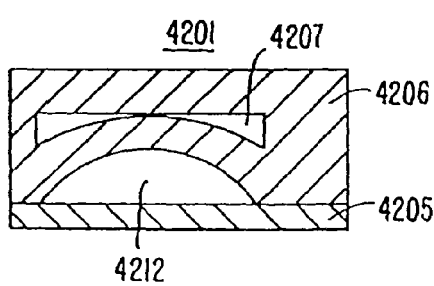

Accordingly, FIG. 21I shows a plan view, and FIG. 21J shows a cross-sectional view along line 21J-21J' of FIG. 21I, of valve structure 4220 which avoids this problem by featuring control line 4204 with a minimum width except in segment 4204a overlapping separating portion 4208. As shown in FIG. 21J, even under actuated conditions the narrower cross-section of control channel 4204 reduces the attractive force on the underlying elastomer material 4206, thereby preventing this elastomer material from being drawn away from substrate 4205 and creating an undesirable void.

While a normally-closed valve structure actuated in response to pressure is shown in FIGS. 21A-21J, a normally-closed valve in accordance with the present invention is not limited to this configuration. For example, the separating portion obstructing the flow channel could alternatively be manipulated by electric or magnetic fields, as described extensively above.

12. Side-Actuated Valve

Figures 22A, 22B:
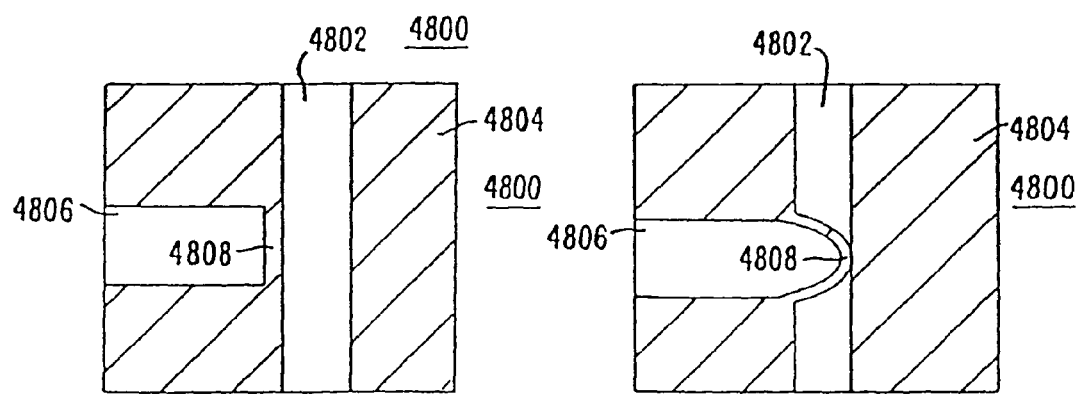
FIGS. 22A and 22B show plan views illustrating operation of one embodiment of a side-actuated valve structure in accordance with the present invention.

While the above description has focused upon microfabricated elastomeric valve structures in which a control channel is positioned above and separated by an intervening elastomeric membrane from an underlying flow channel, the present invention is not limited to this configuration. FIGS. 22A and 22B show plan views of one embodiment of a side-actuated valve structure in accordance with one embodiment of the present invention.

FIG. 22A shows side-actuated valve structure 4800 in an unactuated position. Flow channel 4802 is formed in elastomeric layer 4804. Control channel 4806 abutting flow channel 4802 is also formed in elastomeric layer 4804. Control channel 4806 is separated from flow channel 4802 by elastomeric membrane portion 4808. A second elastomeric layer (not shown) is bonded over bottom elastomeric layer 4804 to enclose flow channel 4802 and control channel 4806.

FIG. 22B shows side-actuated valve structure 4800 in an actuated position. In response to a build up of pressure within control channel 4806, membrane 4808 deforms into flow channel 4802, blocking flow channel 4802. Upon release of pressure within control channel 4806, membrane 4808 would relax back into control channel 4806 and open flow channel 4802.

While a side-actuated valve structure actuated in response to pressure is shown in FIGS. 22A and 22B, a side-actuated valve in accordance with the present invention is not limited to this configuration. For example, the elastomeric membrane portion located between the abutting flow and control channels could alternatively be manipulated by electric or magnetic fields, as described extensively above.

13. Composite Structures

Figure 23:
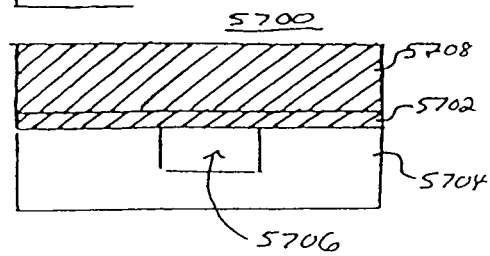
FIG. 23 shows a cross-sectional view of one embodiment of a composite structure in accordance with the present invention.

Microfabricated elastomeric structures of the present invention may be combined with non-elastomeric materials to create composite structures. FIG. 23 shows a cross-sectional view of one embodiment of a composite structure in accordance with the present invention. FIG. 23 shows composite valve structure 5700 including first, thin elastomer layer 5702 overlying semiconductor-type substrate 5704 having channel 5706 formed therein. Second, thicker elastomer layer 5708 overlies first elastomer layer 5702. Actuation of first elastomer layer 5702 to drive it into channel 5706, will cause composite structure 5700 to operate as a valve.

Figure 24:
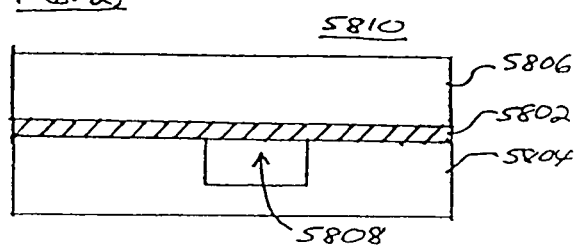
FIG. 24 shows a cross-sectional view of another embodiment of a composite structure in accordance with the present invention.

FIG. 24 shows a cross-sectional view of a variation on this theme, wherein thin elastomer layer 5802 is sandwiched between two hard, semiconductor substrates 5804 and 5806, with lower substrate 5804 featuring channel 5808. Again, actuation of thin elastomer layer 5802 to drive it into channel 5808 will cause composite structure 5810 to operate as a valve.

The structures shown in FIG. 23 or 24 may be fabricated utilizing either the multilayer soft lithography or encapsulation techniques described above. In the multilayer soft lithography method, the elastomer layer(s) would be formed and then placed over the semiconductor substrate bearing the channel. In the encapsulation method, the channel would be first formed in the semiconductor substrate, and then the channel would be filled with a sacrificial material such as photoresist. The elastomer would then be formed in place over the substrate, with removal of the sacrificial material producing the channel overlaid by the elastomer membrane. As is discussed in detail below in connection with bonding of elastomer to other types of materials, the encapsulation approach may result in a stronger seal between the elastomer membrane component and the underlying nonelastomer substrate component.

Figure 25:
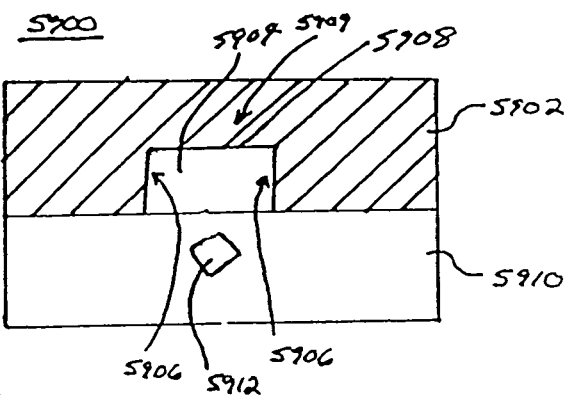
FIG. 25 shows a cross-sectional view of another embodiment of a composite structure in accordance with the present invention.

As shown in FIGS. 23 and 24, a composite structure in accordance with embodiments of the present invention may include a hard substrate that bears a passive feature such as a channels. However, the present invention is not limited to this approach, and the underlying hard substrate may bear active features that interact with an elastomer component bearing a recess. This is shown in FIG. 25, wherein composite structure 5900 includes elastomer component 5902 containing recess 5904 having walls 5906 and ceiling 5908. Ceiling 5908 forms flexible membrane portion 5909. Elastomer component 5902 is sealed against substantially planar nonelastomeric component 5910 that includes active device 5912. Active device 5912 may interact with material present in recess 5904 and/or flexible membrane portion 5909.

Many Types of active structures may be present in the nonelastomer substrate. Active structures that could be present in an underlying hard substrate include, but are not limited to, resistors, capacitors, photodiodes, transistors, chemical field effect transistors (chem FET's), amperometric/coulometric electrochemical sensors, fiber optics, fiber optic interconnects, light emitting diodes, laser diodes, vertical cavity surface emitting lasers (VCSEL's), micromirrors, accelerometers, pressure sensors, flow sensors, CMOS imaging arrays, CCD cameras, electronic logic, microprocessors, thermistors, Peltier coolers, waveguides, resistive heaters, chemical sensors, strain gauges, inductors, actuators (including electrostatic, magnetic, electromagnetic, bimetallic, piezoelectric, shape-memory-alloy based, and others), coils, magnets, electromagnets, magnetic sensors (such as those used in hard drives, superconducting quantum interference devices (SQUIDS) and other types), radio frequency sources and receivers, microwave frequency sources and receivers, sources and receivers for other regions of the electromagnetic spectrum, radioactive particle counters, and electrometers.

As is well known in the art, a vast variety of technologies can be utilized to fabricate active features in semiconductor and other types of hard substrates, including but not limited printed circuit board (PCB) technology, CMOS, surface micromachining, bulk micromachining, printable polymer electronics, and TFT and other amorphous/polycrystalline techniques as are employed to fabricate laptop and flat screen displays.

A variety of approaches can be employed to seal the elastomeric structure against the nonelastomeric substrate, ranging from the creation of a Van der Waals bond between the elastomeric and nonelastomeric components, to creation of covalent or ionic bonds between the elastomeric and nonelastomeric components of the composite structure. Example approaches to sealing the components together are discussed below, approximately in order of increasing strength.

A first approach is to rely upon the simple hermetic seal resulting from Van der Waals bonds formed when a substantially planar elastomer layer is placed into contact with a substantially planar layer of a harder, non-elastomer material. In one embodiment, bonding of RTV elastomer to a glass substrate created a composite structure capable of withstanding up to about 3-4 psi of pressure. This may be sufficient for many potential applications.

A second approach is to utilize a liquid layer to assist in bonding. One example of this involves bonding elastomer to a hard glass substrate, wherein a weakly acidic solution (5 µl HCl in $H_2O$, pH 2) was applied to a glass substrate. The elastomer component was then placed into contact with the glass substrate, and the composite structure baked at 37° C. to remove the water. This resulted in a bond between elastomer and non-elastomer able to withstand a pressure of about 20 psi. In this case, the acid may neutralize silanol groups present on the glass surface, permitting the elastomer and non-elastomer to enter into good Van der Waals contact with each other.

Exposure to ethanol can also cause device components to adhere together. In one embodiment, an RTV elastomer material and a glass substrate were washed with ethanol and then dried under Nitrogen. The RTV elastomer was then placed into contact with the glass and the combination baked for 3 hours at 80° C. Optionally, the RTV may also be exposed to a vacuum to remove any air bubbles trapped between the slide and the RTV. The strength of the adhesion between elastomer and glass using this method has withstood pressures in excess of 35 psi. The adhesion created using this method is not permanent, and the elastomer may be peeled off of the glass, washed, and resealed against the glass. This ethanol washing approach can also be employed used to cause successive layers of elastomer to bond together with sufficient strength to resist a pressure of 30 psi. In alternative embodiments, chemicals such as other alcohols or diols could be used to promote adhesion between layers.

An embodiment of a method of promoting adhesion between layers of a microfabricated structure in accordance with the present invention comprises exposing a surface of a first component layer to a chemical, exposing a surface of a second component layer to the chemical, and placing the surface of the first component layer into contact with the surface of the second elastomer layer.

A third approach is to create a covalent chemical bond between the elastomer component and functional groups introduced onto the surface of a nonelastomer component. Examples of derivitization of a nonelastomer substrate surface to produce such functional groups include exposing a glass substrate to agents such as vinyl silane or aminopropyltriethoxy silane (APTES), which may be useful to allow bonding of the glass to silicone elastomer and polyurethane elastomer materials, respectively.

A fourth approach is to create a covalent chemical bond between the elastomer component and a functional group native to the surface of the nonelastomer component. For example, RTV elastomer can be created with an excess of vinyl groups on its surface. These vinyl groups can be caused to react with corresponding functional groups present on the exterior of a hard substrate material, for example the Si—H bonds prevalent on the surface of a single crystal silicon substrate after removal of native oxide by etching. In this example, the strength of the bond created between the elastomer component and the nonelastomer component has been observed to exceed the materials strength of the elastomer components.

14. Cell Pen/Cell Cage

In yet a further application of the present invention, an elastomeric structure can be utilized to manipulate organisms or other biological material. FIGS. 26A-26D show plan views of one embodiment of a cell pen structure in accordance with the present invention.

Cell pen array 4400 features an array of orthogonally-oriented flow channels 4402, with an enlarged "pen" structure 4404 at the intersection of alternating flow channels. Valve 4406 is positioned at the entrance and exit of each pen structure 4404. Peristaltic pump structures 4408 are positioned on each horizontal flow channel and on the vertical flow channels lacking a cell pen structure.

Figure 26C:
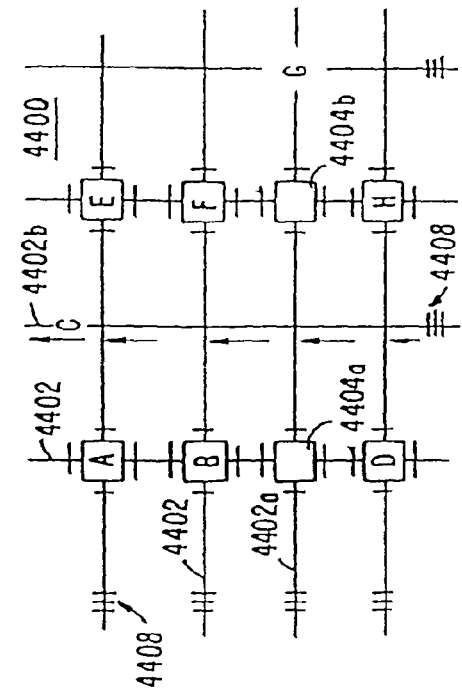
FIGS. 26A-26D show plan views illustrating operation of one embodiment of a cell pen structure in accordance with the present invention.
Figure 26D:
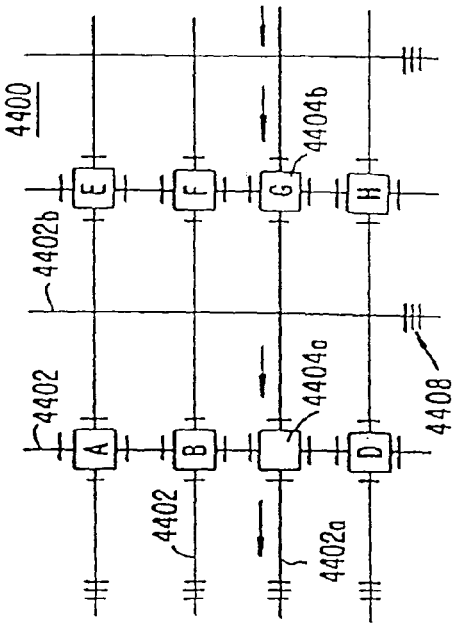
Figure 26A:
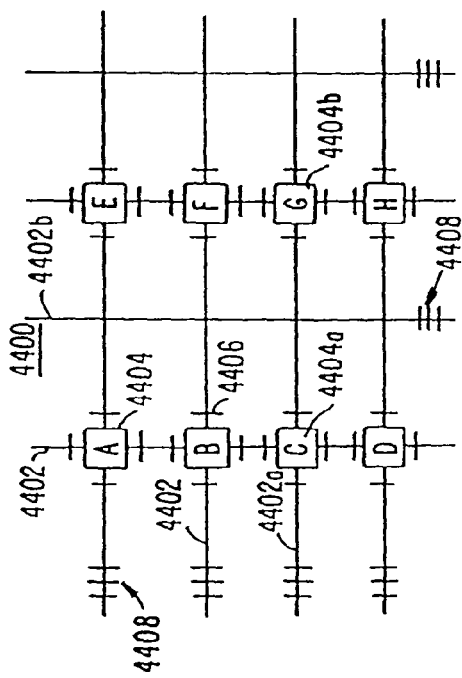
Figure 26B:
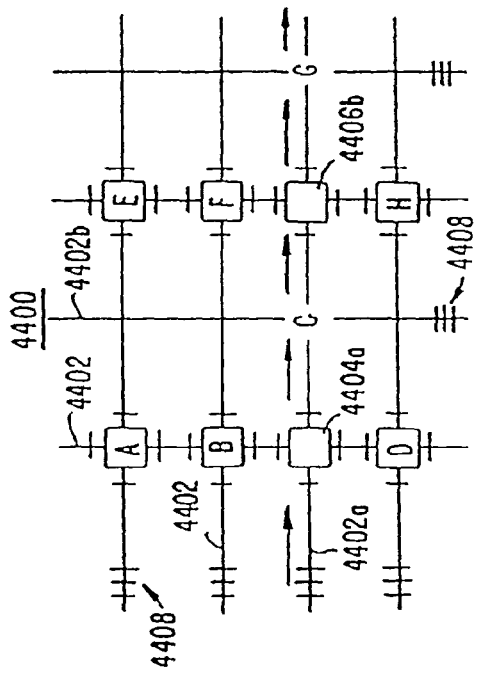

Cell pen array 4400 of FIG. 26A has been loaded with cells A-H that have been previously sorted. FIGS. 26B-26C show the accessing and removal of individually stored cell C by 1) opening valves 4406 on either side of adjacent pens 4404a and 4404b, 2) pumping horizontal flow channel 4402a to displace cells C and G, and then 3) pumping vertical flow channel 4402b to remove cell C. FIG. 26D shows that second cell G is moved back into its prior position in cell pen array 4400 by reversing the direction of liquid flow through horizontal flow channel 4402a.

The cell pen array 4404 described above is capable of storing materials within a selected, addressable position for ready access. However, living organisms such as cells may require a continuous intake of foods and expulsion of wastes in order to remain viable. Accordingly, FIGS. 27A and 27B show plan and cross-sectional views (along line 45B-45B') respectively, of one embodiment of a cell cage structure in accordance with the present invention.

Cell cage 4500 is formed as an enlarged portion 4500a of a flow channel 4501 in an elastomeric block 4503 in contact with substrate 4505. Cell cage 4500 is similar to an individual cell pen as described above in FIGS. 26A-26D, except that ends 4500b and 4500c of cell cage 4500 do not completely enclose interior region 4500a. Rather, ends 4500a and 4500b of cage 4500 are formed by a plurality of retractable pillars 4502. Pillars 4502 may be part of a membrane structure of a normally-closed valve structure as described extensively above in connection with FIGS. 21A-21J.

Specifically, control channel 4504 overlies pillars 4502. When the pressure in control channel 4504 is reduced, elastomeric pillars 4502 are drawn upward into control channel 4504, thereby opening end 4500b of cell cage 4500 and permitting a cell to enter. Upon elevation of pressure in control channel 4504, pillars 4502 relax downward against substrate 4505 and prevent a cell from exiting cage 4500.

Elastomeric pillars 4502 are of a sufficient size and number to prevent movement of a cell out of cage 4500, but also include gaps 4508 which allow the flow of nutrients into cage interior 4500a in order to sustain cell(s) stored therein. Pillars 4502 on opposite end 4500c are similarly configured beneath second control channel 4506 to permit opening of the cage and removal of the cell as desired.

The cross-flow channel architecture illustrated shown in FIGS. 26A-26D can be used to perform functions other than the cell pen just described. For example, the cross-flow channel architecture can be utilized in mixing applications.

Figure 28A:
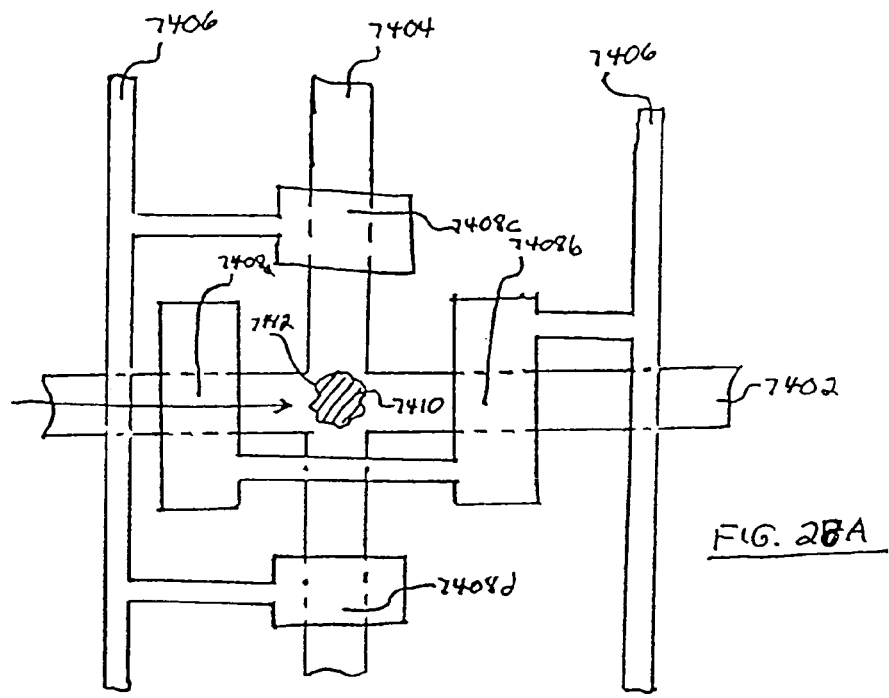
FIGS. 28A-28B show plan views of operation of a wiring structure utilizing cross-channel injection in accordance with the embodiment of the present invention.
Figure 28B:
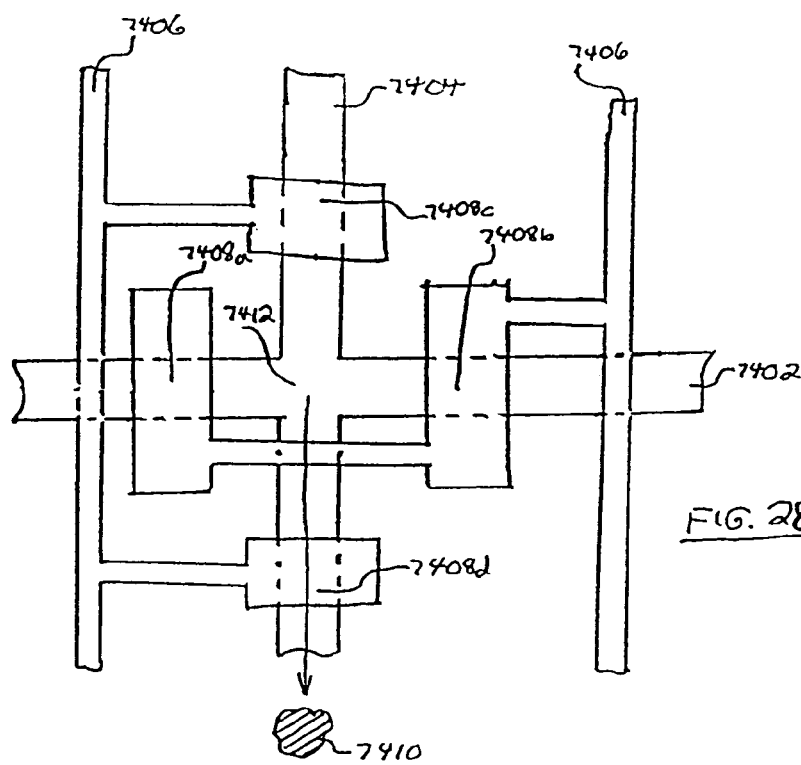

This is shown in FIGS. 28A-B, which illustrate a plan view of mixing steps performed by a microfabricated structure in accordance another embodiment of the present invention. Specifically, portion 7400 of a microfabricated mixing structure comprises first flow channel 7402 orthogonal to and intersecting with second flow channel 7404. Control channels 7406 overlie flow channels 7402 and 7404 and form valve pairs 7408a-b and 7408c-d that surround each intersection 7412.

As shown in FIG. 28A, valve pair 7408a-b is initially opened while valve pair 7408c-d is closed, and fluid sample 7410 is flowed to intersection 7412 through flow channel 7402. Valve pair 7408c-d is then actuated, trapping fluid sample 7410 at intersection 7412.

Next, as shown in FIG. 28B, valve pairs 7408a-b and 7408c-d are opened, such that fluid sample 7410 is injected from intersection 7412 into flow channel 7404 bearing a cross-flow of fluid. The process shown in FIGS. 28A-B can be repeated to accurately dispense any number of fluid samples down cross-flow channel 7404.

While the embodiment shown and described above in connection with FIGS. 28A-28B utilizes linked valve pairs on opposite sides of the flow channel intersections, this is not required by the present invention. Other configurations, including linking of adjacent valves of an intersection, or independent actuation of each valve surrounding an intersection, are possible to provide the desired flow characteristics. With the independent valve actuation approach however, it should be recognized that separate control structures would be utilized for each valve, complicating device layout.

15. Metering by Volume Exclusion

Many high throughput screening and diagnostic applications call for accurate combination of different reagents in a reaction chamber. Given that it is frequently necessary to prime the channels of a microfluidic device in order to ensure fluid flow, it may be difficult to ensure mixed solutions do not become diluted or contaminated by the contents of the reaction chamber prior to sample introduction.

Volume exclusion is one technique enabling precise metering of the introduction of fluids into a reaction chamber. In this approach, a reaction chamber may be completely or partially emptied prior to sample injection. This method reduces contamination from residual contents of the chamber contents, and may be used to accurately meter the introduction of solutions in a reaction chamber.

Figure 29A:
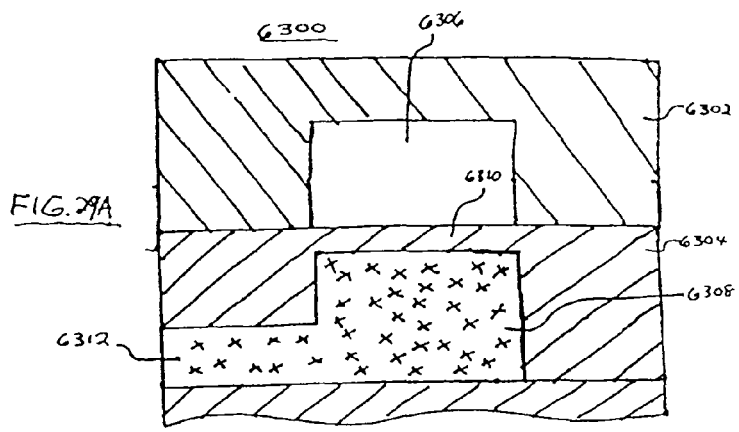
FIGS. 29A-29D illustrate cross-sectional views of metering by volume exclusion in accordance with an embodiment of the present invention.

Specifically, FIGS. 29A-29D show cross-sectional views of a reaction chamber in which volume exclusion is employed to meter reactants. FIG. 29A shows a cross-sectional view of portion 6300 of a microfluidic device comprising first elastomer layer 6302 overlying second elastomer layer 6304. First elastomer layer 6302 includes control chamber 6306 in fluid communication with a control channel (not shown). Control chamber 6306 overlies and is separated from dead-end reaction chamber 6308 of second elastomer layer 6304 by membrane 6310. Second elastomer layer 6304 further comprises flow channel 6312 leading to dead-end reaction chamber 6308.

Figure 29B:
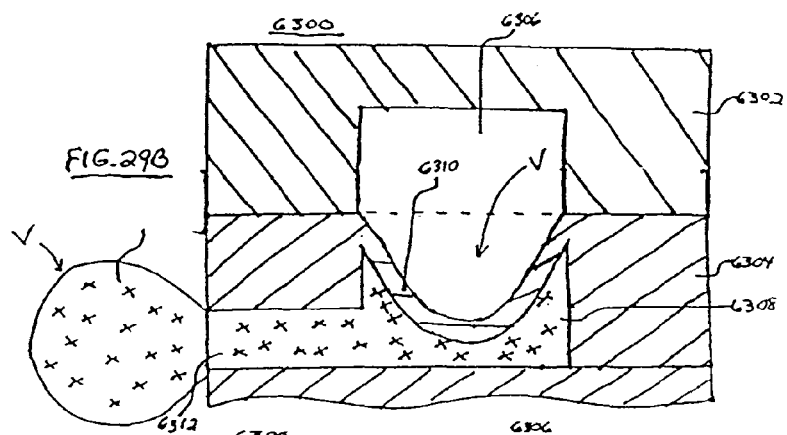

FIG. 29B shows the result of a pressure increase within control chamber 6306. Specifically, increased control chamber pressure causes membrane 6310 to flex downward into reaction chamber 6308, reducing by volume V the effective volume of reaction chamber 6308. This in turn excludes an equivalent volume V of reactant from reaction chamber 6308, such that volume V of first reactant X is output from flow channel 6312. The exact correlation between a pressure increase in control chamber 6306 and the volume of material output from flow channel 6312 can be precisely calibrated.

Figure 29C:
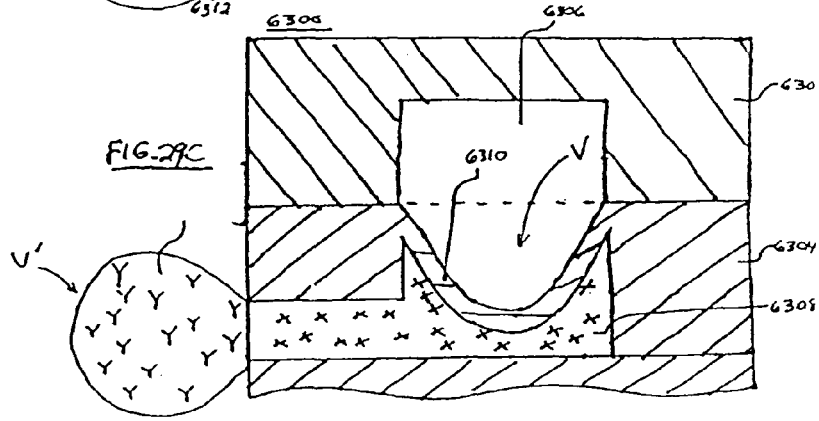

As shown in FIG. 29C, while elevated pressure is maintained within control chamber 6306, volume V' of second reactant Y is placed into contact with flow channel 6312 and reaction chamber 6308.

Figure 29D:
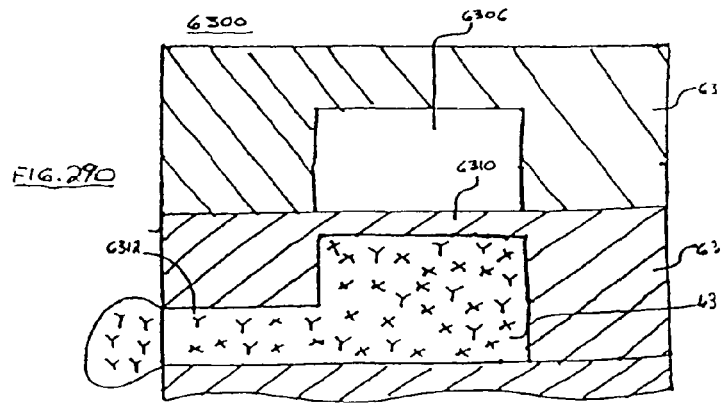

In the next step shown in FIG. 29D, pressure within control chamber 6306 is reduced to original levels. As a result, membrane 6310 relaxes and the effective volume of reaction chamber 6308 increases. Volume V of second reactant Y is sucked into the device. By varying the relative size of the reaction and control chambers, it is possible to accurately mix solutions at a specified relative concentration. It is worth noting that the amount of the second reactant Y that is sucked into the device is solely dependent upon the excluded volume V, and is independent of volume V' of Y made available at the opening of the flow channel.

While FIGS. 29A-29D show a simple embodiment of the present invention involving a single reaction chamber, in more complex embodiments parallel structures of hundreds or thousands of reaction chambers could be actuated by a pressure increase in a single control line.

Moreover, while the above description illustrates two reactants being combined at a relative concentration that fixed by the size of the control and reaction chambers, a volume exclusion technique could be employed to combine several reagents at variable concentrations in a single reaction chamber. One possible approach is to use several, separately addressable control chambers above each reaction chamber. An example of this architecture would be to have ten separate control lines instead of a single control chamber, allowing ten equivalent volumes to be pushed out or sucked in.

Another possible approach would utilize a single control chamber overlying the entire reaction chamber, with the effective volume of the reaction chamber modulated by varying the control chamber pressure. In this manner, analog control over the effective volume of the reaction chamber is possible. Analog volume control would in turn permit the combination of many solutions reactants at arbitrary relative concentrations.

An embodiment of a method of metering a volume of fluid in accordance with the present invention comprises providing a chamber having a volume in an elastomeric block separated from a control recess by an elastomeric membrane, and supplying a pressure to the control recess such that the membrane is deflected into the chamber and the volume is reduced by a calibrated amount, thereby excluding from the chamber the calibrated volume of fluid.

16. Sorting

The present microfluidic pumps and valves can also e used in flow cytometers for cell sorting and DNA sizing. Sorting of objects based upon size is extremely useful in many technical fields.

For example, many assays in biology require determination of the size of molecular-sized entities. Of particular importance is the measurement of length distribution of DNA molecules in a heterogeneous solution. This is commonly done using gel electrophoresis, in which the molecules are separated by their differing mobility in a gel matrix in an applied electric field, and their positions detected by absorption or emission of radiation. The lengths of the DNA molecules are then inferred from their mobility.

While powerful, electrophoretic methods pose disadvantages. For medium to large DNA molecules, resolution, i.e. the minimum length difference at which different molecular lengths may be distinguished, is limited to approximately 10% of the total length. For extremely large DNA molecules, the conventional sorting procedure is not workable. Moreover, gel electrophoresis is a relatively lengthy procedure, and may require on the order of hours or days to perform.

The sorting of cellular-sized entities is also an important task. Conventional flow cell sorters are designed to have a flow chamber with a nozzle and are based on the principle of hydrodynamic focusing with sheath flow. Most conventional cell sorters combine the technology of piezo-electric drop generation and electrostatic deflection to achieve droplet generation and high sorting rates. However, this approach offers some important disadvantages. One disadvantage is that the complexity, size, and expense of the sorting device requires that it be reusable in order to be cost-effective. Reuse can in turn lead to problems with residual materials causing contamination of samples and turbulent fluid flow.

Therefore, there is a need in the art for a simple, inexpensive, and easily fabricated sorting device which relies upon the mechanical control of fluid flow rather than upon electrical interactions between the particle and the solute.

Figure 30:
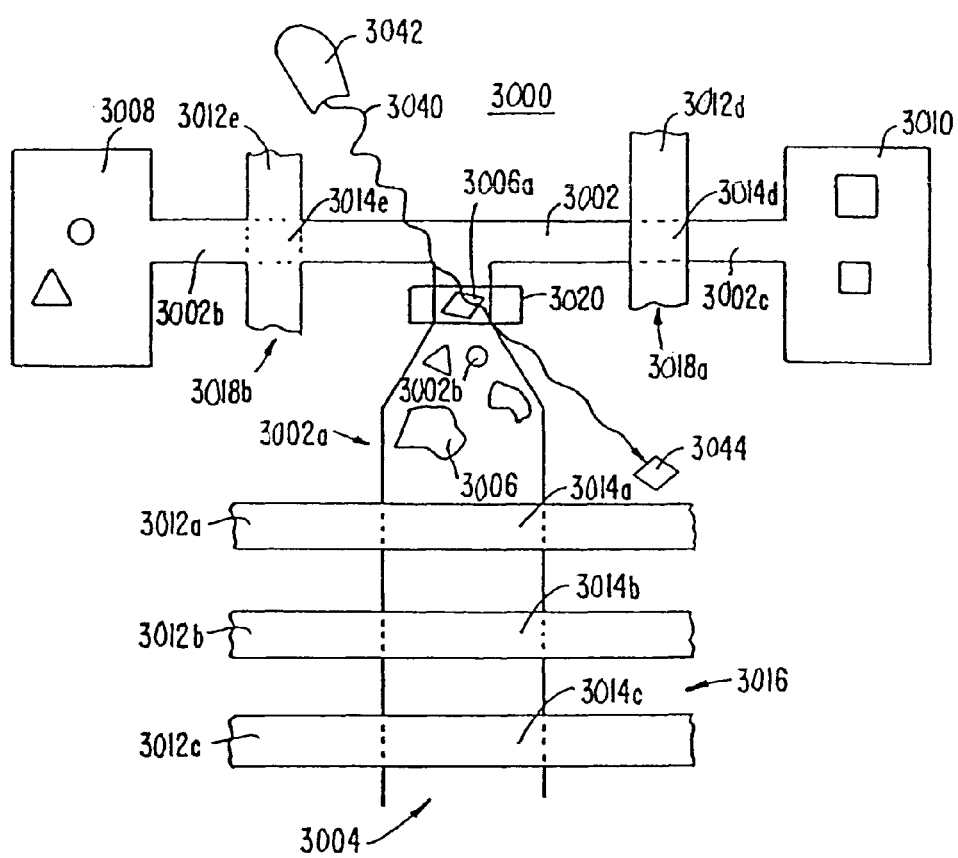
FIG. 30 illustrates a plan view of one embodiment of a sorting device in accordance with the present invention.

FIG. 30 shows one embodiment of a sorting device in accordance with the present invention. Sorting device 3000 is formed from a switching valve structure created from channels present in an elastomeric block. Specifically, flow channel 3002 is T-shaped, with stem 3002a of flow channel 3002 in fluid communication with sample reservoir 3004 containing sortable entities 3006 of different types denoted by shape (square, circle, triangle, etc.). Left branch 3002b of flow channel 3002 is in fluid communication with waste reservoir 3008. Right branch 3002c of flow channel 3002 is in communication with collection reservoir 3010.

Control channels 3012a, 3012b, and 3012c overlie and are separated from stem 3002a of flow channel 3002 by elastomeric membrane portions 3014a, 3014b, and 3014c respectively. Together, stem 3002a of flow channel 3002 and control channels 3012a, 3012b, and 3012c form first peristaltic pump structure 3016 similar to that described at length above.

Control channel 3012d overlies and is separated from right branch 3002c of flow channel 3002 by elastomeric membrane portion 3014d. Together, right branch 3002c of flow channel 3002 and control channels 3012d forms first valve structure 3018a. Control channel 3012e overlies and is separated from left branch 3002c of flow channel 3002 by elastomeric membrane portion 3014e. Together, left branch 3002c of flow channel 3002 and control channel 3012e forms second valve structure 3018b.

As shown in FIG. 30, stem 3602a of flow channel 3002 narrows considerably as it approaches detection window 3020 adjacent to the junction of stem 3002a, right branch 3002b, and left branch 3002c. Detection window 3020 is of sufficient width to allow for uniform illumination of this region. In one embodiment, the width of the stem narrows from 100 µm to 5 µm at the detection window. The width of the stem at the detection window can be precisely formed using the soft lithography or photoresist encapsulation fabrication techniques described extensively above, and will depend upon the nature and size of the entity to be sorted.

Operation of sorting device in accordance with one embodiment of the present invention is as follows.

The sample is diluted to a level such that only a single sortable entity would be expected to be present in the detection window at any time. Peristaltic pump 3016 is activated by flowing a fluid through control channels 3012a-c as described extensively above. In addition, second valve structure 3018b is closed by flowing fluid through control channel 3012e. As a result of the pumping action of peristaltic pump 3016 and the blocking action of second valve 3018b, fluid flows from sample reservoir 3004 through detection window 3020 into waste reservoir 3008. Because of the narrowing of stem 3004, sortable entities present in sample reservoir 3004 are carried by this regular fluid flow, one at a time, through detection window 3020.

Radiation 3040 from source 3042 is introduced into detection window 3020. This is possible due to the transmissive property of the elastomeric material. Absorption or emission of radiation 3040 by sortable entity 3006 is then detected by detector 3044.

If sortable entity 3006a within detection window 3020 is intended to be segregated and collected by sorting device 3000, first valve 3018a is activated and second valve 3018b is deactivated. This has the effect of drawing sortable entity 3006a into collection reservoir 3010, and at the same time transferring second sortable entity 3006b into detection window 3020. If second sortable entity 3002b is also identified for collection, peristaltic pump 3016 continues to flow fluid through right branch 3602c of flow channel 3002 into collection reservoir 3610. However, if second entity 3006b is not to be collected, first valve 3018a opens and second valve 3018b closes, and first peristaltic pump 3016 resumes pumping liquid through left branch 3002b of flow channel 3002 into waste reservoir 3008.

While one specific embodiment of a sorting device and a method for operation thereof is described in connection with FIG. 30, the present invention is not limited to this embodiment. For example, fluid need not be flowed through the flow channels using the peristaltic pump structure, but could instead be flowed under pressure with the elastomeric valves merely controlling the directionality of flow. In yet another embodiment, a plurality of sorting structures could be assembled in series in order to perform successive sorting operations, with the waste reservoir of FIG. 36 simply replaced by the stem of the next sorting structure.

Moreover, a high throughput method of sorting could be employed, wherein a continuous flow of fluid from the sample reservoir through the window and junction into the waste reservoir is maintained until an entity intended for collection is detected in the window. Upon detection of an entity to be collected, the direction of fluid flow by the pump structure is temporarily reversed in order to transport the desired particle back through the junction into the collection reservoir. In this manner, the sorting device could utilize a higher flow rate, with the ability to backtrack when a desired entity is detected. Such an alternative high throughput sorting technique could be used when the entity to be collected is rare, and the need to backtrack infrequent.

Sorting in accordance with the present invention would avoid the disadvantages of sorting utilizing conventional electrokinetic flow, such as bubble formation, a strong dependence of flow magnitude and direction on the composition of the solution and surface chemistry effects, a differential mobility of different chemical species, and decreased viability of living organisms in the mobile medium.

II. Structures and Methods For Electronic Detection

As just described, embodiments of microfluidic structures in accordance with the present invention may contain a variety of materials for sorting or other purposes. In order to detect the presence and identity of such a detectable entity at particular locations within the microfluidic devices, changes in the electric or magnetic environment may be monitored.

For purposes of this application, the term detectable entity includes but is not limited to, white and red blood cells, bacteria, viral particles, macromolecules such as proteins (or protein subunits) and nucleic acids (or fragments thereof), polymer (e.g. latex) beads, inorganic microparticles or nanoparticles. A detectable entity can also comprise a change in the nature of the contents of the flow channel, such that one portion can be distinguished electrically from another portion.

Certain embodiments in accordance with the present invention rely upon electronic-based detection schemes. Specifically, an electric field is applied to a detection region within a microfabricated elastomeric structure. When a detectable entity enters the detection region, the electrical properties of the detectable entity alter the electrical environment of the detection region. This changed electrical environment may alter the electric field, may generate an electrical current resulting from application of the electric field, or may result in both generating a current and altering the electric field. The presence of the detected entity may thus be revealed by monitoring the changed voltages or currents.

Other embodiments in accordance with the present invention rely upon magnetic-based detection schemes. Specifically, as a detectable entity enters a detection region, the magnetic properties of the detectable entity alter the magnetic environment of the detection region. This changed magnetic environment may induce a current in a nearby coil, or may change resistance of a nearby magnetoresistive element. The presence of the detected entity may thus be revealed by monitoring these voltages and/or currents.

An embodiment of a method of detecting an entity in a microfabricated elastomeric structure comprises defining a detection volume within the microfabricated elastomeric structure, the detection volume receiving one detectable entity or ensemble of detected entities at a time. An electric field is applied to the detection volume, and a change in one of an impedance and a current of the detection volume is measured as the detectable entity traverses the detection volume.

1. Electronic Based Sensing

The electrical properties of the sample within the detection volume can be described in many equivalent ways. In the instant application, the term impedance is employed to encompass the concepts of both resistance and capacitance.

In one embodiment of an electronic-based detection method in accordance with the present invention, an electric field is applied transverse to a direction of flow of the detectable entity in the detection region, such that a change in impedance is observed as the detectable entity passes through the detection region. One prior application of a similar technique is described by Sohn et al. in "Capacitance cytometry: Measuring biological cells one by one," Proceedings of the National Academy of Sciences, 97, 20, 10687-10690, (2000), incorporated by reference for all purposes herein. As with this reference, detectable entities in the form of cellular material may be detected by embodiments in accordance with the present invention.

Figure 31A:
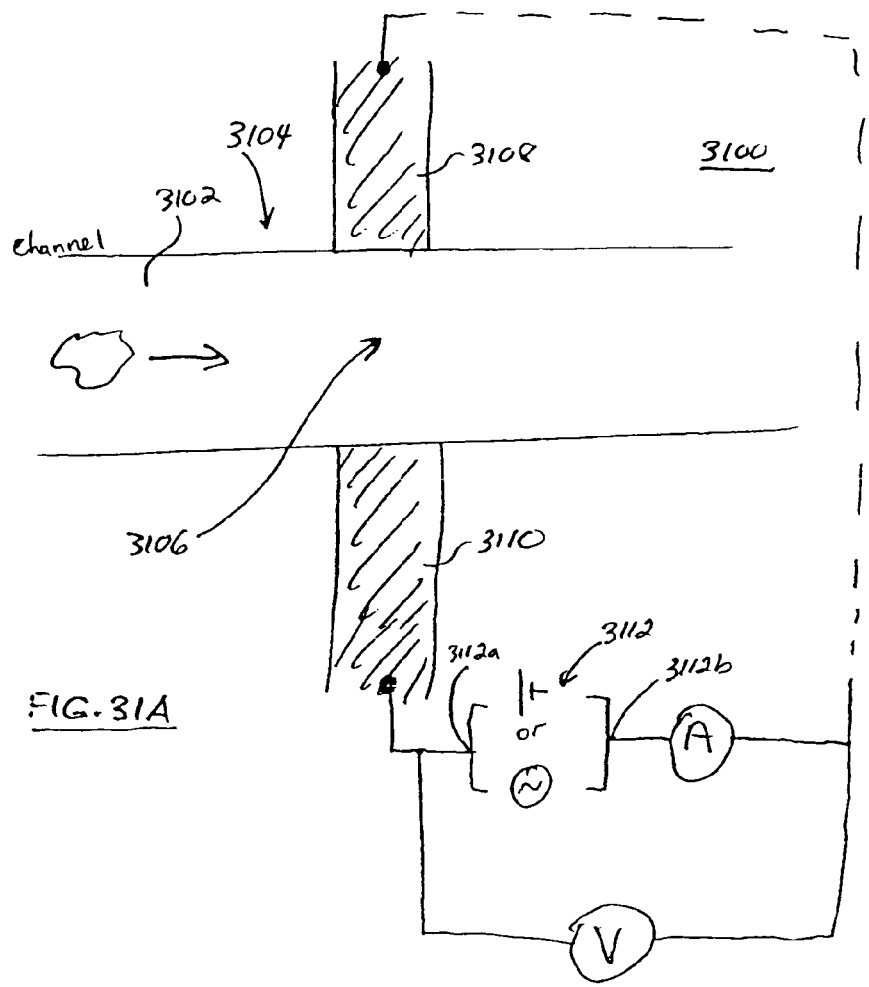
FIG. 31A shows a simplified plan view of the detection region of an embodiment of a "transverse" electronic-based detection apparatus in accordance with the present invention.

FIG. 31A shows a simplified plan view of the detection region of an embodiment of such a "transverse" electronic-based detection apparatus in accordance with the present invention. Specifically, detector 3100 comprises flow channel 3102 formed in elastomeric layer 3104. Electrodes 3108 and 3110 are disposed on opposite sides of flow channel 3102 to define detection region 3106 sufficiently small as to allow only one detectable entity 3111 to pass through at a time. Electrodes 3108 and 3110 need not extend across the entire width or height of the flow channel.

Operation of detector 3100 is as follows. A solution containing a detectable entity 3111 is flowed down flow channel 3102 and through detection region 3206. Electrodes 3108 and 3110 are placed into contact with terminals 3112a and 3112b of AC power supply 3112. The frequency of oscillation of the AC power supply relative to the flow rate would be chosen to be high enough as to allow detection of the passage of an entity entrained in the fluid flowing between the electrodes.

As a result of their orientation, electrodes 3108 and 3110 apply an electric field in a direction transverse to the flow of materials through detection region 3106. Application of a potential difference across electrodes 3108 and 3110 creates a capacitor structure having as plates electrodes 3108 and 3110, and having the contents of the flow channel as a dielectric. The capacitance exhibited by this electrode/flow channel capacitor structure, and hence the voltage between the electrodes, remains constant as solute flows through.

However, as a detectable entity 3111 passes between electrodes 3108 and 3110, the dielectric properties of the electrode/flow channel capacitor change. Depending upon the electrical conductivity and permittivity of detectable entity 3111, capacitance (and also resistance) of the electrode/flow channel capacitor structure may either rise or fall, resulting in a change in voltage across electrodes 3108 and 3110.

The change in voltage just described may be correlated with the presence and/or identity of a detected entity within the flow channel. By monitoring voltage change signals over time, the number of detectable entities passing through the detection region can be counted. In addition, information on the size, orientation, and electrical properties of the detectable entities may simultaneously be obtained.

Figure 31B:
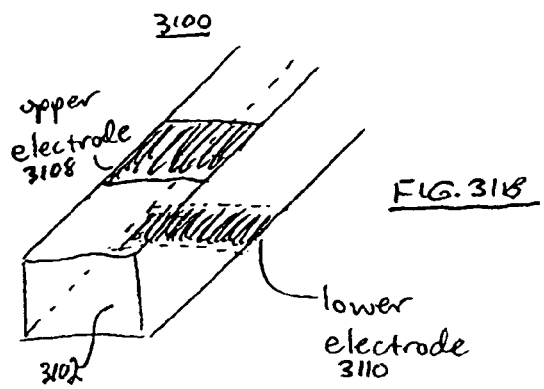
FIGS. 31B-C show perspective views of alternative embodiments of detection regions of a "transverse" electronic-based detection apparatuses.
Figure 31C:
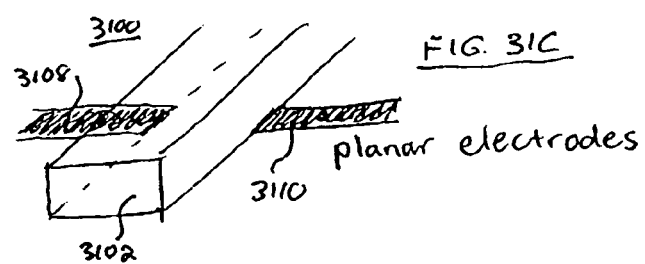

The present invention is not limited to the embodiment shown in FIG. 31a. FIGS. 31B-D show perspective views of alternative embodiments of detection regions of a "transverse" electronic-based detection apparatuses. The embodiment shown in FIG. 31B features opposed electrodes positioned in the floor and ceiling of the flow channel. The embodiment shown in FIG. 31C features opposed electrodes positioned in a plane of the floor of the flow channel.

While FIG. 31A shows the electrodes in communication with an AC voltage source, in an alternative embodiment an electric field could be utilized to pass a constant electrical current across the detection region. When a detected entity is present therein, an increase in electric field required to maintain the original current level could be measured.

In an alternative embodiment of an electronic-based detection method in accordance with the present invention, an electric field is applied parallel to a direction of flow of the detectable entity in the detection region, such that a change in impedance is observed as the detectable entity passes through the detection region.

Figure 32:
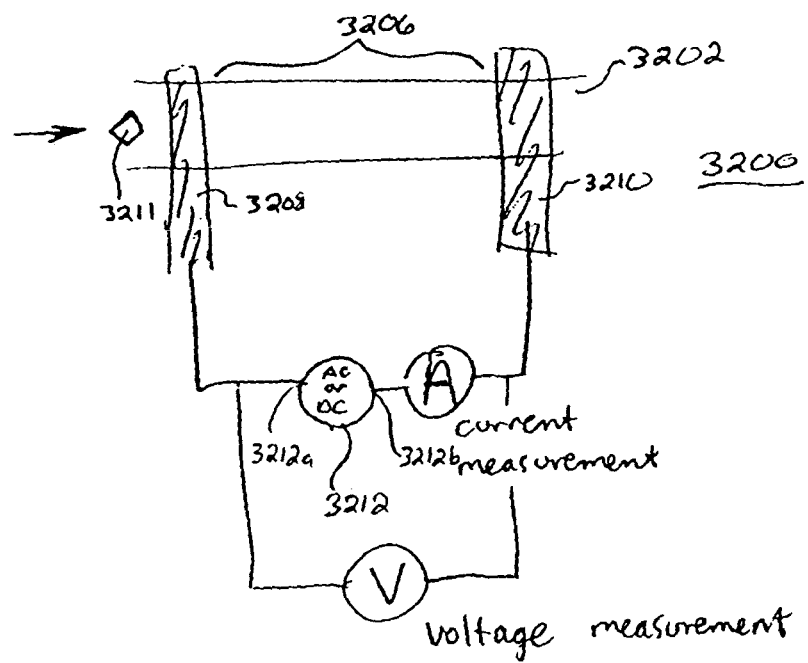
FIG. 32 shows a simplified plan view of the detection region of an embodiment of a "longitudinal" electronic-based detection apparatus in accordance with the present invention.

FIG. 32 shows a simplified plan view of the detection region of an embodiment of such a "longitudinal" electronic-based detection apparatus in accordance with the present invention. Detector 3200 operates according to the well-known Coulter Principle.

Specifically, flow channel 3202 is formed in elastomeric layer 3104. Electrodes 3208 and 3210 are disposed adjacent to flow channel 3102 to define detection region 3206 between them. Detection region 3206 is sufficiently small as to allow only one detectable entity 3211 to pass through at a time, and the flow channel is not necessarily straight, or of constant width, throughout the entire detection region. Electrodes 3208 and 3210 need not extend across the entire width or height of the flow channel.

Operation of detector 3200 is as follows. A solution containing a detectable entity 3211 is flowed down flow channel 3202 and through detection region 3206. Electrodes 3208 and 3210 are placed into contact with terminals 3212a and 3212b of AC power supply 3212. The frequency of oscillation of the AC power supply relative to the flow rate would be chosen to be high enough as to allow detection of the passage of an entity entrained in the fluid flowing between the electrodes.

As a result of their orientation, electrodes 3208 and 3210 apply an electric field in a direction parallel to the flow of materials through detection region 3206. Where only solvent is present in detection region 3206, the potential difference across electrodes 3208 and 3210 gives rise to a current flow of a given magnitude. However, this current flow changes when detectable entity 3211 enters detection region 3206. Specifically, the presence of detectable entity 3211 within detection region 3206 alters the continuous conductive path between electrodes 3208 and 3210 through solute within detection region 3206. As a result of this change in conductivity of the current path between electrodes 3208 and 3210, the amount of current passing between the electrodes changes.

Where the detectable entity exhibits an electrical conductivity that is greater than the solute, the current passing between the electrodes may increase. Where the detectable entity exhibits an electrical conductivity that is less than the solute, the current passing between the electrodes may decrease.

While FIG. 32 shows the electrodes in communication with an AC voltage source, in an alternative embodiment an electric field could be utilized to pass a constant electrical current along the detection region. When a detected entity is present therein, an increase in electric field required to maintain the original current level could be measured.

The changes in electrical properties just described may be correlated with the presence and identity of one or more detected entities within the constriction. By monitoring current between the electrodes, over time the number of entities passing through the constriction can be counted. In addition, by correlating the magnitude of the change in voltage or current with the characteristics of the detectable entity, information regarding the size, orientation, and electrical properties of the detectable entities may simultaneously be obtained. The size and orientation of the detected entities can often be obtained with minimal computation, as can the rate of flow through the detection region. In addition, electrical properties such as conductivity and permittivity of the detected entities influence the data, and can therefore be inferred.

The longitudinal sensing architecture described in FIG. 32 may be utilized to sense the state of a microfluidic valve/pump structure. In such an embodiment, electrodes could be positioned along the flow channel on opposite sides of the valve. Application of potential difference between the electrodes could reveal not only whether or not the valve is open or closed, but also the degree of openness of the valve.

For example, if a potential difference is applied where the valve is shut, no conductive path exists between the electrodes and no current will flow if a potential difference is applied. Where the valve is partially shut, conductive solute would be excluded from a portion of the detectable region, altering the current through that region. In such an embodiment, the detectable entity would in fact be the valve/pump membrane.

FIGS. 31 and 32 illustrate particular embodiments of transverse and longitudinal type electronic detectors in accordance with the present invention. However, the present invention is not limited to these particular configurations, and other embodiments will be apparent to those of skill in the art.

For example, where a conductive member is in direct contact with the contents of the flow (as in the embodiments of FIGS. 31 and 32), charged species in the solute may accumulate at the conductive member. This accumulation of ions can reduce the effective magnitude of the electrical field applied across the detection region, reducing sensitivity of the detector and complicating measurement of changes in electrical characteristics.

Figure 33A:
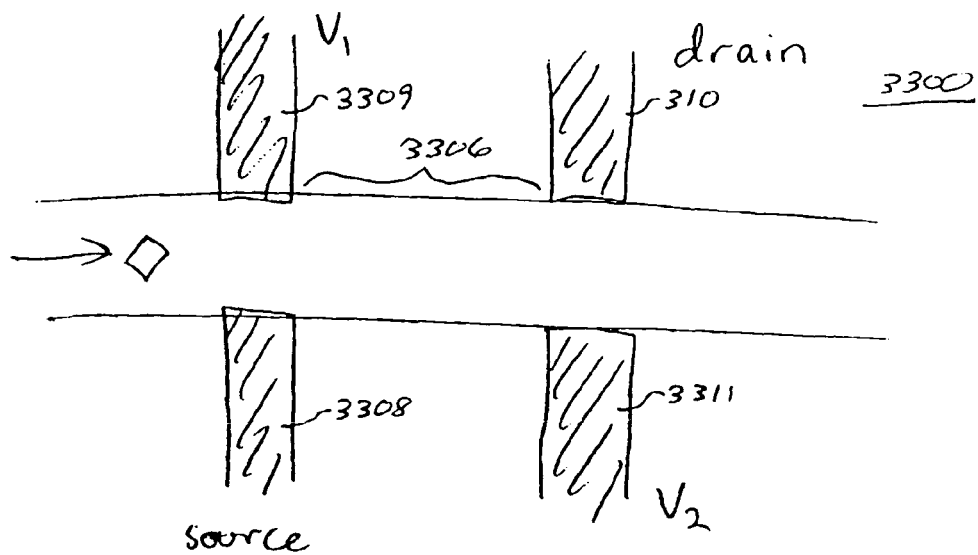
FIG. 33A shows a simplified plan view of an alternative embodiment of a "transverse" electronic-based detection apparatus in accordance with the present invention.
Figure 33B:
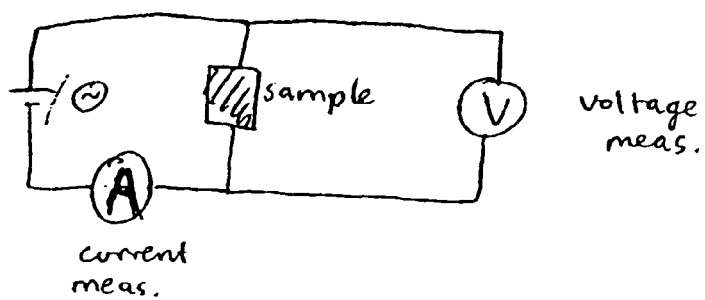
FIG. 33B shows a schematic diagram of the circuit formed by the apparatus of FIG. 33A.

One way to avoid the effect of accumulation of charged species is to employ different electrodes for application of the electric field and for sensing. Accordingly, FIG. 33A shows a plan view of an alternative embodiment of a "transverse" electronic-based detection apparatus in accordance with the present invention. FIG. 33B shows a schematic diagram of the circuit formed by the apparatus of FIG. 33A.

Detector 3300 is similar to that shown in FIG. 31, except that four electrodes 3308, 3309, 3310, and 3311 are utilized. An electric field is applied to detection region 3306 as described above via electrodes 3308 and 3310, which function as a source and drain of electrical current.

Additional pair of "sensing" electrodes 3309 and 3311 are used to independently measure the electric field in the detection region 3306. The magnitude of the sensing voltage is lower than the voltage applied across the entire device. Because the voltage sensing electrodes do not supply or draw a significant current, sensing electrodes 3309 and 3311 experience little or no significant ion accumulation effect.

Figure 34:
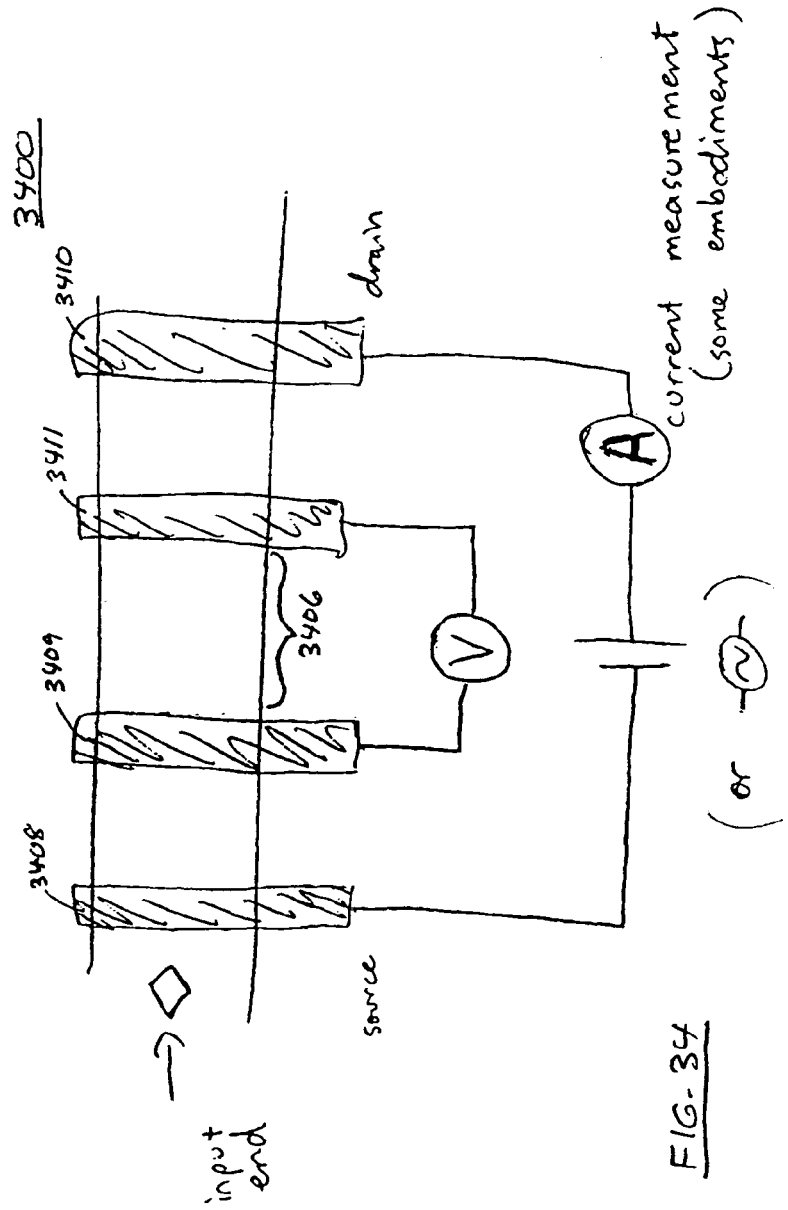
FIG. 34 shows a simplified plan view of an alternative embodiment of a "longitudinal" electronic-based detection apparatus in accordance with the present invention.

Similarly, FIG. 34 shows a plan view of an alternative embodiment of a "longitudinal" electronic-based detection apparatus in accordance with the present invention. Detector 3400 is similar to that shown in FIG. 32, except that four electrodes 3408, 3409, 3410, and 3411 are utilized. An electric field is applied to detection region 3406 as described above via electrodes 3408 and 3410, which function as a source and drain of electrical current. An additional pair of "sensing" electrodes 3409 and 3411 are used to independently measure the electric field in the detection region 3406.

While the above description relates to embodiments of detection structures and methods utilizing four electrodes, other numbers of terminals may be employed. For example, three terminal embodiments operate in manner similar to the four-terminal embodiments described above, except that one terminal serves both to apply the electric field and to detect changes in electrical environment. These functions are segregated between the other two electrodes.

For any of the approaches previously discussed, multiple electrodes can be positioned along the direction of flow. In such embodiments, the space between any two electrodes, adjacent or otherwise, defines a sensing region. Parallel measurements of the electric field distribution along the array can increase the sensitivity of detection, and supply additional information on the properties of detected entities as a function of location, elapsed time, and local conditions within the microfluidic system. Such an embodiment also allows the parallel analysis of multiple different entities, and or tracking or time-dependent analysis of given entities.

In transverse embodiments where multiple pairs of electrodes are employed, at least two electrodes would be positioned on one surface of the flow channel at the detection region, and at least two electrodes would be positioned on an opposing surface at that location. A first pair of electrodes, consisting of at least one electrode on each of these two opposing faces, are used as the source and drain of electrical current, either DC or AC. Two or more additional 'sensing' electrodes, consisting of at least a second electrode on each of the opposing surfaces, are then used to sense the electrical potential across the detection region. External electrical connections would be arranged such these 'sensing' electrodes are electrically distinct from the first pair of electrodes.

Figure 35:
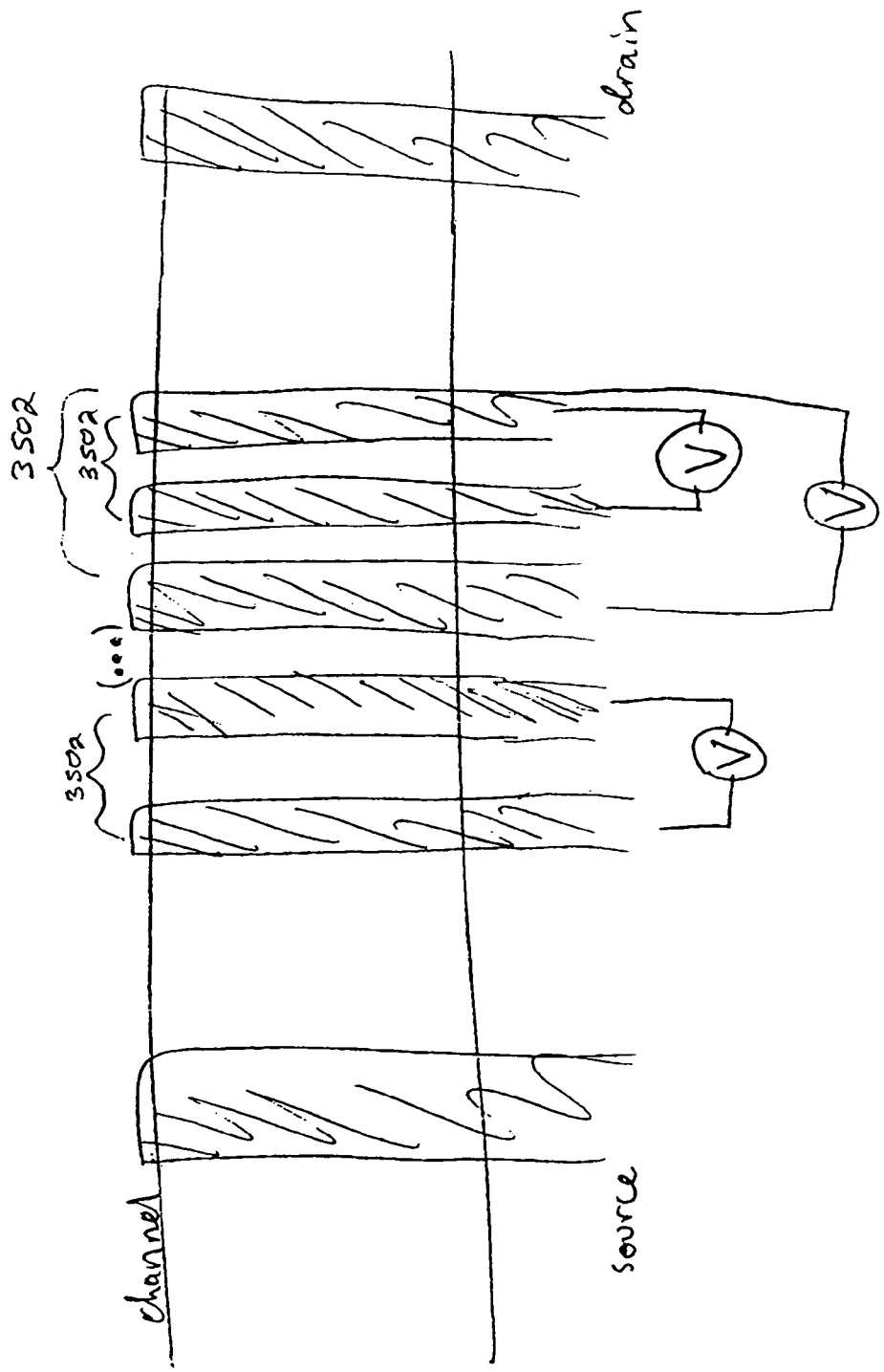
FIG. 35 shows a simplified plan view of another alternative embodiment of a "longitudinal" electronic-based detection apparatus in accordance with the present invention.

FIG. 35 shows a simplified plan view of an alternative embodiment of a longitudinal electronic-type detecting apparatus utilizing multiple electrodes along a flow path. As shown in FIG. 35, detector 3500 includes multiple pairs 3502 of electrodes. In such a longitudinal embodiment, one electrode toward the input end, and one electrode toward the output end are used as the source and drain of electrical current, either DC or AC. At least a second electrode toward either end, electrically distinct from the current source and drain electrodes, are then used to sense the electrical potential across the detection region.

While the embodiments previously described illustrate detection in a flow channel formed in an elastomer, this is not required by the present invention. As described above, embodiments of microfluidic structures in accordance with the present invention may also include flow channels having floors and walls formed in an underlying non-elastomeric substrate such as glass or silicon, with the ceiling of the flow channel formed from an overlying deflectable elastomer layer. Because the dimensions of the flow channels of non-elastomeric materials in such alternative embodiments are easily controlled by lithography, these alternative embodiments are also amenable for use in detecting entities. Moreover, the conductive electrodes could be readily created within or upon the non-elastomeric substrate utilizing techniques such as metal evaporation, sputtering, ion-implantation or chemical vapor deposition.

In addition, while the illustrated embodiments show the electrodes positioned in direct electrical contact with the contents of the flow channel, this is not required. In alternative embodiments in accordance with the present invention, the electrodes may be separated from the flow channel by a dielectric material that is of sufficient thickness to permit an AC electrical field to be applied by the electrodes through the flow channel.

This encapsulation has at least two advantages. First, the impedance measurements become less adversely affected by the presence of incidental ions in the sample solution. Second, the electrodes can become more chemically robust. This enhanced robustness arises from creating a physical barrier to electrochemical reaction between the electrodes and the contents of the flow channel. Encapsulated electrodes may also be more readily cleanable, in applications where solvents or chemical cleaners are employed.

While FIG. 31 shows the electrodes disposed on opposite sides of the flow channel as in communication with an alternating current (AC) power supply, the present invention is not limited to this particular configuration, and other types of power supplies could be used. In an alternative embodiment in accordance with the present invention, a DC power supply could be connected to the electrodes of FIG. 31. In this case, the quantity being measured is resistance rather than capacitance, yet the underlying principle remains the same. An entity is detected and analyzed through its effect on the impedance of the detection volume. In such an embodiment, Coulter-type measurements analogous to the those of FIG. 32 could comprise the mode of detection.

Many useful characteristics of a detectable entity are frequency dependent. Accordingly, in accordance with yet another alternative embodiment of the present invention, the frequency of oscillation of the applied electric field from an AC power supply can be varied during measurement to obtain such frequency dependent information. Possible examples of frequency dependent information include permittivity and conductivity of the detectable entity, and electrical characteristics of the solute.

While the above embodiments portray the electrodes as disposed on walls of the flow channel, embodiments in accordance with the present invention are not so limited. Other electrode configurations are possible, for example placement of electrodes in the flow channel floor and ceiling, or even at a flow channel elbow or curve. One significant advantage of these electronic sensing schemes is that the channel need not be straight, or of constant dimension, over the entire sensing region.

2. Magnetic-Based Sensing

Embodiments in accordance with the present invention discussed so far utilize an applied electric field to detect a change in the electrical environment of a detection region. In accordance with other embodiments, however, a change in the magnetic environment could be detected to reveal the presence of an entity.

Figure 36:
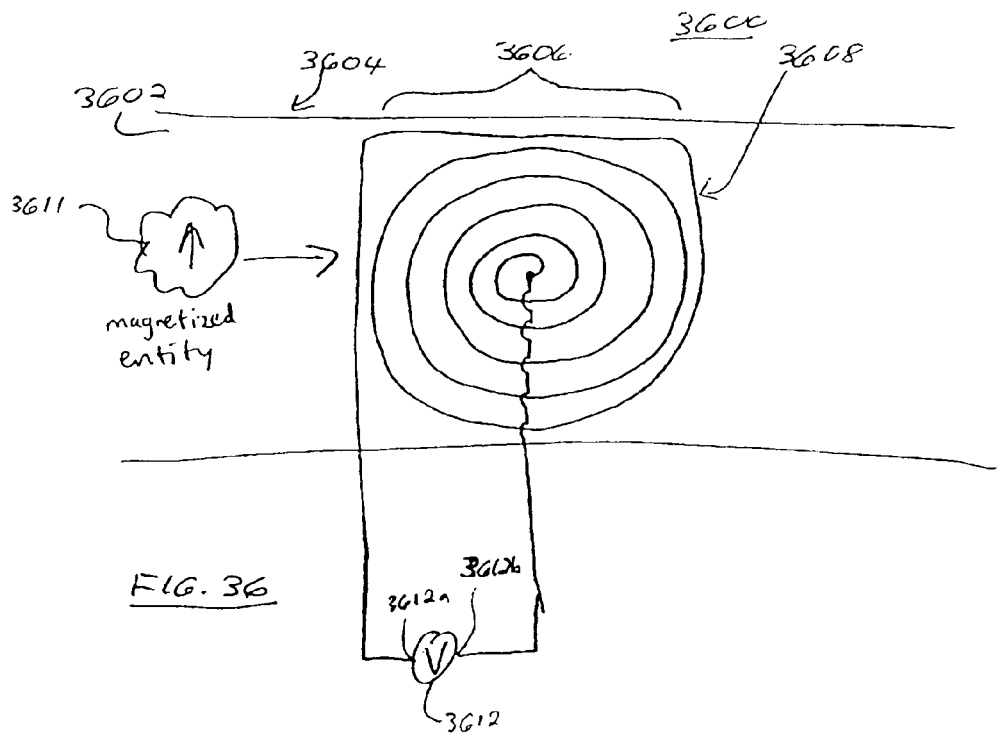
FIG. 36 shows a simplified plan view of an embodiment of a magnetic-based detection apparatus in accordance with the present invention.

FIG. 36 shows a plan view of one embodiment of such a magnetic-based sensing device. Sensor 3600 comprises flow channel 3602 fabricated in elastomeric material 3604. A solution including detectable entity 3611 flows down flow channel 3602 in the direction indicated.

Sensor 3600 also includes planar spiral conducting member 3608 comprising of one or more loops of conductive material, with each end connected to a lead for external measurement. In one embodiment, planar coils are incorporated into one or more surfaces of the flow channel. Spiral conducting member 3608 is positioned proximate to flow channel 3602, either in walls, floor, or ceiling of flow channel 3602. Spiral conducting member 3608 need not be in direct contact with the contents of the flow channel.

As detectable entity 3611 flows past spiral conducting member 3608, its magnetic properties will induce a voltage or current in spiral 3608. These changes may be monitored to detect the presence of a detectable entity within detection region 3606.

Figure 37:
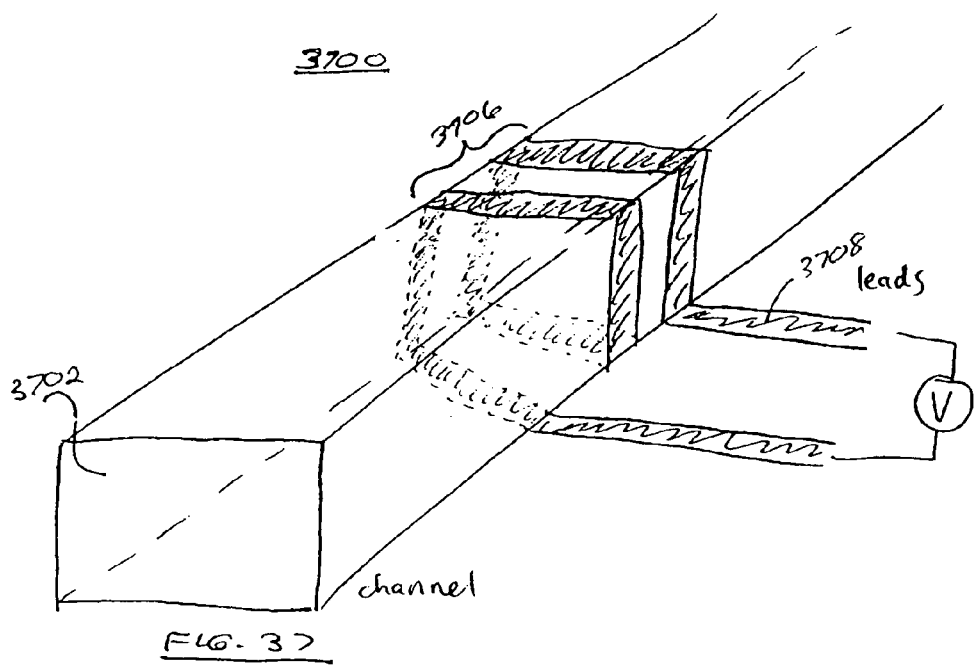
FIG. 37 shows a simplified perspective view of an alternative embodiment of a magnetic-based detection apparatus in accordance with the present invention.

FIG. 37 shows another embodiment of a magnetic-based sensing apparatus in accordance with the present invention. In the embodiment of FIG. 37, detection region 3706 of flow channel 3702 is defined by the presence of nonplanar coaxial conducting member 3708. Passage of a detectable entity having magnetic properties through detection region 3706 may be monitored in the same manner described above for FIG. 36.

For either of the magnetic-based sensing approaches discussed above, detected entities may be intrinsically magnetic, or magnetized temporarily by an external magnetic field applied to the detection region. Such an alternative embodiment would permit detection of specific magnetic properties of the detectable entity, for example paramagnetism, ferromagnetism, and/or diamagnetism.

Figure 38:
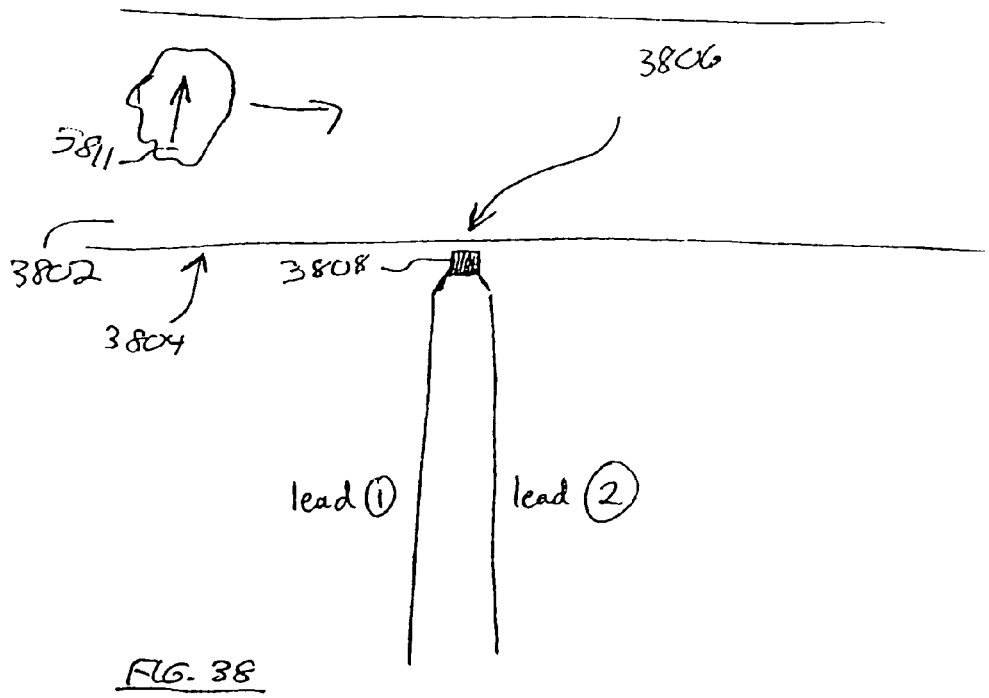
FIG. 38 shows a simplified plan view of another alternative embodiment of a magnetic-based detection apparatus in accordance with the present invention.

Yet another embodiment of a magnetic-based sensor in accordance with the present invention utilizes magnetoresistive principles. Specifically, FIG. 38 illustrates an embodiment of detector 3800 which incorporates a magnetoresistive sensor 3808 at detection region 3806. The electrical resistance exhibited by magnetoresistive sensor 3808 is sensitive to the presence of nearby magnetic fields.

Magnetoresistive sensor 3808 is placed adjacent to, or partially within, flow channel 3802 formed in elastomeric material 3804. Magnetoresistive sensor 3808 can, but need not, be, in direct contact with the contents of the flow channel.

Figure 39:
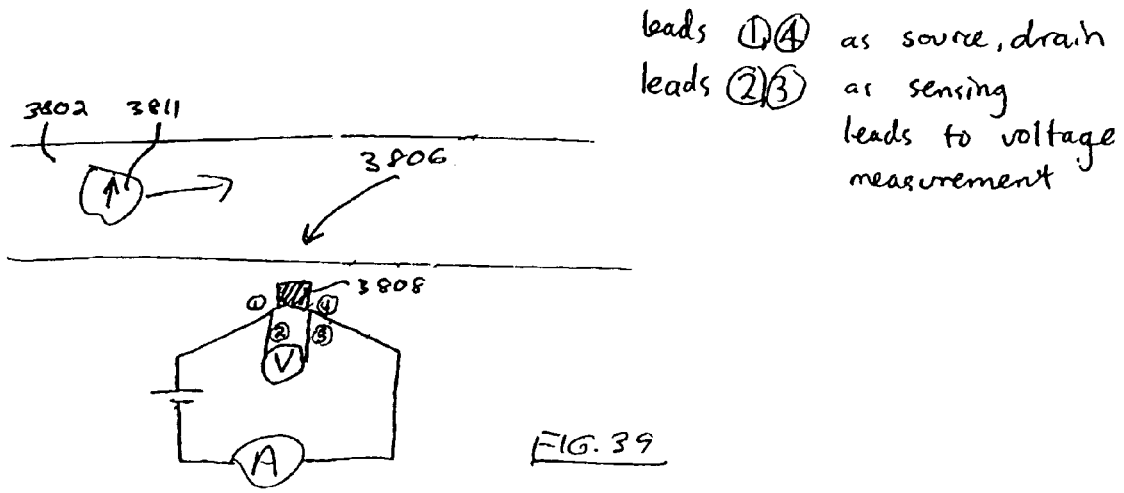
FIG. 39 shows a simplified plan view of still another alternative embodiment of a magnetic-based detection apparatus in accordance with the present invention.

A potential difference from a power supply is applied across sensor 3808. The passage of a magnetized detectable entity 3811 through detection region 3806 is sensed by measuring the impedance of sensor 3808. FIG. 38 shows measurement of impedance by a two-wire method, and FIG. 39 shows measurement of impedance by a four wire measurement.

The various electronic- and magnetic-based sensing described above differ in their mechanism for sensing detectable entities, but all function by detecting a changed electrical or magnetic environment within a specific detection region. In order to correlate a changed electrical or magnetic environment in this region with a specific entity or ensemble of entities, a detection volume must be defined.

Specifically, because many of the entities sought to be detected by embodiments of the present invention are of small size, it is important to define a small enough detection volume such that only one entity, or a particular ensemble of entities, may be present in the detection volume and available for detection at a given time. A sufficiently small detection volume can be defined in several ways.

One approach is through sample dilution. By making the concentration of the sample sufficiently low, the presence of only one detectable entity within a given detection volume is ensured.

An alternative approach to defining the detection volume is by controlling the physical dimensions of the detection region. By making the detection region sufficiently small, the presence of only one detectable entity is ensured. One way of accomplishing this would be to utilize a constriction in a width of the flow channel.

Embodiments of microfluidic structures in accordance with the present invention are particularly suited for defining the detection volume utilizing this approach. Specifically, the mold defining the width of a flow channel and hence the dimensions of the detection volume can be precisely controlled at very small dimensions utilizing photolithographic techniques well known in the art of semiconductor fabrication. Hence, the size and variety of materials that may be detected within the constriction can be readily controlled during fabrication of the microfluidic device.

TABLE A listing the range of dimensions of some detectable entities, along with a range of dimensions for the channel at the measurement location is given below.

TABLE A

| SORTABLE ENTITY | APPROXIMATE SIZE RANGE OF SORTABLE ENTITY (µm) | APPROXIMATE RANGE OF WIDTH AT DETECTION LOCATION (µm) |
|---|---|---|
| bacterial cell | 1-10 | 5-50 |
| mammalian cell | 5-100 | 10-500 |
| egg cell | 10-1000 | 10-1000 |
| sperm cell | 1-10 | 10-100 |
| DNA strands | 0.003-1 | 0.001-10 |
| proteins | 0.01-1 | 0.001-10 |
| micelles | 0.1-100 | 1-500 |
| viruses | 0.05-1 | 1-10 |
| larvae | 600-6500 | VARIABLE |
| beads | 0.01-100 | VARIABLE |

The size of the detection region is chosen to optimize the utility of the entire device. The dimensions are chosen such that the presence of the detected entity causes a readily measurable change in the electrical or magnetic properties of the region, while at the same time permitting the sample to flow.

As previously described, many electronic-based detection techniques of the present invention utilize the application and sensing of an electric field between electrodes. Accordingly, another approach to defining a detection volume is to adjust the electrode size in order to limit the volume to which the electric field is applied.

Other approaches to defining detection volume are time based. Specifically, a duration of measurement of the electrical or magnetic environment may be kept short, so as to limit the number of entities entering the detection volume. Alternatively, the rate of flow of sample into the detection volume may be controlled, such that the allowable duration for a measurement is within a practical range While the above description has focused upon detection of a single detectable entity, the invention is not limited to this approach. An alternative embodiment in accordance with the present invention may detect ensembles of entities. Such ensembles can include any number of entities which are either too small, or too numerous in the measurement region, to be individually detected. Such ensembles of entities would be detected by their collective effect on the electrical or magnetic environment of the detection volume. Ensembles of entities for which this application could be employed include, but are not limited to, solutions of macromolecules such as nucleic acids and proteins.

3. Electrode Structure and Formulation

Sensing in accordance with electronic- and magnetic-based approaches of the present invention may rely upon the use of electrically conducting structures. Such electrically conducting structures may have any combination of a number of desirable properties, including but not limited to mechanical flexibility, adhesion to the surrounding elastomer material, resistance to chemical attack, and uniform and low surface resistivity.

For example, while the previous FIGS. have illustrated conductive structures in the form of simple, uniform planar electrodes, embodiments of conductive structures for obtaining data on samples in microfluidic channels within the scope of the present invention are not limited to these structures.

Electrically conducting members utilized by embodiments in accordance with the present invention may assume a wide variety of shapes and sizes. The electrodes may be flexible such that they retain their electrically conducting character when physically deformed or stretched.

Figure 40:
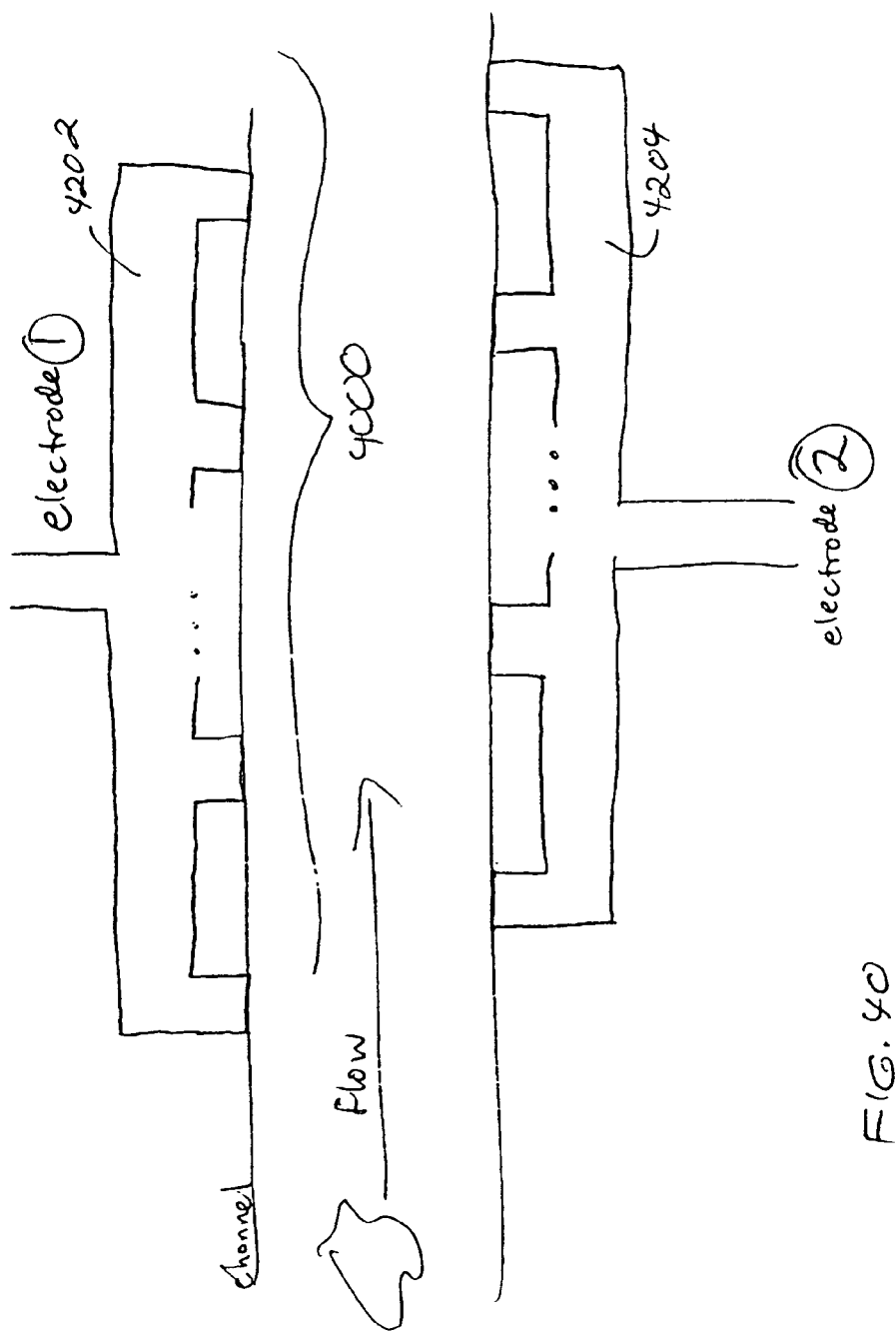
FIG. 40 shows a simplified plan view of a detection region in accordance with an alternative embodiment of the present invention

FIG. 40 shows a plan view of a detection region 4000 in accordance with an alternative embodiment in accordance with the present invention, wherein the conductive structures comprise 'comb-like' arrays 4002 and 4004. Opposing electrode combs 4002 and 4004 may either face each other edge-on as shown in FIG. 40, or may feature interlaced combs to form an interdigitated structure. Such complex electrode shapes enhance the sensitivity of the information collected.

While the previous figures depict simple electrodes having uniform composition, this is not required by the present invention. Electrodes useful with the present invention may have a complex structure featuring regions of high and low conductivity. One example of such a complex electrode structure would utilize highly conductive regions in combination with regions of intermediate conductivity in order to create regions of homogenous charge.

Such intermediate conductivity regions could be formed utilizing an elastomer incorporating precisely-controlled amounts of conductive materials such as carbon black, colloidal silver, and charge transfer complexes such as tetrathiafulavalene/tetracyanoquinodimethane. Such intermediate-conductivity regions could have a surface resistivity of between about $10^6$-$10^{11}\Omega$.

Moreover, the surface of the electrically conducting members in accordance with the present invention need not have smooth surfaces. Electrodes or conducting members having textured surfaces can also be employed to allow flexibility in more than one direction.

The electrically conducting structures utilized by detection apparatuses in accordance with embodiments of the present invention may be fabricated in a number of ways. Conducting structures integrated within an elastomer material in accordance with embodiments of the present invention can be fabricated utilizing a variety of techniques. One approach to integrating conducting structures with an elastomeric material involves incorporating a conducting polymer within the elastomeric material.

Another approach to electrode formation is to utilize an elastomer binder that includes electrically conducting materials. In this regard, possible materials include binder materials such as PDMS containing conducting particles such as ZELEC®, manufactured by Milliken Chemical of Spartanburg, S.C.. Examples of other possible candidates of electrically conducting materials include VULCAN® carbon black material, manufactured by Cabot Corp. of Alpharetta, Ga. Carbon in the form of conducting fibrils or nanotubes may also be employed to convey conductivity for electrode materials in accordance with the present invention. For water-based elastomer materials, conductivity can be conferred by the addition of dopants such as iodine or organic salts such as potassium iodide, There are a number of commercially available conductive polymers suitable for this purpose. These conductive polymers are generally provided in a monomer formulation which can be polymerized to conduct electricity.

However, at least one commercial product is sold in polymer form without the need for polymerization. This product is BAYTRON®, manufactured by Bayer Corporation of Pittsburgh, Pa. This product can be applied by spraying, spinning, and stenciling techniques. It is also possible to pattern BAYTRON® with photolithographic resolution which is suitable for microfabricated elastomeric channels in accordance with embodiments of the present invention.

Still another approach to electrode formation in accordance with embodiments of the present invention is the direct incorporation of metals such as gold, silver, or aluminum within the microfluidic structure. In one embodiment, metal electrode structures may be patterned upon the elastomer material using chemical or physical vapor deposition techniques, for example. A metallic electrode may be used in conjunction with an intermediate layer to promote adhesion between the metal and elastomer. Alternatively, metals could be physically introduced into the elastomer material, for example by ion implantation or other techniques.

In addition to the use of solid materials as conductive members, alternative embodiments in accordance with the present invention may also utilize electrically conducting fluids coated onto elastomer materials or formed in pockets within the elastomeric structure. Examples of electrically conducting fluids that may serve as electrodes include but are not limited to colloidal suspensions of conducting particles and ionic solutions. The viscosity of the conducting fluid may be high, for example where conductive greases such as carbon grease or silver grease are used.

Sensing structures and methods of the present invention are potentially applicable to a broad range of applications. For example, by detecting and characterizing single entities in real time, embodiments in accordance with the present invention may be employed as sensing elements for sorting devices, an example of which is described in connection with FIG. 30.

Sensor structures in accordance with the present invention may also be utilized to control flow within a microfluidic device. For example, in certain applications a sample may be flowed against a dialysis membrane. As a result of this flow, concentration of a component of the sample may change as a function of time or as a function of position along the flow channel. Where a change in sample component concentration correlates with a change in the electrical properties to reveal completion of the dialysis process, a valve state may be triggered or pumping may be halted.

Chromatography is another application for detecting changes in sample impedance along a flow path. Where the physical position of a sample after processing (filtering, separation, dialysis) corresponds to a quantity of interest, the final location of a processed analyte must be identified. Other potential applications include the sorting by size achieved by drawing substances through filters such as bead columns or gels.

Another particular application is for nucleic acid sequencing, where the position along the stream of analyte may correspond to a particular length of nucleic acid sequence. Reliance upon distance separation effects is common to most genomic sequencing efforts, and conventional detection of the bands of separated material has been accomplished by optical interrogation.

Still another application for the instant invention is in monitoring gradient elution that is used to controllably dissociate an analyte from the surface of a capillary or column. An example of such a technique is in proteomics, where affinity-based or nonspecific binding to the walls is systematically blocked through use of a pH or concentration gradient applied to the contents of a sample channel.

Sensing approaches in accordance with embodiments of the present invention method offer an alternative to optical detection of the size-sorted fragments, by either employing multiple sensing locations along the sorted 'column' or by recording a time series of data as the 'column' flows past a particular sensing location.

Sensing methods and apparatuses in accordance with the present invention are also particularly suited to the analysis of untreated samples, such as whole blood or environmental fluid samples. The research performed by Sohn et al. referenced above includes discrimination of mammalian white blood cells from red blood cells, through the electrical properties of their DNA content. The ability of a device to discriminate between these cell types has great potential value.

Microfabricated elastomeric devices in accordance with embodiments of the present invention allow fluid handling tasks such as sorting, storage, assaying, and dispensing of analytes to be performed by a single chip. This integrated character of embodiments in accordance with the present invention poses an advantage over conventional approaches that may require one or more washing steps, or direct driving of fluid from an external pump. Examples of specific applications for detection structures and methods in accordance with the present invention include detection of pathogens in blood or water samples, antibody binding studies in different channel locations, and screening of collections of cells from cultures or blood samples.

Sensors in accordance with embodiments of the present invention may also be employed in conjunction with the "cell cages" described above in FIGS. 26 and 27. In such applications, sensors may be employed to monitor the position of cells in a cage; to monitor conditions of the solution surrounding the cells; and to monitor the condition of the cells. The non-intrusive character of detection in accordance with embodiments of the present invention is suited to monitoring changes in a sample that occur over the short term or the long term, from seconds up to weeks or more.

Information that can be obtained utilizing a detector in accordance with the present invention includes cell size, cell internal resistivity and hence internal cell environment, and cell membrane integrity. Detection schemes in accordance with embodiments of the present invention may also reveal the disposition of the cell within the cage, for example the location of the cell and whether or not the cell is bound to the cage surface. This cellular information can be useful in a variety of applications, including but not limited to drug discovery, surface bioaffinity studies, environmental monitoring, and cell culturing.

Embodiments of detection structures and methods in accordance with the present invention also allow for the detection of voids within the microfluidic channel, such as air bubbles within a fluid sample. Sensing the presence of such voids may be important in assessing the operation of microfluidic systems. This is especially true for applications where intake of untreated samples or other field operations can result in the inadvertent inclusion or generation of bubbles within liquid samples.

The application of electronic or magnetic detection methods in accordance with embodiments of the present invention does not preclude concurrent utilization of optical sensing techniques. By combining electronic and magnetic detection methods sensors described here with established optical techniques, new capabilities may be created. One example of such a new capability is to employ sensors in accordance with embodiments of the present invention as non-invasive monitoring devices used to trigger optical excitation. Such a triggering scheme has the benefit of reducing the required time of excitation of fluorescent dyes or molecular tags, thereby reducing the probability of photobleaching within a particular time period, and prolonging the time before optically-induced sample degradation can be expected to occur.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention but that the invention will include all embodiments and equivalents falling within the scope of the claims.

What is claimed is:

1. A method of detecting entities of a selected entity type in a microfabricated structure, wherein the entity type is selected from bacterial cells, mammalian cells, and viral particles, the method comprising:
 (a) providing a microfabricated structure including a flow channel, and a deflectable elastomeric membrane; wherein the flow channel comprises a detection volume having selected physical dimensions with a selected width;
 (b) applying an electric field across the detection volume;
 (c) flowing a fluid containing a plurality of entities of the selected entity type through the detection volume at a selected flow rate;
 (d) measuring a change in current and/or voltage of said applied electric field resulting from one of the entities in the fluid passing through and past the detection volume; and
 (e) correlating said change(s) with the presence of an entity of the selected entity type within the flow channel, wherein the method comprises selecting a microfabricated structure having the physical dimensions and width of the detection volume specified in step (a), in conjunction with a flow rate of the fluid through the detection volume specified in step (c), such that the combination of said physical dimensions and width of the flow channel and said flow rate result in only one entity of the selected entity type passing through the detection volume at a time.

2. The method of claim 1, wherein step (d) comprises measuring a change in voltage across the detection volume.

3. The method of claim 1, wherein step (d) comprises measuring a change in current across the detection volume.

4. The method of claim 1, wherein the detection volume is defined by electrodes separated from the flow channel by a dielectric material that permits an AC electrical field to be applied by the electrodes through the flow channel.

5. The method of claim 1, wherein the deflectable membrane is an elastomer with a Young's modulus of 50 Pa to 10 MPa.

6. The method of claim 1, wherein the deflectable membrane is an elastomer with a Young's modulus of about 1 MPa.

7. The method of claim 1, wherein the wherein the deflectable membrane comprises polydimethylsiloxane (PDMS).

8. The method of claim 1 wherein changes in the current and/or voltage are detected by electrodes positioned transversely on opposite sides of the detection volume.

9. The method of claim 8 wherein the same electrodes are used to apply the electric field and to detect the change in voltage and/or current across the detection volume.

10. The method of claim 8 wherein different electrodes are used to apply the electric field and to detect the change in voltage and/or current across the detection volume.

11. The method of claim 8 wherein the electrodes are in communication with an AC power supply such that an electric field having a constant frequency of oscillation is applied across the detection volume.

12. The method of claim 8 wherein the electrodes are in communication with an AC power supply such that said electric field varies in frequency of oscillation during measurement.

13. The method of claim 8 wherein the electrodes are in communication with a DC power supply such that a constant electric field is applied along the detection volume.

14. The method of claim 1 wherein changes in the current and/or voltage are detected by electrodes positioned at different points longitudinally along the flow channel.

15. The method of claim 14 wherein the same electrodes are used to apply the electric field and to detect the change in voltage and/or current along the detection volume.

16. The method of claim 14 wherein different electrodes a reused to apply the electric field and to detect the change in voltage and/or current across the detection volume.

17. The method of claim 14 wherein the electrodes are in communication with an AC power supply such that an electric field having a constant frequency of oscillation is applied along the detection volume.

18. The method of claim 14 wherein the electrodes are in communication with an AC power supply such that said electric field varies in frequency of oscillation during measurement.

19. The method of claim 14 wherein the electrodes are in communication with a DC power supply such that a constant electric field is applied along the detection volume.

20. A method of detecting a magnetized entity of a selected entity type in a microfabricated structure, wherein the entity type is selected from bacterial cells, mammalian cells, viral particles, microparticles, and nanoparticles, the method comprising:
    (a) providing the microfabricated structure including a flow channel and a deflectable membrane;
    wherein within the flow channel is a detection volume configured to receive one entity of the selected entity type or an ensemble thereof at a time;
    wherein the microfabricated structure further comprises a conductive coil structure proximate to the detection volume;
    (b) measuring a current and/or a voltage induced in the coil structure by passage of an entity of the selected entity type or an ensemble thereof through the detection volume; and
    (c) correlating the current and/or voltage induced in the coil structure with the presence of an entity of the selected entity type within the flow channel.

21. The method of claim 20 wherein the conductive coil structure is formed in elastomeric material adjacent to the flow channel.

22. The method of claim 20 wherein the conductive coil structure is coaxial with the flow channel.

23. A method of detecting a magnetized entity of a selected entity type in a microfabricated structure, wherein the entity type is selected from bacterial cells, mammalian cells, viral particles, microparticles, and nanoparticles, the method comprising:
    (a) providing the microfabricated structure including a flow channel and a deflectable membrane;
    wherein within the flow channel is a detection volume configured to receive one entity of the selected entity type or an ensemble thereof at a time;
    wherein the microfabricated structure further comprises a magnetoresistive element proximate to the detection volume;
    (b) measuring a changed resistance across the magnetoresistive element caused by passage of an entity of the selected entity type or an ensemble thereof through the detection volume; and
    (c) correlating said changed resistance with the presence of an entity of the selected entity type within the flow channel.

24. A method of detecting isolated macromolecules in a microfabricated structure, the method comprising:
    (a) providing a microfabricated structure including a flow channel and a deflectable membrane;
    wherein the flow channel comprises a detection volume having selected physical dimensions with a selected width;
    (b) applying an electric field to the detection volume;
    (c) flowing a fluid containing said isolated macromolecules through the detection volume at a selected flow rate;
    (d) measuring a change in current and/or voltage of said applied electric field resulting from a macromolecule or ensemble thereof passing through and past the detection volume; and
    (e) correlating said change(s) with the presence of a macromolecule within the flow channel,
    wherein the method comprises selecting a microfabricated structure having the physical dimensions and width of the detection volume specified in step (a), in conjunction with a flow rate of the fluid through the detection volume specified in step (c), such that the combination of said physical dimensions and width of the flow channel and said flow rate result in only one of said macromolecules or an ensemble thereof passing through the detection volume at a time.

25. The method of claim 24 wherein said macromolecule is a nucleic acid or a protein.

26. The method of claim 24, wherein step c) comprises measuring a change in voltage across the detection volume, and step d) comprises correlating the change in voltage with the presence of a macromolecule within the flow channel.

27. The method of claim 24, wherein step c) comprises measuring a change in current across the detection volume, and step d) comprises correlating the change in current with the presence of a macromolecule within the flow channel.

28. The method of claim 24, wherein the detection volume is defined by electrodes separated from the flow channel by a dielectric material that permits an AC electrical field to be applied by the electrodes through the flow channel.

29. The method of claim 24 wherein changes in the current and/or voltage are detected by electrodes positioned transversely on opposite sides of the detection volume.

30. The method of claim 29 wherein the same electrodes are used to apply the electric field and to detect the change in voltage and/or current across the detection volume.

31. The method of claim 29 wherein different electrodes are used to apply the electric field and to detect the change in voltage and/or current across the detection volume.

32. The method of claim 29 wherein the electrodes are in communication with an AC power supply such that said electric field has a constant frequency of oscillation.

33. The method of claim 29 wherein the electrodes are in communication with an AC power supply such that said electric field varies in frequency of oscillation during measurement.

34. The method of claim 29 wherein the electrodes are in communication with a DC power supply such that a constant electric field is applied along the detection volume.

35. The method of claim 24 wherein changes in the current and/or voltage are detected by electrodes positioned at different points longitudinally along the flow channel.

36. The method of claim 35 wherein the same electrodes are used to apply the electric field and to detect the change in voltage and/or current across the detection volume.

37. The method of claim 35 wherein different electrodes are used to apply the electric field and to detect the change in voltage and/or current across the detection volume.

38. The method of claim 35 wherein the electrodes are in communication with an AC power supply such that said electric field has a constant frequency of oscillation.

39. The method of claim 35 wherein the electrodes are in communication with an AC power supply such that said electric field varies in frequency of oscillation during measurement.

40. The method of claim 35 wherein the electrodes are in communication with a DC power supply such that a constant electric field is applied along the detection volume.

* * * * *